US008357665B2

(12) United States Patent
Kandimalla et al.

(10) Patent No.: US 8,357,665 B2
(45) Date of Patent: *Jan. 22, 2013

(54) IMMUNE REGULATORY OLIGONUCLEOTIDE (IRO) COMPOUNDS TO MODULATE TOLL-LIKE RECEPTOR BASED IMMUNE RESPONSE

(75) Inventors: Ekambar R. Kandimalla, Southboro, MA (US); Daqing Wang, Bedford, MA (US); Yukui Li, Newton, MA (US); Dong Yu, Westboro, MA (US); FuGang Zhu, Bedford, MA (US); Lakshmi Bhagat, Framingham, MA (US); Sudhir Agrawal, Shrewsbury, MA (US)

(73) Assignee: Idera Pharmaceuticals, Inc., Cambridge, MA (US)

(*) Notice: Subject to any disclaimer, the term of this patent is extended or adjusted under 35 U.S.C. 154(b) by 733 days.

This patent is subject to a terminal disclaimer.

(21) Appl. No.: 11/549,048

(22) Filed: Oct. 12, 2006

(65) Prior Publication Data

US 2009/0060898 A1 Mar. 5, 2009

Related U.S. Application Data

(60) Provisional application No. 60/726,034, filed on Oct. 12, 2005, provisional application No. 60/784,243, filed on Mar. 21, 2006, provisional application No. 60/825,440, filed on Sep. 13, 2006.

(51) Int. Cl.
*A61K 48/00* (2006.01)
*C12N 15/11* (2006.01)
(52) U.S. Cl. .................................. 514/44; 536/23.1
(58) Field of Classification Search ..................... None
See application file for complete search history.

(56) References Cited

U.S. PATENT DOCUMENTS

| 6,426,334 | B1 | 7/2002 | Agrawal et al. |
| 2004/0097719 | A1 | 5/2004 | Agrawal et al. |
| 2005/0239733 | A1 | 10/2005 | Jurk et al. |
| 2006/0074040 | A1* | 4/2006 | Kandimalla et al. ............ 514/44 |

FOREIGN PATENT DOCUMENTS

| EP | 1393745 A1 * | 3/2004 |
| WO | WO 01/83503 A2 * | 11/2001 |
| WO | WO03/103586 | 12/2003 |
| WO | 2004/094671 A2 | 11/2004 |
| WO | 2005/007672 A2 | 1/2005 |
| WO | WO 2005/007672 A2 | 1/2005 |
| WO | 2007/038720 A2 | 4/2007 |
| WO | 03/103708 A1 | 2/2010 |

OTHER PUBLICATIONS

Lenert et al.; Inhibitory Oligonucleotides Block the Induction of AP-1 Transcription Factor by Stimulatory CpG Oligonucleotides in B Cells; Antisense & Nucleic Acid Drug Development; 13(3):143-150, 2003.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides", J. Immunol., 168:4531-4537 (2002).
Poltorak et al., "Defective LPS Signaling in C3H/Hej and C57BL/10ScCr Mice: Mutations in Tlr4 Gene", Science, 282:2085-2088 (1998).
Underhill et al., "The Toll-like Receptor 2 is Recruited to Macrophage Phagosomes and Discriminates Between Pathogens", Nature, 401:811-815 (1999).
Hayashi et al., "The Innate Immune Response to Bacterial Flagellin is Mediated by Toll-like Receptor 5", Nature, 410:1099-1103 (2001).
Zhang et al., "A Toll-like Receptor that Prevents Infection by Uropathogenic-Bacteria", Science, 303:1522-1525 (2004).
Meier et al., Cell. "Toll-like Receptor (TLR) 2 and TLR4 are Essential for Aspergillus-Induced Activation of Murine Macrophages", Cellular Microbiol., 5(8):561-570 (2003).
Campos et al., "Activation of Toll-like Receptor-2 by Glycosylphosphatidylinositol Anchors from a Protozoan Parasite", J. Immunol., 167:416-423 (2001).
Hoebe et al., "Identification of Lps2 as a Key Transducer of MyD88-Independent TLR Signaling", Nature, 424:743-748 (2003).
Lund et al., "Toll-like Receptor 9-Mediated Recognition of Herpes Simplex Virus-2 by Plasmacytoid Dendritic Cells", J. Exp. Med., 198(3):513-520 (2003).
Heil et al., "Species-Specific Recognition of Single-Stranded RNA via Toll-like Receptor 7 and 8", Science, 303:1526-1529 (2004).
Diebold et al., "Innate Antiviral Responses by Means of TLR7-Mediated Recognition of Single-Stranded RNA", Science, 303:1529-1531 (2004).
Hornung et al., "Replication-Dependent Potent IFN-α Induction in Human Plasmacytoid Dendritic Cells by a Single-Stranded RNA Virus", J. Immunol. 173:5935-5943 (2004).
Akira et al., "Toll-like Receptors: Critical Proteins Linking Innate and Acquired Immunity", Nature Immunol., 2(8):675-680 (2001).
Medzhitov, R., "Toll-like Receptors and Innate Immunity", Nature Rev. Immunol., 1:135-145 (2001).
Cook et al., "Toll-like Receptors in the Pathogenesis of Human Disease", Nature Immunol., 5(10):975-979 (2004).
Liew et al, "Negative Regulation of Toll-like Receptor-Mediated Immune Responses", Nature, 5:446-458 (2005).
Hemmi et al., "Small Anti-viral Compounds Activate Immune Cells via the TLR7 MyD88-Dependent Signaling Pathway", Nat. Immunol., 3(6):196-200 (2002).
Jurk et al., "Human TLR7 or TLR8 Independently Confer Responsiveness to the Antiviral Compound R-848", Nat. Immunol. 3(6):499 (2002).
Lee et al., "Molecular Basis for the Immunostimulatory Activity of Guanine Nucleoside Analogs: Activation of Toll-like Receptor 7", Proc. Natl. Acad. Sci. USA, 100(11):6646-6651 (2003).
Alexopoulou, L. et al., "Recognition of Double-Stranded RNA and Activation of NF-κB by Toll-like Receptor 3", Nature, 413:732-738 (2001).

(Continued)

*Primary Examiner* — Oluwatosin Ogunbiyi
(74) *Attorney, Agent, or Firm* — Wood, Phillips, Katz, Clark & Mortimer

(57) ABSTRACT

The invention provides novel immune regulatory oligonucleotides (IRO) as antagonist of TLRs and methods of use thereof. These IROs have unique sequences that inhibit or suppress TLR-mediated signaling in response to a TLR ligand or TLR agonist. The methods may have use in the prevention and treatment of cancer, an autoimmune disorder, airway inflammation, inflammatory disorders, infectious disease, skin disorders, allergy, asthma or a disease caused by a pathogen.

15 Claims, 26 Drawing Sheets

OTHER PUBLICATIONS

Tokunaga et al., "Antitumor Activity by Deoxyribonucleic Acid Fraction from *Mycobacterium bovis* BCG. I. Isolation, Physicochemical Characterization, and Antitumor Activity", J. Natl. Cancer Inst., 72(4):955-962 (1984).

Shimada et al., "In Vivo Augmentation of Natural Killer Cell Activity with a Deoxyribonucleic Acid Fraction of BCG", Jpn. J. Cancer Res., 77:808-816 (1986).

Yamamoto et al., "In Vitro Augmentation of Natural Killer Cell Activity and Production of Interferon-α/β and -γ with Deoxyribonucleic Acid Fraction from *Mycobacterium bovis* BCG", Jpn. J. Cancer Res., 79:866-873 (1986).

Zhao et al., "Effect of Different Chemically Modified Oligodeoxynucleotides on Immune Stimulation", Biochem. Pharmacol., 51:173-182 (1996).

Hemmi et al., "A Toll-like Receptor Recognizes Bacterial DNA", Nature, 408:740-745 (2000).

Zhao et al., "Modulation of Oligonucleotide-Induced Immune Stimulation by Cyclodextrin Analogs", Biochem. Pharmacol., 52:1537-1544 (1996).

Zhao et al., "Pattern and Kinetics of Cytokine Production Following Administration of Phosphorothioate Oligonucleotides in Mice", Antisense Nucl. Acids Drug Dev., 7:495-502 (1997).

Zhao et al., "Site of Chemical Modifications in CpG Containing Phosphorothioate Oligodeoxynucleotide Modulates its Immunostimulatory Activity", Bioorg. Med. Chem. Lett., 9:3453:3458 (1999).

Zhao et al., "Immunostimulatory Activity of CpG Containing Phosphorothioate Oligodeoxynucleotide is Modulated by Modification of a Single Deoxynucleoside", Bioorg. Med. Chem. Lett., 10:1051-1054 (2000).

Yu et al., "Accessible 5'-End of CpG-Containing Phosphorothioate Oligodeoxynucleotides is Essential for Immunostimulatory Activity", Bioorg. Med. Chem. Lett., 10:2585-2588 (2000).

Yu et al., "Modulation of Immunostimulatory Activity of CpG Oligonucleotides by Site-Specific Deletion of Nucleobases", Bioorg. Med. Chem. Lett., 11:2263-2267 (2001).

Kandimalla et al., "Effect of Chemical Modifications of Cytosine and Guanine in a CpG-Motif of Oligonucleotides: Structure-Immunostimulatory Activity Relationships", Bioorg. Med. Chem., 9:807-813 (2001).

Kandimalla et al., "Immunomodulatory Oligonucleotides Containing a Cytosine-Phosphate-2'-Deoxy-7-Deazaguanosine Motif as Potent toll-like Receptor 9 Agonists", Proc. Natl. Acad. Sci. USA, 102(19):6925-6930 (2005).

Kandimalla et al., "A Dinucleotide Motif in Oligonucleotides Shows Potent Immunomodulatory Activity and Overrides Species-Specific Recognition Observed with CpG Motif", Proc. Natl. Acad. Sci. USA, 100(24):14303-14308 (2003).

Cong et al., "Self-Stabilized CpG DNAs Optimally Activate Human B Cells and Plasmacytoid Dendritic Cells", Biocehm. Biophys. Res. Commun., 310:1133-1139 (2003).

Kandimalla et al., "Secondary Structures in CpG Oligonucleotides Affect Immunostimulatory Activity", Biocehm. Biophys. Res. Commun., 306:948-953 (2003).

Kandimalla et al., "Divergent Synthetic Nucleotide Motif Recognition Pattern: Design and Development of Potent Immunomodulatory Oligodeoxyribonucleotide Agents with Distinct Cytokine Induction Profiles", Nucleic Acids Res., 31(9):2393-2400 (2003).

Yu et al., "Requirement of Nucleobase Proximal to CpG Dinucleotide for Immunostimulatory Activity of Synthetic CpG DNA", Bioorg. Med. Chem., 11:459-464 (2003).

Bhagat et al., "CpG Penta- and Hexadeoxyribonuleotides as Potent Immunomodulatory Agents", Biochem. Biophys. Res. Commun., 300:853-861 (2003).

Yu et al., "Potent CpG Oligonucleotides Containing Phosphodiester Linkages: In Vitro and In Vivo Immunostimulatory Properties", Biochem. and Biophys. Res. Comm., 297:83-90 (2002).

Yu et al., "Design, Synthesis, and Immunostimulatory Properties of CpG DNAs Containing Alkyl-Linker Substitutions: Role of Nucleosides in the Flanking Sequences", J. Med. Chem., 45:4540-4548 (2002).

Noronha et al., "Synthesis and Biophysical Properties of Arabinonucleic Acid (ANA): Circular Dichroic Spectra, Melting Temperatures, and Ribonuclease H Susceptibility of ANA-RNA Hybrid Duplexes", Biochem., 39:7050-7062 (2000).

Yu et al., "Immunomers'-Novel 3'-3"Linked CpG Oligodeoxyribonucleotides as Potent Immunomodulatory Agents", Nucleic Acids Res., 30(20):4460-4469 (2002).

Kandimalla et al., "Conjugations of Ligands at the 5'-End of CpG DNA Affects Immunostimulatory Activity", Bioconjugate Chem., 13:966-974 (2002).

Yu et al., "Immunostimulatory Properties of Phosphorothioate CpG DNA Containing Both 3'-5'- and 2'-5'-Internucleotide Linkages", Nucleic Acids Res., 30(7):1613-1619 (2002).

Kandimalla et al., "Effect of chemical Modifications of Cytosine and Guanine in a CpG-Motif of Oligonucleotides: Structure-Immunostimulatory Activity Relationships", Bioorg. & Med. Chem., 9:807-813 (2001).

Yu et al., "Accessible 5'-End of CpG-Containing Phosphorothioate Oligodeoxynucleotides is Essential for Immunostimulatory Activity", Bioorg. & Med. Chem., 10:2585-2588 (2000).

Putta et al., "Novel Oligodeoxynucleotide Agonists of TLR9 Containing $N^3$-Me-dC or $N^1$-Me-dG Modifications", Nucleic Acids Res., 34(11):3231-3238 (2006).

Lenert et al., "Structural Characterization of the Inhibitory DNA Motif for the Type A (D)-CpG-induced Cytokine Secretion and NK-Cell Lytic Activity in Mouse Spleen Cells", DNA and Cell Biol., 22(10):621-631 (2003).

Chen et al., "Identification of Methylated CpG Motifs as Inhibitors of the Immune Stimulatory CpG Motifs", Gene Therapy, 8:1024-1032 (2001).

Stunz et al., "Inhibitory Oligonucleotides Specifically Block Effects of Stimulatory CpG Oligonucleotides in B Cells", Eur. J. Immunol., 32:1212-1222 (2002).

Duramad et al., "Inhibitors of TLR-9 Act on Multiple Cell Subsets in Moue and Man In Vitro and Prevent Death In Vivo from Systemic Inflammation", The Journal of Immunol., 174:5193-5200 (2005).

Patole et al., "G-Rich DNA Suppresses Systemic Lupus", J. Am. Soc. Nephrol., 16:3273-3280 (2005).

Gursel et al., "Repetitive Elements in Mammalian Telomeres Suppress Bacterial DNA-Induced Immune Activation", The Journal of Immunol., 171:1393-1400 (2003).

Shirota et al., "Suppressive Oligodeoxynucleotides Inhibit Th1 Differentiation by Blocking IFN-γ- and IL-12-Mediated Signaling", The Journal of Immunol., 173:5002-5007 (2004).

Verthelyi et al., "Human Peripheral Blood Cells Differentially Recognize and Respond to Two Distinct CpG Motifs", The Journal of Immunol. 166:2372-2377 (2001).

Gursel et al., "Differential and Competitive Activation of Human Immune Cells by Distinct Classes of CpG Oligodeoxynucleotide", Journal of Leukocyte Biol., 71:813-820 (2002).

Krug et al., "Identification of CpG Oligonucleotide Sequences with High Induction of IFN-α/β in Plasmacytoid Dendritic Cells", Eur. J. Immunol., 31:2154-2163 (2001).

Ballas et al., "Divergent Therapeutic and Immunologic Effects of Oligodeoxynucleotides with Distinct CpG Motifs", The Journal of Immunol., 167:4878-4886 (2001).

Verthelyi et al., "CpG Oligodeoxynucleotides Protect Normal and SIV-Infected Macaques from *Leishmania* Infection", The Journal of Immunol., 170:4717-4723 (2003).

McShan et al., "Inhibition of Transcription of HIV-1 in Infected Human Cells by Oligodeoxynucleotides Designed to Form DNA Triple Helices", The Journal of Biol. Chem., 267(8):5712-5721 (1992).

Rando et al., "Suppression of Human Immunodeficiency Virus Type 1 Activity In Vitro by Oligonucleotides which Form Intramolecular Tetrads", the Journal of Biol. Chem., 270(4):1754-1760 (1995).

Benimetskaya et al., "Formation of a G-Tetrad and Higher Order Structures Correlated with Biological Activity of the ReIA (NF-κBp65) 'Antisense' Oligodeoxynucleotide", Nucleic Acids Res., 25(13):2648-2656 (1997).

Bock et al., "Selection of Single-Stranded DNA Molecules that Bind and Inhibit Human Thrombin", Nature, 355:564-566 (1992).

Padmanabhan et al., "The Structure of α-Thrombin Inhibited by a 15-Mer Single-Stranded DAN Aptamer", J. Biol. Chem., 268(24):17651-17654 (1993).

Hunziker et al., "Nucleic Acid Analogues: Synthesis and Properties", Mod. Syn. Methods, 7:331-417 (1995).

Crooke et al., "Progress in Antisense Oligonucleotide Therapeutics", Ann. Rev. Pharm. Tox., 36:107-129 (1996).

Gursel et al., "Repetitive Elements in Mammalian Telomeres Suppress Bacterial DNA-Induced Immune Activation", The Journal of Immunology, 171:1393-1400 (2003).

Shirota et al., "Suppressive Oligodeoxynucleotides Protect Mice From Lethal Endotoxic Shock", The Journal of Immunology, 174:4579-4583 (2005).

Shirota et al., "Suppressive Oligodeoxynucleotides Inhibit Th1 Differentiation by Blocking IFN-γ- and IL-12 Mediated Signaling", The Journal of Immunology, 173:5002-5007 (2004).

Yamada et al., "Effect of Suppressive DNA on CpG-Induced Immune Activation", The Journal of Immunology, 169:5590-5594 (2002).

Zeuner et al., "Influence of Stimulatory and Suppressive DNA Motifs on Host Susceptibility to Inflammatory Arthritis", Arthritis & Rheumatism, 48(6):1701-1707 (2003).

Klinman et al., "Regulation of CpG-Induced Immune Activation by Suppressive Oligodeoxynucleotides", Ann. N.Y. Acad. Sci., 1002:112-123 (2003).

Duramad et al., "Inhibitors of TLR-9 Act on Multiple Cell Subsets in Mouse and Man In Vitro and Prevent Death In Vivo from Systemic Inflammation", The Journal of Immunology, 174:5193-5200 (2005).

* cited by examiner

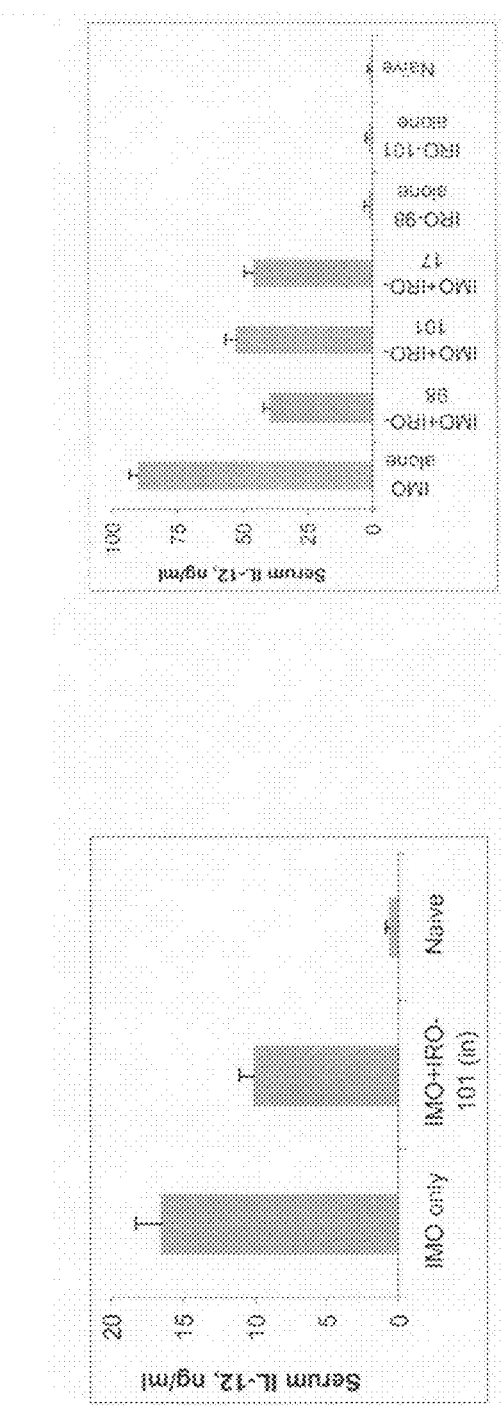

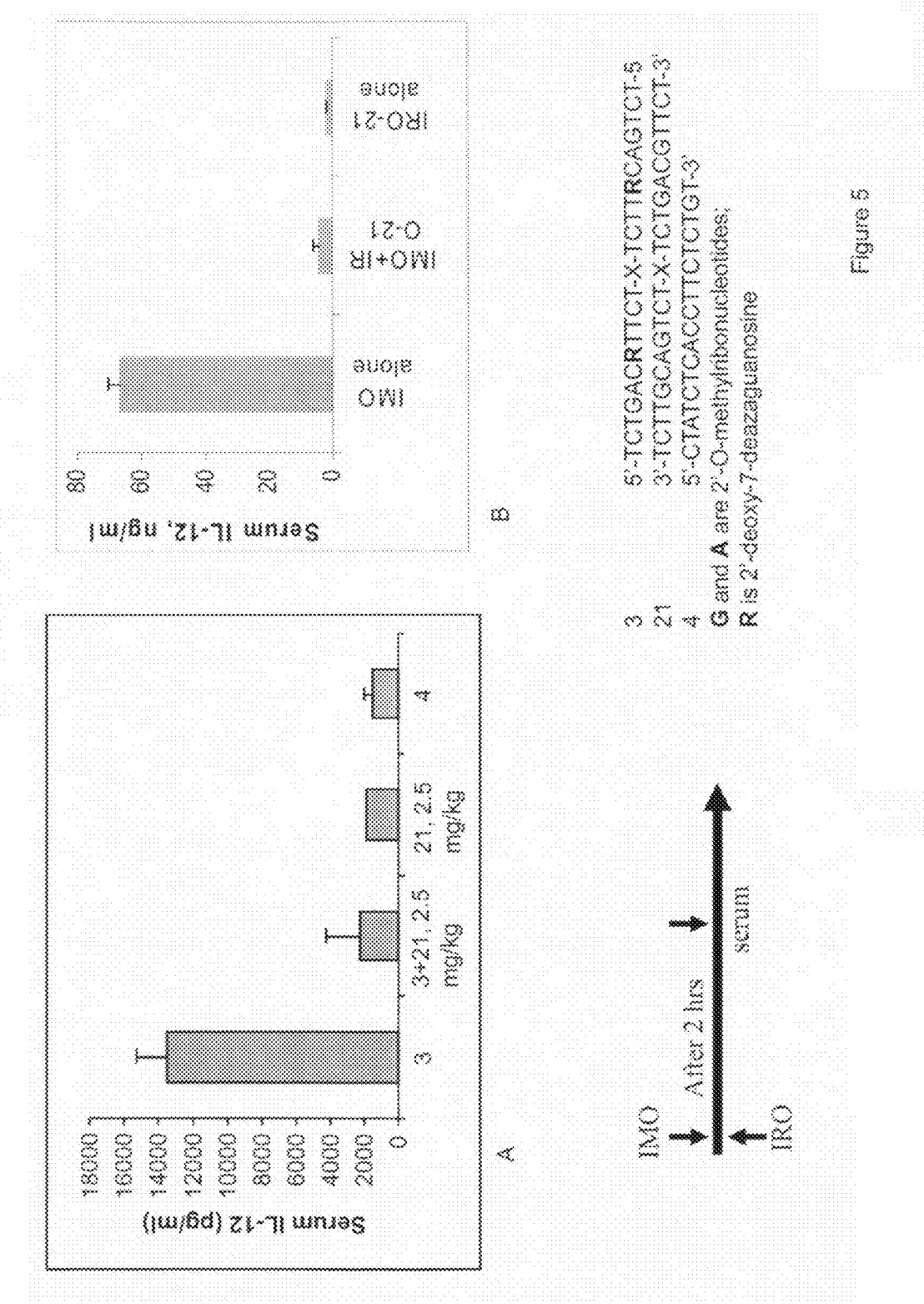

* 25-50% inhibition
** >50% inhibition

* 25-50% inhibition
** >50% inhibition

* 25-50% inhibition
** >50% inhibition

* 25-50% inhibition
** >50% inhibition

* 25-50% inhibition
** >50% inhibition

* 25-50% inhibition
** >50% inhibition

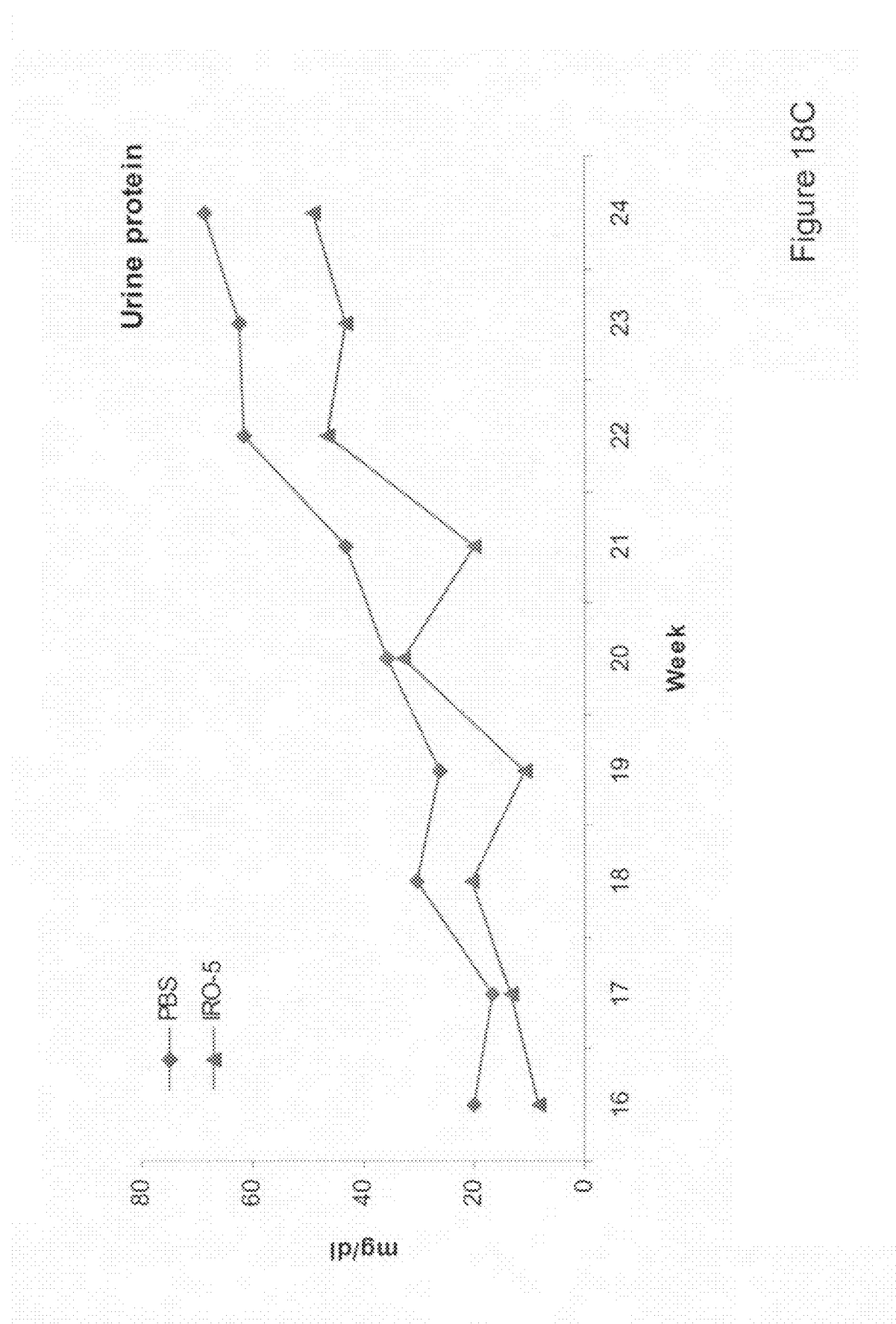

IMMUNE REGULATORY OLIGONUCLEOTIDE (IRO) COMPOUNDS TO MODULATE TOLL-LIKE RECEPTOR BASED IMMUNE RESPONSE

RELATED APPLICATIONS

This application claims the benefit of U.S. Provisional Application Ser. No. 60/726,034, filed on Oct. 12, 2005; U.S. Provisional Application Ser. No. 60/784,243, filed on Mar. 21, 2006; and U.S. Provisional Application Ser. No. 60/825,440, filed on Sep. 13, 2006, the contents of which are incorporated herein by reference in their entirety.

BACKGROUND OF THE INVENTION

1. Field of the Invention

The invention generally relates to the field of immunology and immunotherapy, and more specifically to immune regulatory oligonucleotide (IRO) compositions and their use for inhibition and/or suppression of Toll-like Receptor-mediated immune responses.

2. Summary of the Related Art

Toll-like receptors (TLRs) are present on many cells of the immune system and have been shown to be involved in the innate immune response (Hornung, V. et al., (2002) J. Immunol. 168:4531-4537). In vertebrates, this family consists often proteins called TLR1 to TLR10, which are known to recognize pathogen associated molecular patterns from bacteria, fungi, parasites, and viruses (Poltorak, a. et al. (1998) Science 282:2085-2088; Underhill, D. M., et al. (1999) Nature 401: 811-815; Hayashi, F. et. al (2001) Nature 410:1099-1103; Zhang, D. et al. (2004) Science 303:1522-1526; Meier, A. et al. (2003) Cell. Microbiol. 5:561-570; Campos, M. A. et al. (2001) J. Immunol. 167: 416-423; Hoebe, K. et al. (2003) Nature 424: 743-748; Lund, J. (2003) J. Exp. Med. 198:513-520; Heil, F. et al. (2004) Science 303:1526-1529; Diebold, S. S., et al. (2004) Science 303:1529-1531; Hornung, V. et al. (2004) J. Immunol. 173:5935-5943). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). TLRs have also been shown to play a role in the pathogenesis of many diseases, including autoimmunity, infectious disease, and inflammation (Cook, D. N. et al. (2004) Nature Immunol. 5:975-979) and the regulation of TLR-mediated activation using appropriate agents may provide a means for disease intervention.

Some TLRs are located on the cell surface to detect and initiate a response to extracellular pathogens and other TLRs are located inside the cell to detect and initiate a response to intracellular pathogens. Table 1 provides a representation of TLRs and the known agonists therefore (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413:732-738).

TABLE 1

| TLR Molecule | Agonist |
| --- | --- |
| Cell Surface TLRs: | |
| TLR2 | bacterial lipopeptides |
| TLR4 | gram negative bacteria |
| TLR5 | motile bacteria |
| TLR6 | gram positive bacteria |
| Endosomal TLRs: | |
| TLR3 | double stranded RNA viruses |
| TLR7 | single stranded RNA viruses |
| TLR8 | single stranded RNA viruses |
| TLR9 | unmethylated DNA |

Certain unmethylated CpG motifs present in bacterial and synthetic DNA have been shown to activate the immune system and induce antitumor activity. (Tokunaga T et al., J. Natl. Cancer Inst. (1984) 72:955-962; Shimada S, et al., Jpn. H cancer Res, 1986, 77, 808-816; Yamamoto S, et al., Jpn. J. Cancer Res., 1986, 79, 866-73). Other studies using antisense oligonucleotides containing CpG dinucleotides have been shown to stimulate immune responses (Zhao Q, et al. (1996) Biochem. Pharmacol. 26:173-182). Subsequent studies demonstrated that TLR9 recognizes unmethylated CpG motifs present in bacterial and synthetic DNA (Hemmi, H. et al. (2000) Nature 408:740-745). Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813). In addition, structure activity relationship studies have allowed identification of synthetic motifs and novel DNA-based compounds that induce specific immune response profiles that are distinct from those resulting from unmethylated CpG dinucleotides. (Kandimalla, E. et al. (2005) Proc. Natl. Acad. Sci. USA 102:6925-6930. Kandimalla, E. et al. (2003) Proc. Nat. Acad. Sci. USA 100: 14303-14308; Cong, Y. et al. (2003) Biochem Biophys Res. Commun. 310:1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem. 11:459-464; Bhagat, L. et al. (2003) Biochem. Biophys. Res. Commun. 300:853-861; Yu, D. et al. (2002) Nucleic Acids Res. 30:4460-4469; Yu, D. et al. (2002) J. Med. Chem. 45:4540-4548. Yu, D. et al. (2002) Biochem. Biophys. Res. Commun. 297:83-90; Kandimalla. E. et al. (2002) Bioconjug. Chem. 13:966-974; Yu, D. et al. (2002) Nucleic Acids Res. 30:1613-1619; Yu, D. et al. (2001) Bioorg. Med. Chem. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFN-gamma and a concomitant activation of CTLs. Alternatively, the Th cells involved as helper cells for B-cell activation are Th2 cells. Th2 cells have been shown to be activated in response to bacteria and parasites and may mediate the body's adaptive immune response (e.g. IgE production and eosinophil activation) through the secretion of IL-4 and IL-5. The type of immune response is influenced by the cytokines produced in response to antigen exposure and the differences in the cytokines secreted by Th1 and Th2 cells may be the result of the different biological functions of these two subsets.

While activation of TLRs is involved in mounting an immune response, an uncontrolled stimulation of the immune system through TLRs may exacerbate certain diseases in immune compromised subjects. In recent years, several groups have shown the use of synthetic oligodeoxyoligonucleotides (ODNs) as inhibitors of inflammatory cytokines (Lenert, P. et al. (2003) DNA Cell Biol. 22(10):621-631).

Using certain synthetic ODNs, Lenert et al. report the ability to produce inhibitory ODNs (Lenert, P. et al. (2003) DNA Cell Biol. 22(10):621-631). These inhibitory ODN require two triplet sequences, a proximal "CCT" triplet and a distal "GGG" triplet. In addition to these triplet-containing inhibitory ODNs, several groups have reported other specific DNA sequences that could inhibit TLR-9-mediated activation by CpG-containing ODNs. These "inhibitory" or "suppressive" motifs are rich in poly "G" (e.g. "GGGG") or "GC" sequences, tend to be methylated, and are present in the DNA of mammals and certain viruses (see e.g., Chen, Y., et al., Gene Ther. 8: 1024-1032 (2001); Stunz, L. L., Eur. J. Immunol. 32: 1212-1222 (2002). Duramad, O., et al., J. Immunol., 174: 5193-5200 (2005) and Jurk et. al (US 2005/0239733), describe a structure for inhibitory DNA oligonucleotides containing a GGGG motif within the sequences. Patole et al. demonstrate that GGGG containing ODNs will suppress systemic lupus (Patole, P. et al. (2005) J. Am. Soc. Nephrol. 16:3273-3280). Additionally, Gursel, I., et al., J. Immunol., 171: 1393-1400 (2003), describe repetitive TTAGGG elements, which are present at high frequency in mammalian telomeres, down-regulate CpG-induced immune activation. Shirota, H., et al., J. Immunol., 173: 5002-5007 (2004), demonstrate that synthetic oligonucleotides containing the TTAGGG element mimic this activity and could be effective in the prevention/treatment of certain Th1-dependent autoimmune diseases.

In contrast, recent studies have called into question the view that poly G containing ODNs are acting as antagonists of TLRs. For example, U.S. Pat. No. 6,426,334, Agrawal et al., demonstrate that administering CpG oligonucleotides containing GGGG strings have potent antiviral and anticancer activity, and further that administration of these compounds will cause an increase in serum IL-12 concentration. Further, CpG oligos containing polyG sequences are known to induce immune responses through TLR9 activation (Verthelyi D et al, J Immunol. 166, 2372, 2001; Gursel M et al, J Leukoc Biol, 71, 813, 2001, Krug A et al, Eur J Immunol, 31, 2154, 2001) and show antitumor, antiviral activities (Ballas G K et al, J Immunol, 167, 4878, 2001; Verthelyi D et al, J Immunol, 170, 4717, 2003). In addition, polyG oligonucleotides are also known to inhibit HIV and Rel A (McShan W M, et al, J Biol Chem., 267(8):5712-21, 1992; Rando, R F et al., J Biol Chem, 270(4):1754-60, 1995; Benimetskaya L, et al., Nucleic Acids Res., 25(13):2648-56, 1997). In addition, ODNs containing an immune stimulatory CpG motif and 4 consecutive G nucleotides (class A ODNs) induce interferon-γ production and a Th1 shift in the immune response. Moreover, in preclinical disease models, Class A ODN have been shown to induce a TLR-mediated immune response.

In addition, oligonucleotides containing guanosine strings have been shown to form tetraplex structures, act as aptamers and inhibit thrombin activity (Bock L C et al., Nature, 355: 564-6, 1992; Padmanabhan, K et al., J Biol Chem., 268(24): 17651-4, 1993). Thus it is not clear whether single-stranded or multiple-stranded structures are effective at suppressing TLR9 activation.

Thus, there is a need for effective antagonist of TLRs without a concern that they will form secondary structures.

BRIEF SUMMARY OF THE INVENTION

The invention provides novel immune regulatory oligonucleotides (IRO) compounds as antagonists of TLRs and methods of use thereof. These IROs have one or more chemical modifications in the sequence flanking an immune stimulatory motif and/or in an oligonucleotide motif that would be immune stimulatory but for the modification.

The invention further provides novel IRO compositions having the structure 5-$N_m$—$N_3N_2N_1CGN^1N^2N^3$—$N^m$-3', wherein CG is an oligonucleotide motif and C is cytosine or a pyrimidine nucleotide derivative or non-nucleotide linkage, and G is guanosine a purine nucleotide derivative or non-nucleotide linkage; N1-N3, at each occurrence, is independently a nucleotide, nucleotide derivative or non-nucleotide linkage; Nm, at each occurrence, is independently a nucleotide, nucleotide derivative or non-nucleotide linkage; provided that at least one N1 to N3 and/or C and/or G is a nucleotide derivative or non-nucleotide linkage; and further provided that compound contains less than 4 consecutive guanosine nucleotides wherein the oligonucleotide motif would be immune stimulatory but for the nucleotide derivative or non-nucleotide linkage; and wherein m is a number from 0 to about 30.

The invention further provides for a pharmaceutical composition comprising any an IRO and a pharmaceutically acceptable carrier.

The invention provides for a method for modifying a TLR-stimulating oligonucleotide comprising an immune stimulatory oligonucleotide motif comprising incorporating chemical modifications into the immune stimulatory oligonucleotide motif and/or to the sequence flanking the immune stimulatory oligonucleotide motif, wherein the immune stimulatory activity of the immune stimulatory oligonucleotide motif is suppressed by the chemical modifications.

The invention further provides a method for inhibiting a TLR-mediated immune response in a vertebrate, the method comprising administering to the vertebrate an IRO compound in a pharmaceutically effective amount, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. In some preferred embodiments, inhibiting TLR stimulation comprising administering an IRO compound according to the invention, wherein the TLR is selected from TLR2, TLR3, TLR4, TLR5, TLR7, TLR8, and TLR9.

The invention further provides a method for inhibiting the activity of a TLR agonist comprising administering an IRO compound, wherein the IRO is administered at the same time, prior to or after the TLR agonist. In preferred embodiments the TLR agonist is selected from an agonist of TLR2, TLR3, TLR4, TLR5, TLR7, TLR8, and TLR9.

The invention further provides a method for therapeutically treating a vertebrate having a disease mediated by a TLR, such method comprising administering to the vertebrate an IRO compound according to the invention in a pharmaceutically effective amount. In preferred embodiments, the disease is cancer, an autoimmune disorder, airway inflammation, inflammatory disorders, infectious disease, skin disorders, allergy, asthma or a disease caused by a pathogen.

In some preferred embodiments, the IRO compound is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants or co-stimulatory molecules. In some preferred embodiments, the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

The invention further provides a method for preventing cancer, an autoimmune disorder, airway inflammation, inflammatory disorders, infectious disease, skin disorders, allergy, asthma or a disease caused by a pathogen in a vertebrate, such method comprising administering to the vertebrate an IRO compound according to the invention in a pharmaceutically effective amount. In some preferred embodiments, the IRO compound is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants or co-stimulatory molecules. In some preferred embodiments, the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

BRIEF DESCRIPTION OF THE DRAWINGS

FIGS. 4A-4D demonstrate that pre-administration and simultaneous administration of IRO can inhibit an agonist of TLR9 (SEQ ID NOS 3-5).

FIGS. 5A and 5B demonstrate that two CpG oligonucleotides linked at their 5' ends show TLR-inhibitory properties (SEQ ID NOS 3, 21, and 4).

DETAILED DESCRIPTION OF THE PREFERRED EMBODIMENTS

Figure 1:
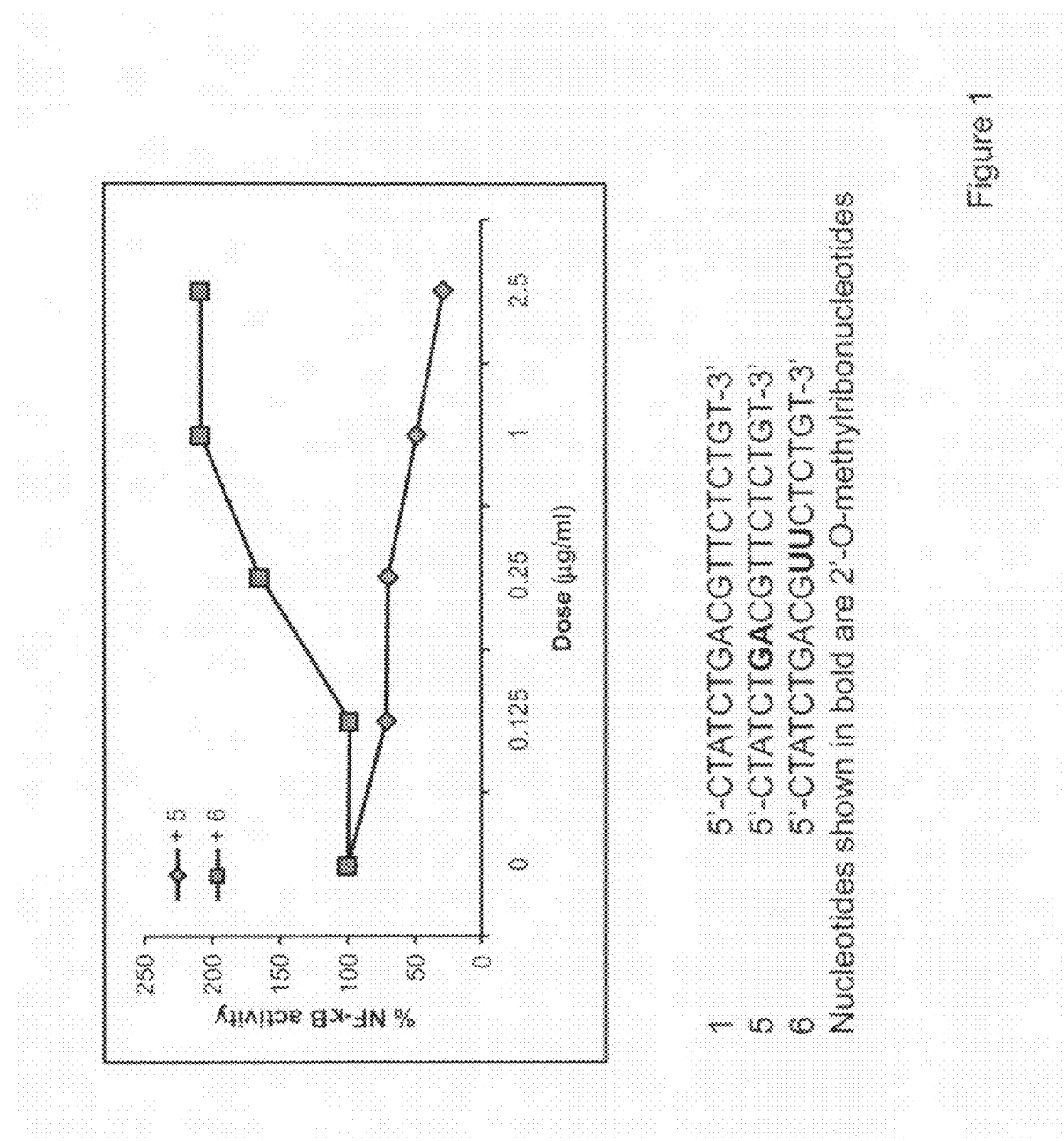
FIG. 1 demonstrates IRO inhibition of the TLR9 agonist activity of an IMO (SEQ ID NOS 1, 5, and 6).

The present invention relates to the therapeutic use of novel oligonucleotides as immune modulatory agents for immunotherapy applications. Specifically, the invention provides Immune Regulatory Oligonucleotide (IRO) compounds as antagonists of toll-like receptors (TLRs) to inhibit and/or suppress a TLR-mediated immune response. These IROs have unique sequences that inhibit or suppress TLR-mediated signaling in response to endogenous and/or exogenous TLR ligands or agonists. The references cited herein reflect the level of knowledge in the field and are hereby incorporated by reference in their entirety. Any conflicts between the teachings of the cited references and this specification shall be resolved in favor of the latter.

The invention provides methods for suppressing an immune response caused by TLRs and can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowl syndrome, sepsis, and bacteria, parasitic, and viral infections in adult and pediatric human and veterinary applications. Thus, the invention further provides IRO compounds having optimal levels of immune modulatory effect for immunotherapy and methods for making and using such compounds. In addition, IRO compounds of the invention are useful in combination with, for example, DNA vaccines, antigens, antibodies, and allergens; and in combination with chemotherapeutic agents (both traditional chemotherapy and modern targeted therapies) and/or antisense oligonucleotides for prevention and treatment of diseases.

DEFINITIONS

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann E et al. (1990) Chem. Rev. 90:543; "Protocols for Oligonucleotides and Analogs" Synthesis and Properties & Synthesis and Analytical Techniques, S. Agrawal, Ed, Humana Press, Totowa, USA 1993; and Hunziker, J. et al. (1995) Mod. Syn. Methods 7:331-417; and Crooke, S. et al. (1996) Ann. Rev. Pharm. Tox. 36:107-129. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-alkyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (downstream) from another region or position in the same polynucleotide or oligonucleotide.

The term "5'", when used directionally, generally refers to a region or position in a polynucleotide or oligonucleotide 5' (upstream) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist often mimics the action of a naturally occurring substance such as a ligand.

The term "antagonist" generally refers to a substance that attenuates the effects of an agonist.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

The term "allergy" generally refers to an inappropriate immune response characterized by inflammation and includes, without limitation, food allergies and respiratory allergies.

The term "antigen" generally refers to a substance that is recognized and selectively bound by an antibody or by a T cell antigen receptor, resulting in induction of an immune response. Antigens may include but are not limited to peptides, proteins, nucleosides, nucleotides, and combinations thereof. Antigens may be natural or synthetic and generally induce an immune response that is specific for that antigen.

The term "autoimmune disorder" generally refers to disorders in which "self" components undergo attack by the immune system.

The term "TLR-mediated disease" or TLR-mediated disorder" generally means any pathological condition for which activation of one or more TLRs is a contributing factor. Such conditions include but are not limited, cancer, an autoimmune disorder, airway inflammation, inflammatory disorders, infectious disease, skin disorders, allergy, asthma or a disease caused by a pathogen.

The term "physiologically acceptable" generally refers to a material that does not interfere with the effectiveness of an IRO compound and that is compatible with a biological system such as a cell, cell culture, tissue, or organism. Preferably, the biological system is a living organism, such as a vertebrate.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

The term "co-administration" generally refers to the administration of at least two different substances sufficiently close in time to modulate an immune response. Co-administration refers to simultaneous administration, as well as temporally spaced order of up to several days apart, of at least two different substances in any order, either in a single dose or separate doses.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term an "effective amount" or a "sufficient amount" generally refers to an amount sufficient to affect a desired biological effect, such as beneficial results. Thus, an "effective amount" or "sufficient amount" will depend upon the context in which it is being administered. In the context of administering a composition that modulates an immune response to a co-administered antigen, an effective amount of an IRO compound and antigen is an amount sufficient to achieve the desired modulation as compared to the immune response obtained when the antigen is administered alone. An effective amount may be administered in one or more administrations.

The term "in combination with" generally means in the course of treating a disease or disorder in a patient, administering an IRO compound and an agent useful for treating the disease or disorder that does not diminish the immune modulatory effect of the IRO compound. Such combination treatment may also include more than a single administration of an IRO compound and/or independently an agent. The administration of the IRO compound and/or the agent may be by the same or different routes.

The term "individual" or "subject" or "vertebrate" generally refers to a mammal, such as a human. Mammals generally include, but are not limited to, humans, non-human primates, rats, mice, cats, dogs, horses, cattle, cows, pigs, sheep, and rabbits.

The term "nucleoside" generally refers to compounds consisting of a sugar, usually ribose or deoxyribose, and a purine or pyrimidine base.

The term "nucleotide" generally refers to a nucleoside comprising a phosphate group attached to the sugar.

As used herein, the term "pyrimidine nucleoside" refers to a nucleoside wherein the base component of the nucleoside is a pyrimidine base (e.g., cytosine (C) or thymine (T) or Uracil (U)). Similarly, the term "purine nucleoside" refers to a nucleoside wherein the base component of the nucleoside is a purine base (e.g., adenine (A) or guanine (G)).

The terms "analog" or "derivative" can be used interchangeable to generally refer to any purine and/or pyrimidine nucleotide or nucleoside that has a modified base and/or sugar. A modified base is a base that is not guanine, cytosine, adenine, thymine or uracil. A modified sugar is any sugar that is not ribose or 2'deoxyribose and can be used in the backbone for an oligonucleotide.

The term "inhibiting" or "suppressing" generally refers to a decrease in a response or qualitative difference in a response, which could otherwise arise from eliciting and/or stimulation of a response.

The term "non-nucleotide linker" generally refers to any linkage or moiety that can link or be linked to the oligonucleotides other than through a phosphorous-containing linkage. Preferably such linker is from about 2 angstroms to about 200 angstroms in length.

The term "nucleotide linkage" generally refers to a direct 3'-5' linkage that directly connects the 3' and 5' hydroxyl groups of two nucleosides through a phosphorous-containing linkage.

The terms "oligonucleotide motif" means an oligonucleotide sequence, including a dinucleotide. An "oligonucleotide motif that would be immune stimulatory, but for one or more modifications" means an oligonucleotide motif which is immune stimulatory in a parent oligonucleotide, but not in a derivative oligonucleotide, wherein the derivative oligonucleotide is based upon the parent oligonucleotide, but has one or more modifications.

The terms CpG, C*pG, C*pG* and CpG* refer to oligonucleotide motifs that are immune stimulatory and comprise cytosine or a cytosine analog and a guanine or a guanine analog.

The term "treatment" generally refers to an approach intended to obtain a beneficial or desired results, which may include alleviation of symptoms, or delaying or ameliorating a disease progression.

In a first aspect, the invention provides an immune regulatory oligonucleotide (IRO) compound. The term "IRO" refers to an immune regulatory oligonucleotide compound that is an antagonist for one or more TLR, wherein the compound comprises an oligonucleotide motif and at least one modification, wherein the oligonucleotide motif would be immune stimulatory (e.g., unmethylated CpG), but for the one or more modifications that suppress the activity of the oligonucleotide motif, provided that compound contains less than 4 consecutive guanosine nucleotides and preferably less than 3 consecutive guanosine nucleotides. Such modifications may be in the oligonucleotide 5' terminus, in a sequence flanking the oligonucleotide motif, and/or within the oligonucleotide motif. These modifications result in an IRO compound that suppresses TLR-modulated immune stimulation. Such modifications can be to the bases, sugar residues and/or the phosphate backbone of the nucleotides/nucleosides flanking the oligonucleotide motif or within the oligonucleotide motif.

In preferred embodiments, when the modification is a 2' alkylation or alkoxylation then the modification is not 5' adjacent to the oligonucleotide motif; when the modification is a non-charged internucleoside linkage then the modification is not 5' adjacent to the oligonucleotide motif; and when the modification is a 3' alkylation or alkoxylation then the modification is not 5' or 3' adjacent to the oligonucleotide motif.

In preferred embodiments the IRO compound is not an antisense oligonucleotide.

The general structure of the IRO compounds may be represented as $5'-N_m-N_3N_2N_1CGN^1N^2N^3-N^m-3'$ wherein CG is an immune stimulatory motif and C is cytosine or a pyrimidine nucleotide derivative or non-nucleotide linker, and G is guanosine, a purine nucleotide derivative or non-nucleotide linker; N1-N3, at each occurrence, is independently a nucleotide, nucleotide derivative or non-nucleotide linker; Nm, at each occurrence, is independently a nucleotide, nucleotide derivative or non-nucleotide linker; provided that at least one N1 to N3 and/or C and/or G is a nucleotide derivative or non-nucleotide linker; and further provided that compound contains less than 4 consecutive guanosine nucleotides and preferably less than 3 consecutive guanosines, wherein the immune stimulatory activity of the CG is suppressed by the nucleotide derivative or non-nucleotide linker; and wherein m is a number from 0 to about 30.

In certain embodiments of the invention, IRO compounds may comprise at least two oligonucleotides covalently linked by a nucleotide linkage, or a non-nucleotide linker, at their 5'-, 3'- or 2'-ends or by functionalized sugar or by functionalized nucleobase via a non-nucleotide linker or a nucleotide linkage. Such IRO compounds may be linear or branched. As a non-limiting example, the linker may be attached to the 3'-hydroxyl. In such embodiments, the linker comprises a functional group, which is attached to the 3'-hydroxyl by means of a phosphate-based linkage like, for example, phosphodiester, phosphorothioate, phosphorodithioate, methylphosphonate, or by non-phosphate-based linkages. Possible sites of conjugation for the ribonucleotide are indicated in Formula I, below, wherein B represents a heterocyclic base and wherein the arrow pointing to P indicates any attachment to phosphorous.

Formula I

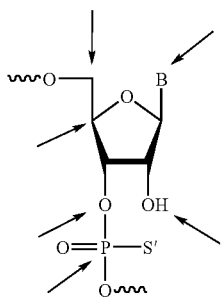

In some embodiments, the non-nucleotide linker is a small molecule, macromolecule or biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligoribonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the non-nucleotidic linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 3 to about 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, triethylene glycol hexaethylene glycol, polyethylene glycollinkers (e.g. [—O—CH2-CH2-]$_n$ (n=1-9)), methyl linkers, ethyl linkers, propyl linkers, butyl linkers, or hexyl linkers. In some embodiments, such alkyl linkers may include peptides or amino acids.

In some embodiments, the non-nucleotide linker may include, but are not limited to, those listed in Table 2.

TABLE 2

Representative Non-Nucleotidic Linkers

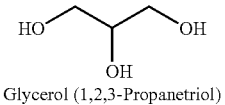
Glycerol (1,2,3-Propanetriol)

TABLE 2-continued

Representative Non-Nucleotidic Linkers

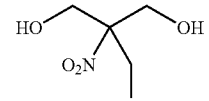
1,1,1-Tris(hydroxymethyl)nitromethane

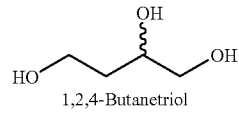
1,2,4-Butanetriol

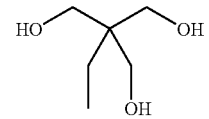
1,1,1-Tris(hydroxymethyl)propane

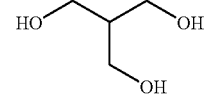
2-(hydroxymethyl)-1,3-propanediol

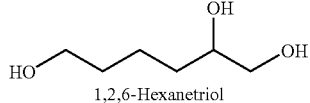
1,2,6-Hexanetriol

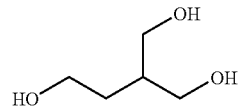
2-(hydroxymethyl)1,4-butanediol

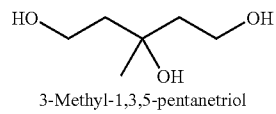
3-Methyl-1,3,5-pentanetriol

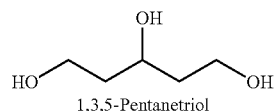
1,3,5-Pentanetriol

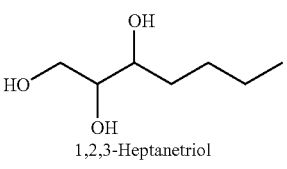
1,2,3-Heptanetriol

1,1,1-Tris(hydroxymethyl)ethane

2-Amino-2-(hydroxymethyl)-1,3-propanediol

TABLE 2-continued

Representative Non-Nucleotidic Linkers

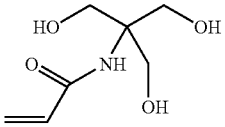
N-[Tris(hydroxymethyl)methyl]acrylamide

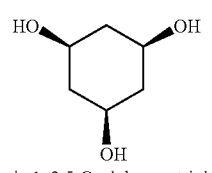
cis-1,3,5-Cyclohexanetriol

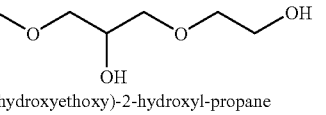
1,3-Di(hydroxyethoxy)-2-hydroxyl-propane

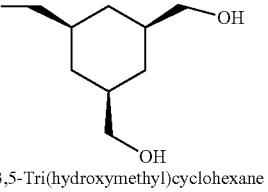
cis-1,3,5-Tri(hydroxymethyl)cyclohexane

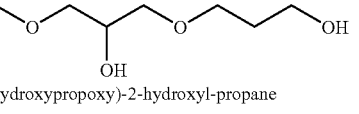
1,3-Di(hydroxypropoxy)-2-hydroxyl-propane

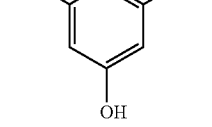
1,3,5,-Trihydroxyl-benzene

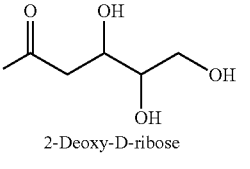
2-Deoxy-D-ribose

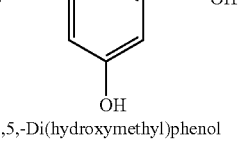
3,5,-Di(hydroxymethyl)phenol

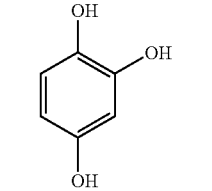
1,2,4,-Trihydroxyl-benzene

TABLE 2-continued

Representative Non-Nucleotidic Linkers

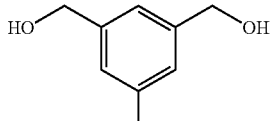
1,3,5,-Tri(hydroxymethyl)benzene

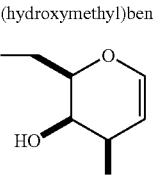
D-Galactoal

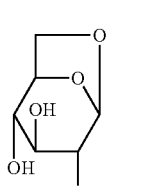
1,6-anhydro-β-D-Glucose

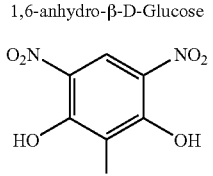
4,6-Nitropyrogallol

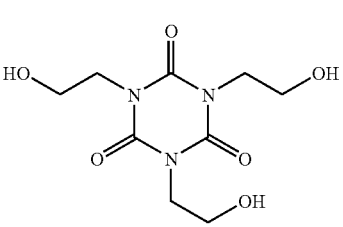 [SMILES: O=c1n(CCO)c(=O)n(CCO)c(=O)n1CCO]
1,3,5-Tris(2-hydroxyethyl)-Cyanuric acid

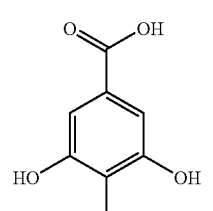
Gallic acid

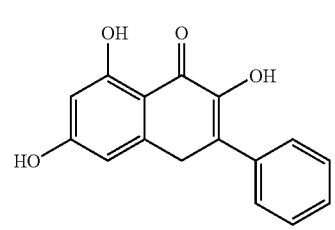 [SMILES: O=C1C(O)=C(c2ccccc2)Cc2cc(O)cc(O)c21]
3,5,7-Trihydroxyflavone

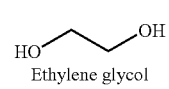
Ethylene glycol

TABLE 2-continued

Representative Non-Nucleotidic Linkers

1,5-Pentanediol

1,3-Propanediol

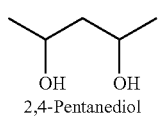
2,4-Pentanediol

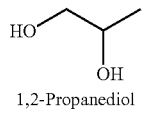
1,2-Propanediol

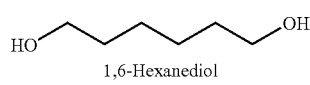
1,6-Hexanediol

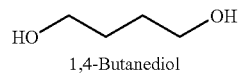
1,4-Butanediol

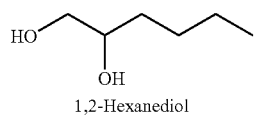
1,2-Hexanediol

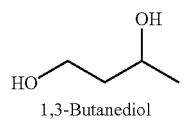
1,3-Butanediol

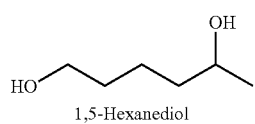
1,5-Hexanediol

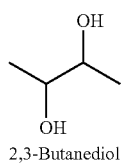
2,3-Butanediol

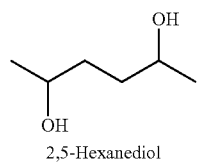
2,5-Hexanediol

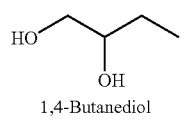
1,4-Butanediol

1,7-Heptanediol

TABLE 2-continued

Representative Non-Nucleotidic Linkers

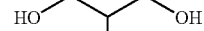
2-(1-Aminopropyl)-1,3-propanediol

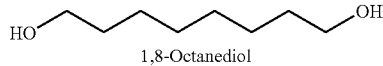
1,8-Octanediol

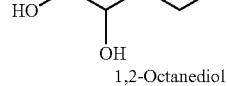
1,2-Octanediol

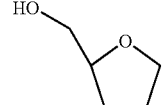
1,2-Dideoxyribose

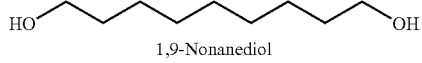
1,9-Nonanediol

1,12-Dodecanediol

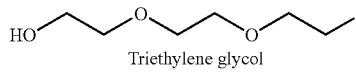
Triethylene glycol

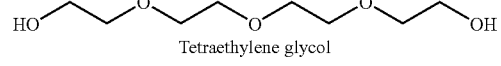
Tetraethylene glycol

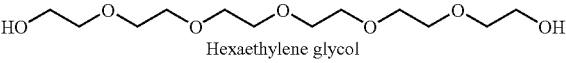
Hexaethylene glycol

In some embodiments, the small molecule linker is glycerol or a glycerol homolog of the formula HO—(CH$_2$)$_o$—CH(OH)—(CH$_2$)$_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH$_2$)$_m$—C(O)NH—CH$_2$—CH(OH)—CH$_2$—NHC(O)—(CH$_2$)$_m$—OH, wherein m is an integer from 0 to about 10, from 0 to about 6, from 2 to about 6, or from 2 to about 4

Some non-nucleotide linkers according to the invention permit attachment of more than two oligonucleotides. For example, the small molecule linker glycerol has three hydroxyl groups to which oligonucleotides may be covalently attached. Some IROs according to the invention, therefore, comprise two or more oligonucleotides linked to a nucleotide or a non-nucleotide linker. Such IROs are referred to as being "branched".

IRO compounds may comprise at least two oligonucleotides non-covalently linked, such as by electrostatic interactions, hydrophobic interactions, π-stacking interactions, hydrogen bonding and combinations thereof. Non-limiting examples of such non-covalent linkage includes Watson-Crick base pairing, Hoogsteen base pairing and base stacking.

Some of the ways in which two or more oligonucleotides can be linked are shown in Table 3.

TABLE 3

Oligoribonucleotide Formulas IV-XI

In certain embodiments, pyrimidine nucleosides in the immune regulatory oligonucleotides used in the compositions and methods according to the invention have the structure (II):

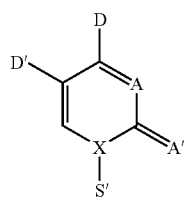

wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a sugar analog.

In certain embodiments, the sugar ring is derivatized with a phosphate moiety, modified phosphate moiety, or other linker moiety suitable for linking the pyrimidine nucleoside to another nucleoside or nucleoside analog.

In some embodiments hydrogen bond donors include, without limitation, —NH—, —NH$_2$, —SH and —OH. Preferred hydrogen bond acceptors include, without limitation, C═O, C═S, and the ring nitrogen atoms of an aromatic heterocycle, e.g., N3 of cytosine.

In some embodiments, (II) is a pyrimidine nucleoside derivative. Examples of pyrimidine nucleoside derivatives include, without limitation, 5-hydroxycytosine, 5-hydroxymethylcytosine, N4-alkylcytosine, or N4-ethylcytosine, araC, 5-OH-dC, N3-Me-dC, and 4-thiouracil. Chemical modified derivatives also include, but are not limited to, thymine or uracil analogues. In some embodiments, the sugar moiety S' in (II) is a sugar derivative. Suitable sugar derivatives include, but are not limited to, trehalose or trehalose derivatives, hexose or hexose derivatives, arabinose or arabinose derivatives.

In some embodiments, the purine nucleosides in immune regulatory oligonucleotides used in the compositions and methods according to the invention have the structure (III):

(III)

wherein:

D is a hydrogen bond donor;

D' is selected from the group consisting of hydrogen, hydrogen bond donor, and hydrophilic group;

A is a hydrogen bond acceptor or a hydrophilic group;

X is carbon or nitrogen;

each L is independently selected from the group consisting of C, O, N and S; and S' is a pentose or hexose sugar ring, or a sugar analog.

In certain embodiments, the sugar ring is derivatized with a phosphate moiety, modified phosphate moiety, or other linker moiety suitable for linking the pyrimidine nucleoside to another nucleoside or nucleoside analog.

In certain embodiments hydrogen bond donors include, without limitation, —NH—, —NH$_2$, —SH and —OH. In certain embodiments hydrogen bond acceptors include, without limitation, C═O, C═S, —NO$_2$ and the ring nitrogen atoms of an aromatic heterocycle, e.g., N1 of guanine.

In some embodiments, (III) is a purine nucleoside derivative. Examples of purine nucleoside derivatives include, without limitation, guanine analogues such as 7-deaza-G, 7-deaza-dG, ara-G, 6-thio-G, Inosine, Iso-G, loxoribine, TOG(7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino)guanosine, 7-Methyl-6-thioguanosine, 8-Benzyloxyguanosine, 9-Deazaguanosine, 1-(B-D-ribofuranosyl)-2-oxo-7-deaza-8-methyl-purine, 1-(2'-deoxy-β-D-ribofuranosyl)-2-oxo-7-deaza-8-methyl-purine. Chemically modified derivatives also include, but are not limited to, adenine analogues such as 9-benzyl-8-hydroxy-2-(2-methoxyethoxy)adenine, 2-Amino-N2-O—, methyladenosine, 8-Aza-7-deaza-A, 7-deaza-A, Vidarabine, 2-Aminoadenosine, N1-Methyladenosine, 8-Azaadenosine, 5-Iodotubercidin, and N1-Me-dG. In some embodiments, the sugar moiety S' in (III) is a sugar derivative as defined for Formula II.

In certain embodiments of the invention, the immune regulatory nucleic acid comprises a nucleic acid sequence containing at least one B-L-deoxy nucleoside or 3'-deoxy nucleoside.

In certain embodiments of the invention, the immune regulatory oligonucleotide comprises a nucleic acid sequence containing at least one dinucleotide selected from CpG, C*pG, C*pG* and CpG*, wherein C is cytosine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate, and wherein the activity of the at least one dinucleotide is regulated by the flanking sequence.

The sequences of specific IRO within these general structures used in the present study include, but are not limited to, those shown in Table 4.

TABLE 4

| IRO | Sequence (SEQ ID NO:) |
|---|---|
| 5 | 5'-CTATCT<u>GA</u>CGTTCTCTGT-3' (SEQ ID NO: 5) |
| 7 | 5'-CTATCT<u>GA</u>CGTTCTCTGT-3' (SEQ ID NO: 7) |
| 17 | 5'-CTATCT<u>GA</u>CG$_1$TTCTCTGT-3' (SEQ ID NO: 17) |
| 37 | 5'-CTATCT<u>GA</u>CG$_4$TTCTCTGT-3' (SEQ ID NO: 37) |
| 39 | 5'-CTATCT<u>GA</u>C$_4$GTTCTCTGT-3' (SEQ ID NO: 39) |
| 41 | 5'-CTATCT<u>GA</u>C$_5$GTTCTCTGT-3' (SEQ ID NO: 41) |
| 43 | 5'-CTATCT<u>GA</u>C$_6$GTTCTCTGT-3' (SEQ ID NO: 43) |
| 45 | 5'-CTATCT<u>GA</u>CG$_5$TTCTCTGT-3' (SEQ ID NO: 45) |
| 47 | 5'-CTATCT<u>GA</u>C$_7$GTTCTCTGT-3' (SEQ ID NO: 47) |
| 64 | 5'-CTATCT<u>AA</u>CGTTCTCTGT-3' (SEQ ID NO: 64) |
| 67 | 5'-CTATCT<u>AA</u>CG$_1$TTCTCTGT-3' (SEQ ID NO: 67) |
| 22 | 5'-CTATCTGAmCGTTCTCTGT-3' (SEQ ID NO: 22) |
| 9 | 5'-CTATCTG<u>U</u>CGTTCTCTGT-3' (SEQ ID NO: 9) |
| 10 | 5'-CTATCTG<u>U</u>CGTTCTCTGT-3' (SEQ ID NO: 10) |
| 19 | 5'-CTATCTG<u>U</u>CG$_1$TTCTCTGT-3' (SEQ ID NO: 19) |
| 38 | 5'-CTATCTG<u>U</u>CG$_4$TTCTCTGT-3' (SEQ ID NO: 38) |
| 40 | 5'-CTATCTG<u>U</u>C$_4$GTTCTCTGT-3' (SEQ ID NO: 40) |
| 42 | 5'-CTATCTG<u>U</u>C$_5$GTTCTCTGT-3' (SEQ ID NO: 42) |
| 44 | 5'-CTATCTG<u>U</u>C$_6$GTTCTCTGT-3' (SEQ ID NO: 44) |
| 46 | 5'-CTATCTG<u>U</u>CG$_5$TTCTCTGT-3' (SEQ ID NO: 46) |
| 48 | 5'-CTATCTG<u>U</u>C$_7$GTTCTCTGT-3' (SEQ ID NO: 48) |
| 66 | 5'-CTATCT<u>AU</u>CGTTCTCTGT-3' (SEQ ID NO: 66) |
| 69 | 5'-CTATCT<u>AU</u>CG$_1$TTCTCTGT-3' (SEQ ID NO: 69) |
| 65 | 5'-CTATCT<u>AG</u>CGTTCTCTGT-3' (SEQ ID NO: 65) |
| 68 | 5'-CTATCT<u>AG</u>CG$_1$TTCTCTGT-3' (SEQ ID NO: 68) |
| 23 | 5'-CTATCTGmACGTTCTCTGT-3' (SEQ ID NO: 23) |
| 24 | 5'-CTATCTGmAmCGTTCTCTGT-3' (SEQ ID NO: 24) |
| 25 | 5'-CTATCTGAC$_2$GTTCTCTGT-3' (SEQ ID NO: 25) |
| 27 | 5'-CTATCTGTC$_2$GTTCTCTGT-3' (SEQ ID NO: 27) |
| 33 | 5'-CTATCTGAC$_3$GTTCTCTGT-3' (SEQ ID NO: 33) |
| 35 | 5'-CTATCTGTC$_3$GTTCTCTGT-3' (SEQ ID NO: 35) |
| 26 | 5'-CTATCTGACG$_2$TTCTCTGT-3' (SEQ ID NO: 26) |
| 28 | 5'-CTATCTGTCG$_2$TTCTCTGT-3' (SEQ ID NO: 28) |
| 34 | 5'-CTATCTGACG$_3$TTCTCTGT-3' (SEQ ID NO: 34) |

TABLE 4-continued

| IRO | Sequence (SEQ ID NO:) |
|---|---|
| 36 | 5'-CTATCTGTCG$_3$TTCTCTGT-3' (SEQ ID NO: 36) |
| 49 | 5'-CTATCTAGCGT<u>T</u>CTCTGT-3' (SEQ ID NO: 49) |
| 50 | 5'-CTATCTAGCGT<u>T</u>CTCTGT-3' (SEQ ID NO: 50) |
| 6 | 5'-CTATCTGACG<u>UU</u>CTCTGT-3' (SEQ ID NO: 6) |
| 51 | 5'-CTATCTAGCG<u>TT</u>CTCTGT-3' (SEQ ID NO: 51) |
| 21 and 21 | 5'-TCTTGCAGTCT-X$_2$-TCTGACGTTCT-3' (5'-SEQ ID NO: 21-3'-X$_2$-3'-SEQ ID NO: 21-5') |
| 52 | 5'-CCTACTAGCGTX$_1$CTCATC-3' (SEQ ID NO: 52) |
| 53 | 5'-CCTACTAGCGX$_1$TCTCATC-3' (SEQ ID NO: 53) |
| 54 | 5'-CCTACTAG$_3$CGTTCTCATC-3' (SEQ ID NO: 54) |
| 55 | 5'-TCCATGA$_1$CGTTCCTGATGC-3' (SEQ ID NO: 55) |
| 56 | 5'-CTATCTGAC$_2$G$_2$TTCTCTGT-3' (SEQ ID NO: 56) |
| 57 | 5'-C$_2$T$_2$A$_2$T$_2$C$_2$T$_2$G$_2$A$_2$C$_2$G$_2$T$_2$T$_2$C$_2$T$_2$G$_2$T$_2$-3' (SEQ ID NO: 57) |
| 29 | 5'-CTATCTGAX$_1$GTTCTCTGT-3' (SEQ ID NO: 29) |
| 30 | 5'-CTATCTGACX$_1$TTCTCTGT-3' (SEQ ID NO: 30) |
| 31 | 5'-CTATCTGTX$_1$GTTCTCTGT-3' (SEQ ID NO: 31) |
| 32 | 5'-CTATCTGTCX$_1$TTCTCTGT-3' (SEQ ID NO: 32) |
| 61 | 5'-CTATCTAGCGTX$_1$CTCTGT-3' (SEQ ID NO: 61) |
| 62 | 5'-CTATCTAGCGX$_1$TCTCTGT-3' (SEQ ID NO: 62) |
| 63 | 5'-CTATCTAGCGX$_1$X$_1$CTCTGT-3' (SEQ ID NO: 63) |
| 58 | 5'-CTATCTGACGTX$_3$CTCTGT-3' (SEQ ID NO: 58) |
| 59 | 5'-CTATCTGACGX$_3$TCTCTGT-3' (SEQ ID NO: 59) |
| 60 | 5'-CTATCTGACGX$_3$X$_3$CTCTGT-3' (SEQ ID NO: 60) |
| 70 | 5'-CTATCTAGCGTX$_3$CTCTGT-3' (SEQ ID NO: 70) |
| 71 | 5'-CTATCTAGCGX$_3$TCTCTGT-3' (SEQ ID NO: 71) |
| 72 | 5'-CTATCTAGCGX$_3$X$_3$CTCTGT-3' (SEQ ID NO: 72) |
| 74 | 5'-CTATCT<u>GA</u>CGTTCTCTGT-3' (SEQ ID NO: 74) |
| 75 | 5'-CTATCTGACG$_1$<u>UU</u>CTCTGT-3' (SEQ ID NO: 75) |
| 76 | 5'-CCTACTAG$_6$CGTTCTCATC-3' (SEQ ID NO: 76) |
| 77 | 5'-TCCATGACGU$_1$TCCTGATGC-3' (SEQ ID NO: 77) |
| 78 | 5'-CTATCTGX$_2$CGTTCTCTGT-3' (SEQ ID NO: 78) |
| 79 | 5'-CTATCTX$_2$ACGTTCTCTGT-3' (SEQ ID NO: 79) |
| 80 | 5'-CTATCTU$_2$ACGTTCTCTGT-3' (SEQ ID NO: 80) |
| 81 | 5'-CTATCTGU$_2$CGTTCTCTGT-3' (SEQ ID NO: 81) |
| 82 | 5'-CTATCTGACGX$_2$TCTCTGT-3' (SEQ ID NO: 82) |
| 83 | 5'-CTATCTGACGTX$_2$CTCTGT-3' (SEQ ID NO: 83) |
| 84 | 5'-CTATCTGX$_3$CGTTCTCTGT-3' (SEQ ID NO: 84) |
| 85 | 5'-CTATCTX3ACGTTCTCTGT-3' (SEQ ID NO: 85) |
| 86 | 5'-(TCT<u>GA</u>CGTTCT)$_2$X$_2$ (5'-SEQ ID NO: 86-3'-X$_2$-3'-SEQ ID NO: 86-5') |
| 87 | 5'-(TCT<u>GA</u>CG$_1$TTCT)$_2$X$_2$ (5'-SEQ ID NO: 87-3'-X$_2$-3'-SEQ ID NO: 87-5') |
| 88 | 5'-(TCT<u>GA</u>CG$_4$TTCT)$_2$X$_2$ (5'-SEQ ID NO: 88-3'-X$_2$-3'-SEQ ID NO: 88-5') |
| 89 | 5'-(TCTCT<u>GA</u>CGTT)$_2$X$_2$ (5'-SEQ ID NO: 89-3'-X$_2$-3'-SEQ ID NO: 89-5') |
| 90 and 8 | 5'-TCT<u>GA</u>CG$_1$TTCT-X$_3$-TGACCGGTCA-3' (5'-SEQ ID NO: 90-3'-X$_2$-3'-SEQ ID NO: 8-5') |
| 91 | 5'-CTATCTGTCG<u>UU</u>CTCTGT-3' (SEQ ID NO: 91) |
| 92 | 5'-CTATCTGTCG$_1$<u>UU</u>CTCTGT-3' (SEQ ID NO: 92) |
| 93 | 5'-(TCT<u>GU</u>CGTTCT)$_2$X$_2$ (5'-SEQ ID NO: 93-3'-X$_2$-3'-SEQ ID NO: 93-5') |
| 94 | 5'-(TCT<u>GU</u>CG$_1$TTCT)$_2$X$_2$ (5'-SEQ ID NO: 94-3'-X$_2$-3'-SEQ ID NO: 94-5') |
| 95 | 5'-(TCT<u>GA</u>CG$_4$TTCT)X$_2$ (5'-SEQ ID NO: 95-3'-X$_2$-3'-SEQ ID NO: 95-5') |
| 96 | 5'-(TCT<u>GA</u>CG$_1$TT)$_2$X$_2$ (5'-SEQ ID NO: 96-3'-X$_2$-3'-SEQ ID NO: 96-5') |
| 97 and 11 | 5'-TCT<u>GA</u>CG$_1$TTCT-X$_3$-TCAACCACACA-3' (5'-SEQ ID NO: 97-3'-X$_2$-3'-SEQ ID NO: 11-5') |

TABLE 4-continued

| IRO | Sequence (SEQ ID NO:) |
|---|---|
| 98 | 5'-CTATCT<u>GA</u>CG₁TTCT<u>CUGU</u>-3'<br>(SEQ ID NO: 98) |
| 99 | 5'-CTATCT<u>GU</u>CG₁TTCT<u>CUGU</u>-3'<br>(SEQ ID NO: 99) |
| 100 | 5'-(<u>UGUCG</u>₁TTCT)X₂<br>(5'-SEQ ID NO: 100-3'-X₂-3'-SEQ ID NO: 100-5') |
| 101 | 5'-(<u>UGA</u>CG<sub>j</sub>TTCT)₂X₂<br>(5'-SEQ ID NO: 101-3'-X₂-3'-SEQ ID NO: 101-5') |

Underlined G, A or U = 2'-OMe; Underlined T = 3'-OMe; $A_1$ = 3'-OMe; $G_1$ = 7-deaza-dG; m = P-Me; $A_2$, $T_2$, $C_2$, and $G_2$ = β-L-deoxy nucleoside; $X_1$ = abasic; $X_2$ = glycerol linker; $X_3$ = C3-linker; $C_3$ and $G_3$ = 3'-deoxy-nucleoside; $G_4$ = araG; $C_4$ = araC; $C_5$ = 5-OH-dC; $C_6$ = 1-(2'-deoxy-β-D-ribofuranosyl)-2-oxo-7-deaza-8-methyl-purine; $G_5$ = N1-Me-dG; $C_7$ = N3-Me-dC; $U_1$ = 3'-OMe; $U_2$ = dU; IROs in which two copies of a nucleotide sequence are linked by a linker X are indicated using parentheses, e.g., 5'-(TCTGACGT-TCT)₂X₂ represents an IRO in which two copies of the nucleotide sequence 5'-TCTGACGTTCT-3' (SEQ ID NO: 86) are linked by a linker $X_2$.

In some embodiments, the oligonucleotides each have from about 6 to about 35 nucleoside residues, preferably from about 9 to about 30 nucleoside residues, more preferably from about 11 to about 23 nucleoside residues. In some embodiments, the oligonucleotides have from about 6 to about 18.

In a second aspect, the invention provides pharmaceutical formulations comprising an IRO compound according to the invention and a physiologically acceptable carrier.

In a third aspect, the invention provides methods for inhibiting or suppressing TLR-mediated induction of an immune response in a vertebrate, such methods comprising administering to the vertebrate a IRO compound according to the invention. In some embodiments, the vertebrate is a mammal. In preferred embodiments, IRO compound is administered to a vertebrate in need of immune suppression.

According to this aspect of the invention, an IRO compound is capable of suppressing a TLR-based immune response to a further TLR ligand or TLR agonist. As discussed further in the Examples below, the activation of a TLR-based immune response by a TLR agonist or TLR ligand (e.g. an immune modulatory oligonucleotide) can be suppressed/inhibited by the simultaneous, pre- or post-administration of an IRO compound, and such suppression/inhibition may be maintained for an extended period of time (e.g. days) after administration. This beneficial property of the current invention has a unique advantage for the prevention and/or treatment of a disease or disorder. For example, application of certain TLR-agonists in the course of treating the disease may cause unwanted immune stimulation that an IRO compound could suppress/inhibit. Administration of the IRO simultaneously, pre and/or post administration of the TLR-agonist may allow therapeutic benefits from the TLR-agonist while suppressing/inhibiting the unwanted side effect(s). Additionally, pre-administration of an IRO could prevent an immune response (e.g., allergic reaction) to a subsequent or later challenge by a TLR-agonist.

In the methods according to this aspect of the invention, administration of IRO compound can be by any suitable route, including, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form. Administration of the therapeutic compositions of IRO compound can be carried out using known procedures at dosages and for periods of time effective to reduce symptoms or surrogate markers of the disease. When administered systemically, the therapeutic composition is preferably administered at a sufficient dosage to attain a blood level of IRO compound from about 0.0001 micromolar to about 10 micromolar. For localized administration, much lower concentrations than this may be effective, and much higher concentrations may be tolerated. Preferably, a total dosage of IRO compound ranges from about 0.001 mg per patient per day to about 200 mg per kg body weight per day. It may be desirable to administer simultaneously, or sequentially a therapeutically effective amount of one or more of the therapeutic compositions of the invention to an individual as a single treatment episode.

The IRO compound may optionally be linked to one or more allergens and/or antigens (self or foreign), an immunogenic protein, such as keyhole limpet hemocyanin (KLH), cholera toxin B subunit, or any other immunogenic carrier protein. IRO can also be used in combination with other compounds (e.g. adjuvants) including, without limitation, TLR agonists (e.g. TLR2 agonists and TLR9 agonists), Freund's incomplete adjuvant, KLH, monophosphoryl lipid A (MPL), alum, and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric and veterinary vaccine applications.

In a fourth aspect, the invention provides methods for therapeutically treating a patient having a disease or disorder, such methods comprising administering to the patient a IRO compound according to the invention. In various embodiments, the disease or disorder to be treated is cancer, an autoimmune disorder, infectious disease, airway inflammation, inflammatory disorders, allergy, asthma, or a disease caused by a pathogen. Pathogens include bacteria, parasites, fungi, viruses, viroids, and prions. Administration is carried out as described for the third aspect of the invention.

In a fifth aspect, the invention provides methods for preventing a disease or disorder, such methods comprising administering to the patient IRO compound according to the invention. In various embodiments, the disease or disorder to be prevented is cancer, an autoimmune disorder, airway inflammation, inflammatory disorders, infectious disease, allergy, asthma, or a disease caused by a pathogen. Pathogens include bacteria, parasites, fungi, viruses, viroids, and prions. Administration is carried out as described for the third aspect of the invention.

In any of the methods according to this aspect of the invention, the IRO compound can be administered in combination with any other agent useful for treating the disease or condition that does not diminish the immune modulatory effect of the IRO compound. In any of the methods according to the invention, the agent useful for treating the disease or condition includes, but is not limited to, one or more vaccines, antigens, antibodies, cytotoxic agents, allergens, antibiotics, antisense oligonucleotides, TLR agonist, TLR antagonist, peptides, proteins, gene therapy vectors, DNA vaccines and/or adjuvants to enhance the specificity or magnitude of the immune response, or co-stimulatory molecules such as cytokines, chemokines, protein ligands, trans-activating factors, peptides and peptides comprising modified amino acids. For example, in the treatment of cancer, it is contemplated that the IRO compound may be administered in combination with one or more chemotherapeutic compound, targeted therapeutic agent and/or monoclonal antibody. Alternatively, the agent can include DNA vectors encoding for antigen or allergen. In these embodiments, the IRO compounds of the invention can variously act as adjuvants and/or produce direct immune modulatory effects.

The following examples are intended to further illustrate certain exemplary embodiments of the invention and are not intended to limit the scope of the invention. For example, representative TLR-ligands are shown in the following examples, but do not limit the scope of ligands to which the IROs of the invention act as antagonists.

Example 1

Synthesis of Oligonucleotides Containing Immune Regulatory Moieties

All IRO were synthesized according to standard procedures (see e.g. U.S. Patent Publication No. 20040097719).

Oligonucleotides were synthesized on a 1 μM scale using an automated DNA synthesizer (Expedite 8909; PerSeptive Biosystems, Framingham, Mass.), following standard linear synthesis or parallel synthesis procedures (see e.g. FIGS. 5 and 6 of U.S. Patent Publication No. 20040097719).

Deoxyribonucleoside phosphoramidites were obtained from (Aldrich-Sigma, St Louis, Mo.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosphonamidite were obtained from Glen Research (Sterling, Va.). .beta.-L-2'-deoxyribonucleoside phosphoramidite, .alpha.-2'-deoxyribonucleoside phosphoramidite, mono-DMT-glycerol phosphoramidite and di-DMT-glycerol phosphoramidite were obtained from ChemGenes (Willmington, Mass.). (4-Aminobutyl)-1,3-propanediol phosphoramidite was obtained from Clontech (Palo Alto, Calif.). Arabinocytidine phosphoramidite, arabinoguanosine, arabinothymidine and arabinouridine were obtained from Reliable Pharmaceutical (St. Louis, Mo.). Arabinoguanosine phosphoramidite, arabinothymidine phosphoramidite and arabinouridine phosphoramidite were synthesized at Idera Pharmaceuticals, Inc. (Cambridge, Mass.) (Noronha et al. (2000) Biochem., 39:7050-7062).

All nucleoside phosphoramidites were characterized by $^{31}$P and $^{1}$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Inhibition of TLR9 Stimulation

HEK293 cells stably expressing TLR9 (Invivogen) were transiently transfected with reporter gene, Seap, (Invivogen) for 6 hr. Cells were treated with 0.5 μg/ml 5'-CTATCT-GACGTTCTCTGT-3' (mouse CpG sequence; IMO/SEQ ID NO 1; 0 dose) alone and various concentrations of IRO 5 or 6 for 18 hr. TLR9-dependent reporter gene expression was determined according to the manufacturer's protocol (Invivogen) and the results are expressed as % activity of TLR9 stimulating oligonucleotide (100%). The results are shown in FIG. 1. These results demonstrate that IRO 5 inhibited TLR9 agonistic activity of IMO.

Example 3

IRO Specifically Inhibit TLR9 Stimulation

Figure 2:
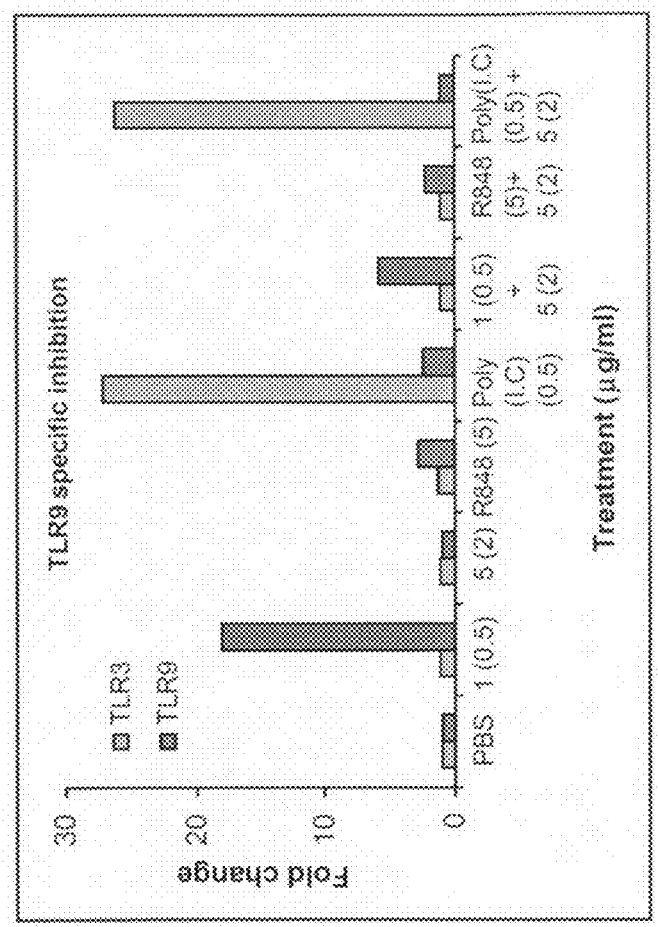
FIG. 2 demonstrates the specificity of one IRO compound as an antagonist of TLR9 vs TLR3 (SEQ ID NOS 1 and 5).

HEK293 cells stably expressing TLR9 or TLR3 (Invivogen) were transiently transfected with reporter gene, Seap, (Invivogen) for 6 hr. Cells were treated with 0.5 mg/ml IMO 1 (0.5 μg/ml), IRO 5 (2.0 μg/ml), R848 (5.0 μg/ml), or poly (I).poly(C) (0.5 μg/ml) and combinations of IMO+IRO, R848+IRO, or poly(I).poly(C)+IRO for 18 hr. TLR9- or TLR3-dependent reporter gene expression was determined according to the manufacturer's protocol (Invivogen) and the results are expressed as fold change in NF-kB activity. The results are shown in FIG. 2. These results demonstrate that IRO 5 inhibits the activity of the TLR9 agonist but not agonist of TLR3, and more generally that IRO's can selectively inhibit TLR activation.

Example 4

Dose-Dependent Inhibition by IRO

Figure 3:
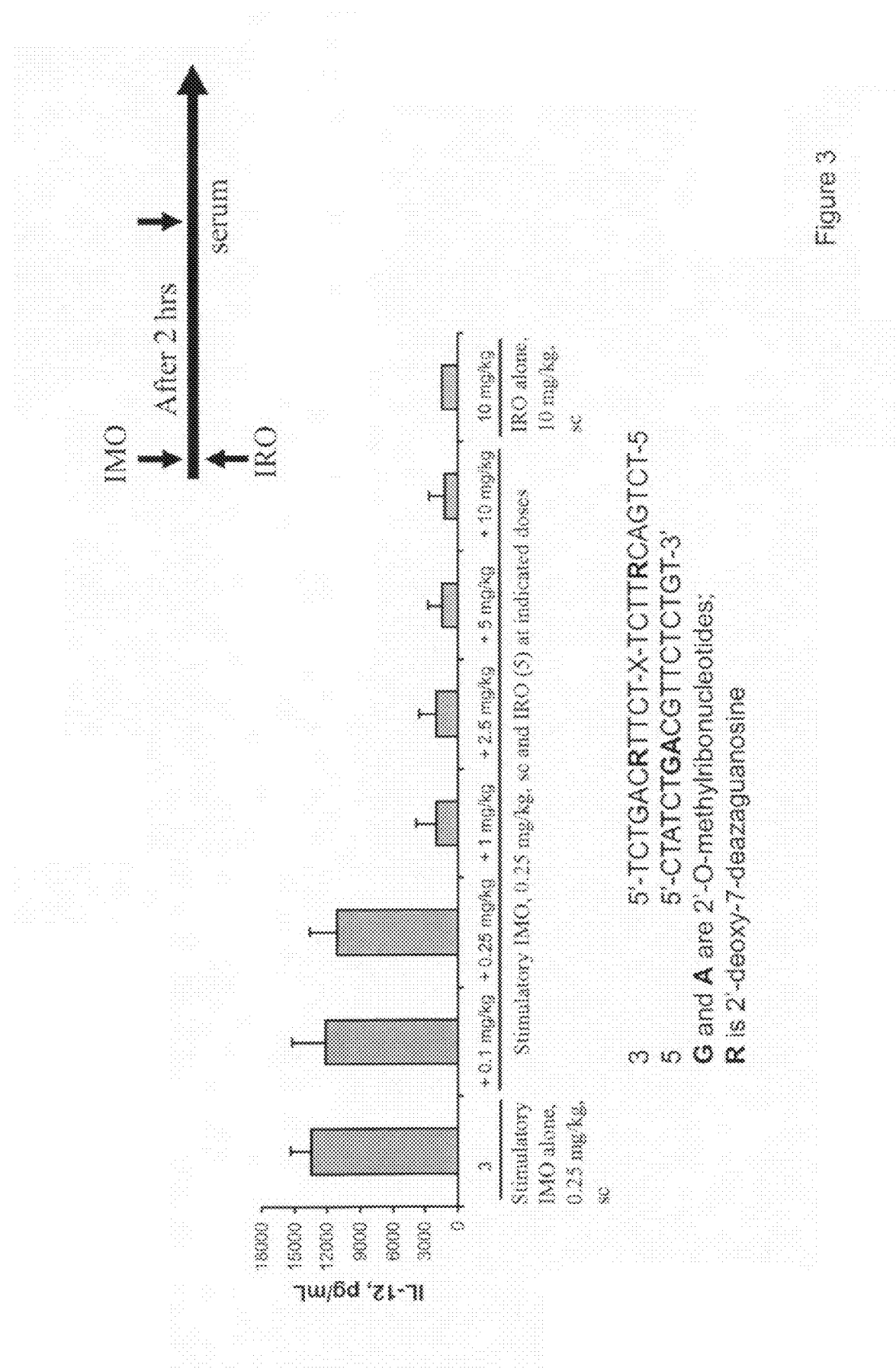
FIG. 3 demonstrates dose-dependent inhibition by an IRO (SEQ ID NOS 3 and 5).

C57BL/6 mice were injected subcutaneously (s.c.) at left underarm with 0.25 mg/kg stimulating 5'-TCTGACG$_1$TTCT-X-TCTTG$_1$CAGTCT-5' (IMO/SEQ ID NO 3; G$_1$=7-deazaG, X=glycerol) and different doses of IRO 5 at right under arm. Serum samples were taken at 2 hours after stimulating IMO 3 injection and determined IL-12 levels by ELISA. The results are shown in FIG. 3. These results demonstrate dose-dependent inhibition by IRO.

Example 5

Time-Dependence Inhibition by IRO

Figure 4A:
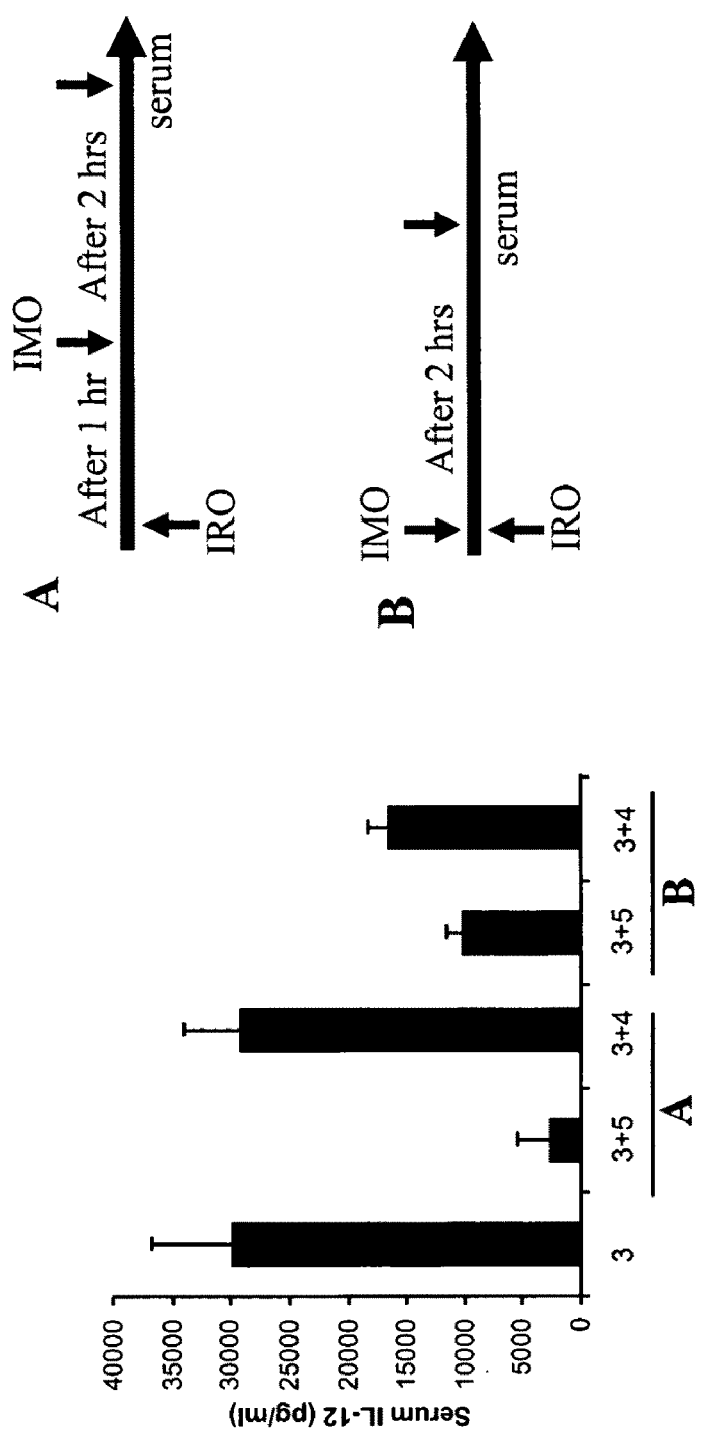

C57BL/6 mice were injected s.c. at left underarm with 0.25 mg/kg stimulating IMO 3 and 1 mg/kg IRO 5 or 5'-CTATCT-CACCTTCTCTGT-5' (non-CpG non-stimulatory control; oligo/SEQ ID NO 4) at right under arm either one hour before (−1 h) or at the same time as stimulating IMO (Oh). Serum samples were taken at 2 hours after stimulating IMO injection and determined IL-12 levels by ELISA. The results in FIG. 4A demonstrate a decrease in serum IL-12 levels after administration of IRO 5 or (oligo 4) either one hour before (−1 h) or at the same time as stimulating IMO (Oh).

C57BL/6 mice were injected s.c. at left underarm with 0.25 mg/kg stimulating IMO 3 and intranasal administration of 10 mg/kg IRO 102 at the same time as stimulating IMO (Oh). Serum samples were taken at 2 hours after stimulating IMO injection and determined IL-12 levels by ELISA. The results in FIG. 4B demonstrate a decrease in serum IL-12 levels after intranasal administration of IRO 102 at the same time as s.c. of IMO.

C57BL/6 mice were injected s.c at left underarm with 0.25 mg/kg stimulating IMO 3 and 2 mg/kg or 10 mg/kg IRO 17, 99, 102 s.c. at right under arm either one hour before (−1 h), twenty-four hours before (−24) or seventy-two hours before (−72) as stimulating IMO (Oh). Serum samples were taken at 2 hours after stimulating IMO injection and determined IL-12 levels by ELISA. The results are shown in FIG. 4C-D. These results demonstrate pre-administration and simultaneous administration of IRO was able to inhibit agonist of TLR9, and more generally that IRO's can inhibit TLR activation.

Example 6

Inhibition of TLR9 Stimulation

C57BL/6 mice were injected s.c. at left underarm with 0.25 mg/kg stimulating IMO 3 and 1 mg/kg IRO 21 or control oligo 4 at right under arm either one hour before (−1 h) or at the same time as stimulating IMO (Oh). Serum samples were taken at 2 hours after stimulating IMO injection and determined IL-12 levels by ELISA. The results are shown in FIGS. 5A and 5B. These results demonstrate that a CpG oligonucleotide linked at its 5' ends show inhibitory properties, and more generally that immune stimulatory CpG oligonucleotides linked at their 5' ends can inhibit TLR activation.

Example 7

Inhibition of TLR9 in Human Cell Cultures

Figure 6:
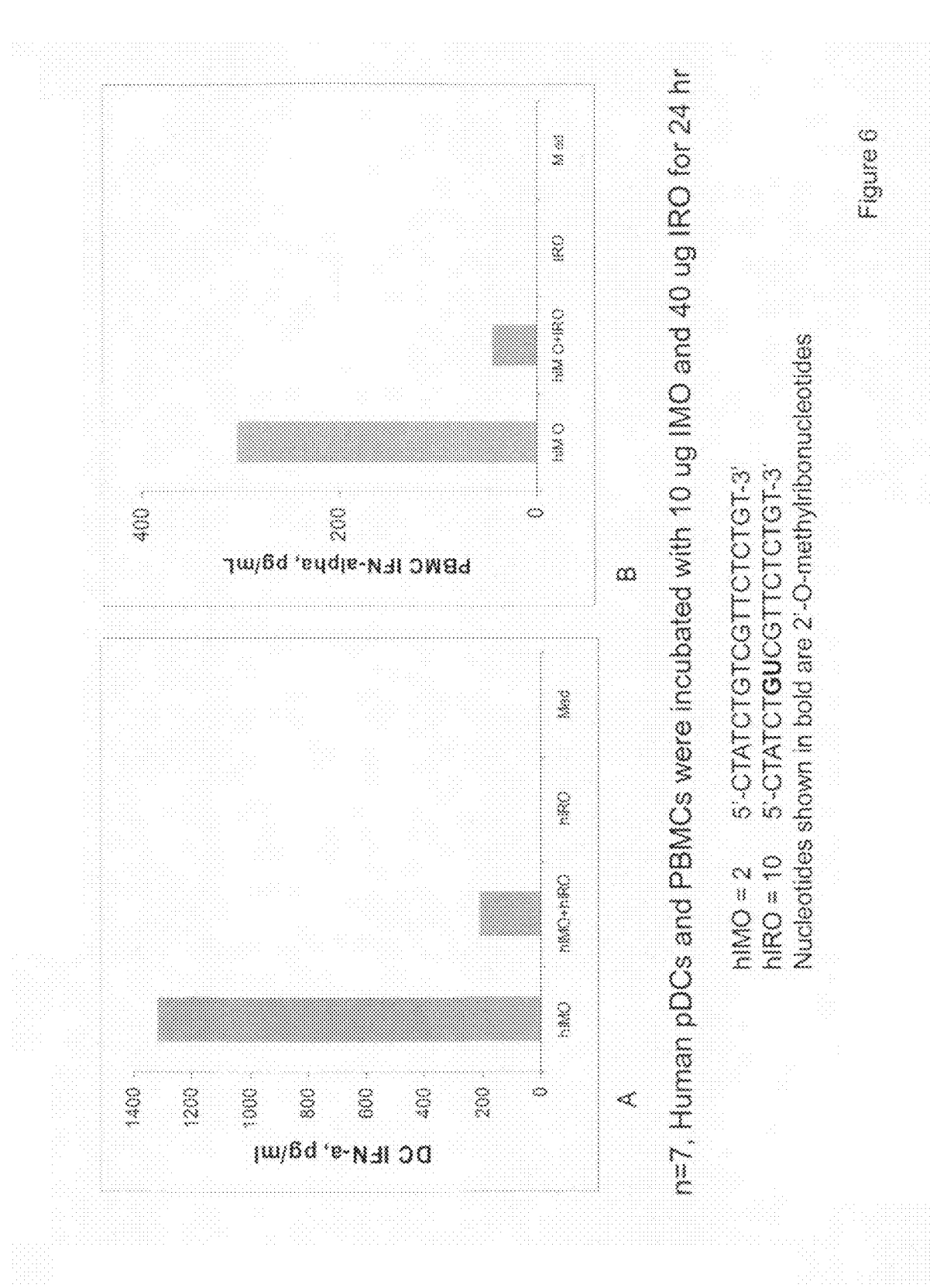
FIGS. 6A and 6B demonstrate that an IRO inhibited TLR9 agonist activity in human cell cultures (SEQ ID NOS 2 and 10).

Human pDCs and PBMCs were incubated with 10 ug 5'-CTATCTGTCGTTCTCTGT-3' (human CpG sequence; IMO/SEQ ID NO 2) and 40 ug IRO 10 for 24 hr. The results are shown in FIG. 6. These results demonstrate that an IRO inhibited TLR9 agonist activity in human cell cultures, and more generally that IROs can inhibit TLRs in human cells.

Example 8

IRO Effect on OVA Induced Th2 Immune Response

Figure 7:
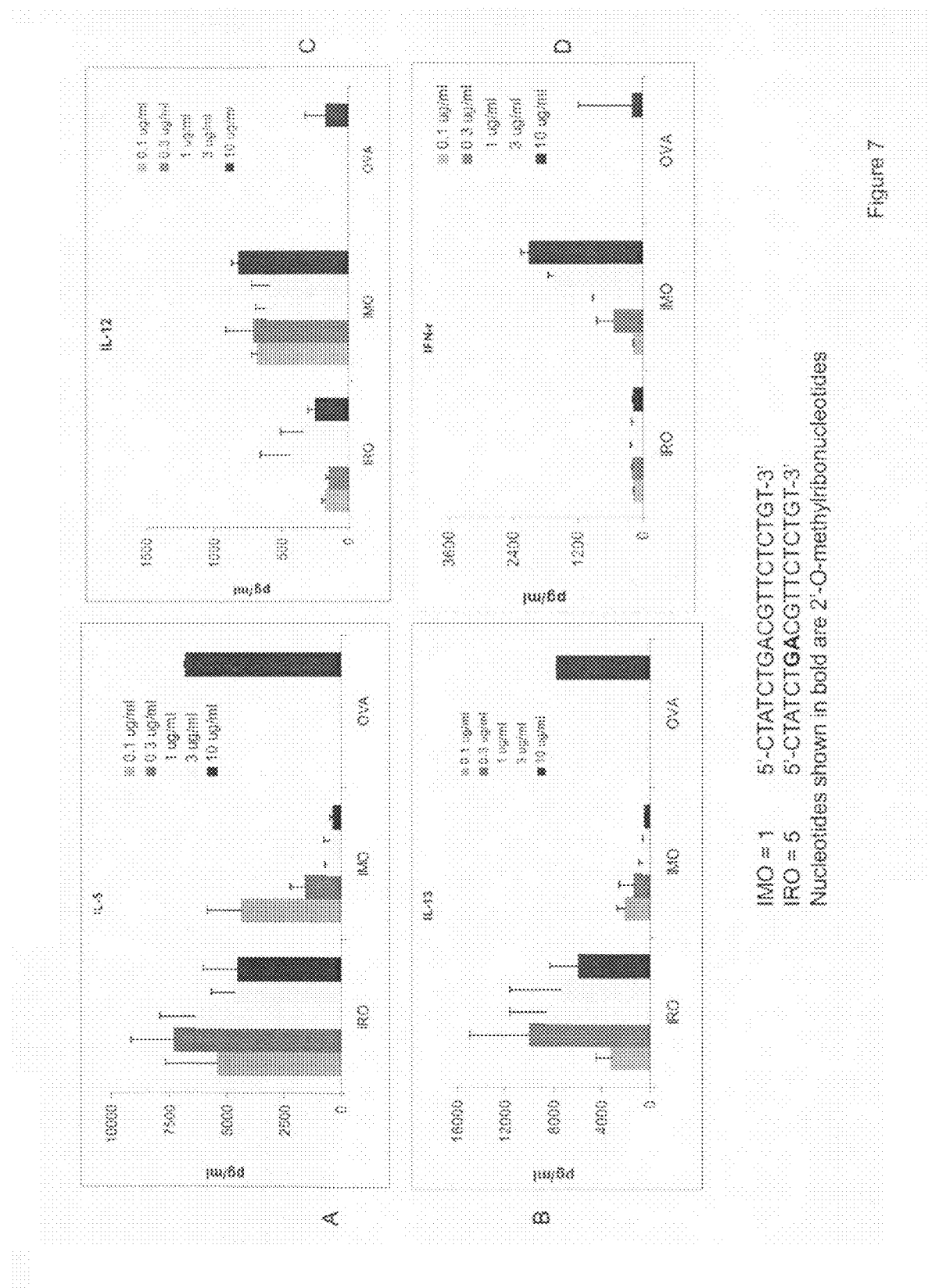
FIGS. 7A through 7D demonstrate an IRO effect on OVA induced Th2 and Th1 immune responses (SEQ ID NOS 1 and 5).

The results are shown in FIG. 7. These results demonstrate that an IRO does not have an effect on Ovalbumin ("OVA") induced Th2 immune responses, whereas IMO compounds reduce OVA induced Th2 response and cause the production of Th1 cytokines.

Example 9

IRO Inhibition of IMO Effects on Th1 and Th2 Immune Responses

Figure 8:
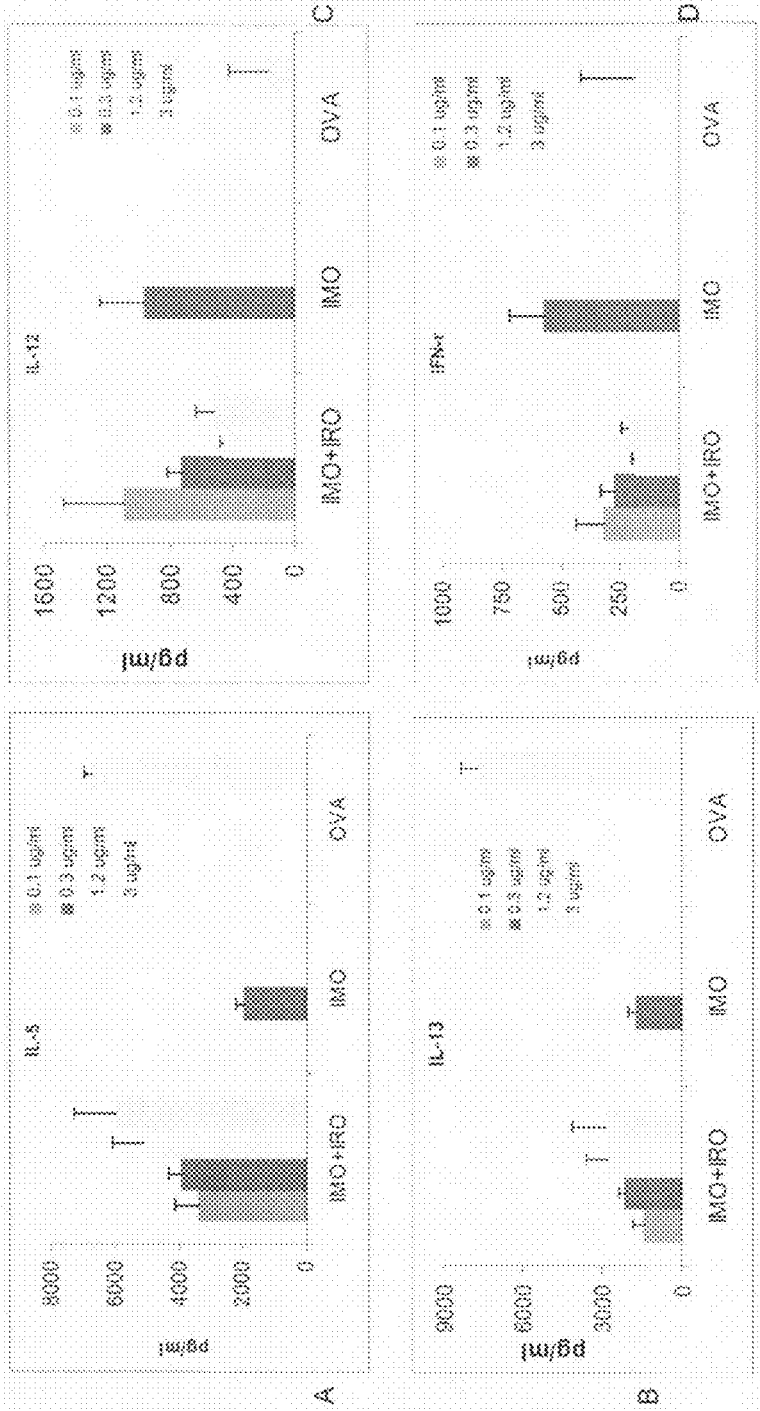
FIGS. 8A through 8D demonstrates that an IRO reversed Th2 inhibitory properties and inhibited Th1 immune responses induced by an IMO (SEQ ID NOS 1 and 5).

The results are shown in FIG. 8. These results demonstrate that an IRO can reverse Th2 inhibitory properties and can inhibit Th1 immune responses induced by IMO.

Example 10

Antibody Responses to IMO and IRO

Figure 9:
FIGS. 9A through 9C demonstrates antibody responses to an IMO and an IRO (SEQ ID NOS 1, 5, and 6).

Mice were immunized with HBsAg in the presence and absence of IMO 1 and IRO 5 or 6 and combinations thereof at wk 0 and wk 2 and antibody responses were measured wk 4. The results are shown in FIG. 9 and demonstrate reduction by an IRO on an IMO induced IgG2A immune response.

Example 11

Inhibition of Immune Stimulators Oligonucleotides

HEK293 cells stably expressing TLR9 (Invivogen) were transiently transfected with reporter gene, Seap, (Invivogen) for 6 hr. Cells were treated with 0.25 µg/ml IMO alone (IMO 1; 0 dose) and various concentrations of IROs for 18 hr. TLR9-dependent reporter gene expression was determined according to the manufacturer's protocol (Invivogen) and the results are expressed as % inhibition of immune stimulating oligonucleotide activity. The results are shown in Tables 5 and 6 below. These results demonstrate that IROs inhibited activity of IMO.

TABLE 5

Percent inhibition of immune stimulatory oligonucleotide 1. IIMO1 concentration was 0.25 µg/ml and IRO concentration was 2 µg/ml

| SEQ ID NO:/ IRO # | Sequence | % Inhibition |
|---|---|---|
| 5 | 5'-CTATCT<u>GA</u>CGTTCTCTGT-3' | 52.5% |
| 25 | 5'-CTATCTGAC$_2$GTTCTCTGT-3' | 17.5% |
| 26 | 5'-CTATCTGACG$_2$TTCTCTGT-3' | 15.3% |
| 33 | 5'-CTATCTGAC$_3$GTTCTCTGT-3' | 38.1% |
| 39 | 5'-CTATCT<u>GA</u>C$_4$GTTCTCTGT-3' | 52.8% |
| 41 | 5'-CTATCT<u>GA</u>C$_5$GTTCTCTGT-3' | 42.6% |
| 43 | 5'-CTATCT<u>GA</u>C$_6$GTTCTCTGT-3' | 23.6% |

IROs containing various modifications inhibit NF-κB activation of IMO in HEK293 cells expressing TLR9, and more generally IROs containing various modifications can inhibit NF-κB activation of IMO.

TABLE 6

Percent inhibition of immune stimulatory oligonucleotide 1. IMO1 concentration was 0.25 µg/ml and IRO concentration was 3 µg/ml.

| SEQ ID NO:/ IRO # | Sequence | % Inhibition |
|---|---|---|
| 5 | 5'-CTATCT<u>GA</u>CGTTCTCTGT-3' | 76.5% |
| 17 | 5'-CTATCT<u>GA</u>CG$_1$TTCTCTGT-3' | 76.4% |
| 34 | 5'-CTATCTGACG$_3$TTCTCTGT-3' | 32.2% |
| 37. | 5'-CTATCT<u>GA</u>CG$_4$TTCTCTGT-3' | 78.3% |

IROs containing various modifications inhibit NF-κB activation of IMO in HEK293 cells expressing TLR9, and more generally IROs containing various modifications can inhibit NF-κB activation of IMO.

Example 12

Time-Dependence Inhibition by IRO

C57BL/6 mice were injected subcutaneously (s.c.) at left underarm with 0.25 mg/kg to 10 mg/kg TLR agonist and 1 mg/kg to 20 mg/kg IRO 5, 17 or 37 or 5'-TCCTGGCGGG-GAAGT-3' (poly dG control; oligo/SEQ ID NO 12) at right under arm at one hour (−1 h) or up to forty-eight hours (−48) before or at the same time as TLR agonist (Oh). Serum samples were taken at 2 hours after stimulating IMO injection and determined IL-12 levels by ELISA. The results are shown in Tables 7-22 below. These results demonstrate that both pre-administration and simultaneous administration of an IRO inhibits agonists of TLR9, and that the inhibitory activities of an IRO were effective even when administered 48 hours prior to the administration of the IMO. More generally, these results demonstrate that pre-administration and simultaneous administration of an IRO can both inhibit TLR agonists and that the inhibitory activities of an IRO can be seen even when administered many hours prior to the administration of the TLR agonist.

TABLE 7

Inhibition of IMO 3 induced IL-12 (ng/ml ± SD)
by IRO 5 in vivo, C57BL/6 mice (n = 3)

| IMO alone | IRO alone | IRO + IMO Time of IMO administration after IRO administration | | | |
|---|---|---|---|---|---|
| (0.25 mg/kg) | (2 mg/kg) | 0 hr | 1 hr | 3 hr | 6 hr |
| 21.1 ± 1.84 | 0.81 ± 0 | 0.59 ± 0.48 | 1.54 ± 0.17 | 6.53 ± 0.81 | 10.41 ± 0.48 |

IRO 5 inhibited IMO induced IL-12 production when injected up to 6 hr after IRO administration. More generally, these results demonstrate that an IRO can inhibit TLR activation and IMO induced IL-12 production when IMO is administered or initially becomes present hours after IRO administration.

TABLE 8

Inhibition of IMO 3 induced IL-12 (ng/ml ± SD)
by IRO 5 in vivo, C57BL/6 mice (n = 3)

| IMO alone | IRO alone | IRO + IMO Time of IMO administration after IRO administration | | | |
|---|---|---|---|---|---|
| (0.25 mg/kg) | (20 mg/kg) | 0 hr | 1 hr | 3 hr | 6 hr |
| 33.8 ± 3.8 | 0.73 ± 0.7 | 0.87 ± 1.19 | 1.52 ± 2.01 | 2.2 ± 2.4 | 1.84 ± 3.18 |

IRO 5 potently inhibited IMO induced IL-12 production when injected up to 6 hr after IRO administration. More generally, these results demonstrate that an IRO can substantially inhibit TLR activation and IMO induced IL-12 production when IMO is administered or initially becomes present hours after IRO administration.

TABLE 9

Inhibition of IMO 3 induced IL-12 (ng/ml ± SD)
by IRO 5 in vivo, C57BL/6 mice (n = 3)

| IMO alone | IRO alone | IRO + IMO Time of IMO administration after IRO administration | | | |
|---|---|---|---|---|---|
| (0.25 mg/kg) | (20 mg/kg) | 6 hr | 14 hr | 24 hr | 48 hr |
| 25.8 ± 2.6 | 0.17 ± 0 | 0.04 ± 0 | 1.25 ± 0 | 1.8 ± 0.29 | 2.9 ± 0.1 |

IRO 5 potently inhibited IMO induced IL-12 production when injected up to 48 hr after IRO administration. More generally, these results demonstrate that an IRO can substantially inhibit TLR activation and IMO induced IL-12 production when IMO is administered or initially becomes present hours after IRO administration.

TABLE 10

Inhibition of IMO 3 induced IL-12 (ng/ml ± SD)
by IRO 17 in vivo, C57BL/6 mice (n = 3)

| IMO alone | IRO alone | IRO + IMO Time of IMO administration after IRO administration | | |
|---|---|---|---|---|
| (0.25 mg/kg) | (2 mg/kg) | 3 hr | 6 hr | 24 hr |
| 6.6 ± 0.64 | 0.67 ± 0.02 | 1.01 ± 0.06 | 1.25 ± 0.29 | 4.29 ± 1.12 |

IRO 17 inhibited IMO induced IL-12 production when injected up to 6 hr or more after IRO administration. More generally, these results demonstrate that an IRO can inhibit TLR activation and IMO induced IL-12 production when IMO is administered or initially becomes present hours after IRO administration.

TABLE 11

Inhibition of IMO 3 induced IL-12 (ng/ml ± SD)
by IRO 37 in vivo, C57BL/6 mice (n = 3)

| IMO alone | IRO alone | IRO + IMO Time of IMO administration after IRO administration |
|---|---|---|
| (0.25 mg/kg) | (2 mg/kg) | 3 hr |
| 6.6 ± 0.64 | 0.67 ± 0.02 | 0.91 ± 0.03 |

IRO 37 inhibited IMO induced IL-12 production when injected up to 3 hr after IRO administration. More generally, these results demonstrate that an IRO can inhibit TLR activation and IMO induced IL-12 production when IMO is administered or initially becomes present hours after IRO administration.

TABLE 12

Inhibition of IMO 3 induced IL-12 (ng/ml ± SD) by control poly dG (5'-TCCTGGAGGGGAAGT-3' (SEQ ID NO 73)) in vivo, C57BL/6 mice (n = 3)

| IMO alone (0.25 mg/kg) | IRO alone (10 mg/kg) | Control + IMO Time of IMO administration after | | Control administration 24 hr |
|---|---|---|---|---|
| | | 3 hr | 6 hr | |
| 18.24 ± 0.22 | 1.47 ± 0 | 1.38 ± 0.18 | 10.03 ± 0.37 | 16.97 ± 0.52 |

A poly dG compound known to show TLR9 antagonist activity inhibited IMO induced IL-12 production when injected up to 6 hr after IRO administration. Compared with the data for IRO (e.g. IRO 5 in Table 7), control poly dG oligo antagonistic effects are short-term and transient.

TABLE 13

Inhibition of IMO 3 induced IL-12 (ng/ml ± SD) by control poly dG (5'-TCCTGGCGGGGAAGT-3' (SEQ ID NO 12)) in vivo, C57BL/6 mice (n = 3)

| IMO alone (0.25 mg/kg) | IRO alone (10 mg/kg) | Control + IMO Time of IMO administration after | | Control administration 24 hr |
|---|---|---|---|---|
| | | 3 hr | 6 hr | |
| 18.24 ± 0.22 | 1.2 ± 0 | 0.81 ± 0.06 | 10.1 ± 0.09 | 19.02 ± 1.6 |

A poly dG compound known to show TLR9 antagonist activity inhibited IMO induced IL-12 production when injected up to 6 hr after IRO administration. Compared with the data for IRO (e.g. IRO 5 in Table 7), control poly dG oligo antagonistic effects are short and transient.

TABLE 14

Inhibition of R848, a TLR7 and TLR8 agonist, induced IL-12 (ng/ml ± SD) by IRO 5 in vivo, C57BL/6 mice (n = 3)

| R848 alone (0.5 mg/kg) | IRO alone (2 mg/kg) | IRO + R848 Time of R848 administration after IRO administration 1 hr |
|---|---|---|
| 128 ± 2.9 | 1.48 ± 0.17 | 56.0 ± 3.3 |

IRO 5 shows a low transient inhibition of R848 induced IL-12 production when injected up to 1 hr after IRO administration. More generally, these data demonstrate that an IRO can inhibit activity of intracellular TLRs.

TABLE 15

Inhibition of PolyI:PolyC, a TLR3 agonist, induced IL-12 (ng/ml ± SD) by IRO 5 in vivo, C57BL/6 mice (n = 3)

| PolyI.PolyC alone (10 mg/kg) | IRO alone (2 mg/kg) | IRO + PolyI.PolyC Time of PolyI,.PolyC administration after IRO administration 1 hr |
|---|---|---|
| 8.7 ± 0.6 | 1.48 ± 0.17 | 2.1 ± 0.07 |

IRO 5 shows a low transient inhibition of PolyI.PolyC induced IL-12 production when injected up to 1 hr after IRO administration. More generally, these data demonstrate that an IRO can inhibit TLR activation and PolyI.PolyC induced IL-12 production.

TABLE 16

Inhibition of IMO induced MCP-1 (ng/ml ± SD) by IRO 5 in vivo, C57BL/6 mice (n = 3)

| IMO alone (0.25 mg/kg) | IRO alone (2 mg/kg) | IRO + IMO Time of R848 administration after IRO administration 1 hr |
|---|---|---|
| 2.2 ± 0.25 | NT | 0.28 ± 0.73 |

IRO 5 shows potent inhibition of IMO induced MCP-1 production when injected up to 1 hr after IRO administration. More generally, these data demonstrate that an IRO can inhibit TLR activation and IMO induced MCP-1 production.

TABLE 17

Inhibition of R848, a TLR7 and TLR8 agonist, induced MCP-1 (ng/ml ± SD) by IRO 5 in vivo, C57BL/6 mice (n = 3)

| R848 alone (0.5 mg/kg) | IRO alone (2 mg/kg) | IRO + R848 Time of R848 administration after IRO administration 1 hr |
|---|---|---|
| 11 ± 1.4 | | 7.2 ± 1.7 |

IRO 5 shows a low transient inhibition of R848 induced MCP-1 production when injected up to 1 hr after IRO administration. More generally, these data demonstrate that an IRO can inhibit TLR activation and MCP-1 production through intracellular TLRs.

TABLE 18

Inhibition of PolyI.PolyC, a TLR3 agonist, induced MCP-1 (ng/ml ± SD) by IRO 5 in vivo, C57BL/6 mice (n = 3)

| PolyI.PolyC alone (10 mg/kg) | IRO alone (2 mg/kg) | IRO + PolyI.PolyC Time of PolyI.PolyC administration after IRO administration 1 hr |
|---|---|---|
| 4.6 ± 0.6 | | 1.8.0 ± 0.57 |

IRO 5 shows a low transient inhibition of PolyI.PolyC induced MCP-1 production when injected up to 1 hr after IRO administration. More generally, these data demonstrate that an IRO can inhibit TLR activation and MCP-1 production of a PolyI.PolyC

TABLE 19

Inhibition of IMO 3 induced IL-12 (ng/ml ± SD) by IRO 5 in vivo, C57BL/6 mice (n = 3)

| IMO alone (0.25 mg/kg) | IRO alone (20 mg/kg) | IRO + IMO Time of IMO administration after IRO administration | | |
|---|---|---|---|---|
| | | 2 days | 5 days | 7 days |
| 33.2 ± 8.7 | NT | 14.5 ± 5.17 | 17.19 ± 11.2 | 28.0 ± 7.75 |

IRO 5 shows potent inhibition of IMO induced IL-12 production when injected up to 7 days after IRO administration. More generally, these data demonstrate that an IRO can inhibit TLR activation and IMO induced IL-12 production in mammals.

TABLE 20

Inhibition of IMO induced IL-12 (ng/ml ± SD) by IRO 5 in vivo, C57BL/6 mice (n = 3)

| IMO alone (0.25 mg/kg) | IRO alone (10 mg/kg) | IRO + IMO Time of IMO administration after IRO administration 72 hr |
|---|---|---|
| 53.39 ± 2.71 | 2.03 ± 2.03 | 28.72 ± 0.79 |

IRO 5 shows potent inhibition of IMO induced IL-12 production when injected up to 72 hr after IRO administration. More generally, these data demonstrate that an IRO can inhibit TLR activation and IMO induced IL-12 production in mammals hours after the IRO is administered.

TABLE 21

Inhibition of R848, a TLR7 and TLR8 agonist, induced IL-12 (ng/ml ± SD) by IRO 5 in vivo, C57BL/6 mice (n = 3)

| R848 alone (0.125 mg/kg) | IRO alone (10 mg/kg) | IRO + R848 Time of R848 administration after IRO administration 72 hr |
|---|---|---|
| 96.5 ± 3.4 | 2.03 ± 2.03 | 13.64 ± 0.47 |

IRO 5 shows inhibition of R848 induced IL-12 production when injected up to 72 hr after IRO administration. More generally, these data demonstrate that an IRO can inhibit the activity of an agonist of intracellular TLR's and TLR agonist induced IL-12 production in mammals hours after the IRO is administered.

TABLE 22

Inhibition of PolyI.PolyC, a TLR3 agonist, induced IL-12 (ng/ml ± SD) by IRO 5 in vivo, C57BL/6 mice (n = 3)

| PolyI.PolyC alone (10 mg/kg) | IRO alone (10 mg/kg) | IRO + PolyI.PolyC Time of PolyI.PolyC administration after IRO administration 72 hr |
|---|---|---|
| 28.42 ± 1.2 | 2.03 ± 2.03 | 26.61 ± 5.97 |

IRO 5 shows no inhibition of PolyI.PolyC induced IL-12 production when injected 72 hr after IRO administration.

Example 13

Short-Term and Long-Term Blocking Activities of IRO Against TLR Agonist

Figure 10:
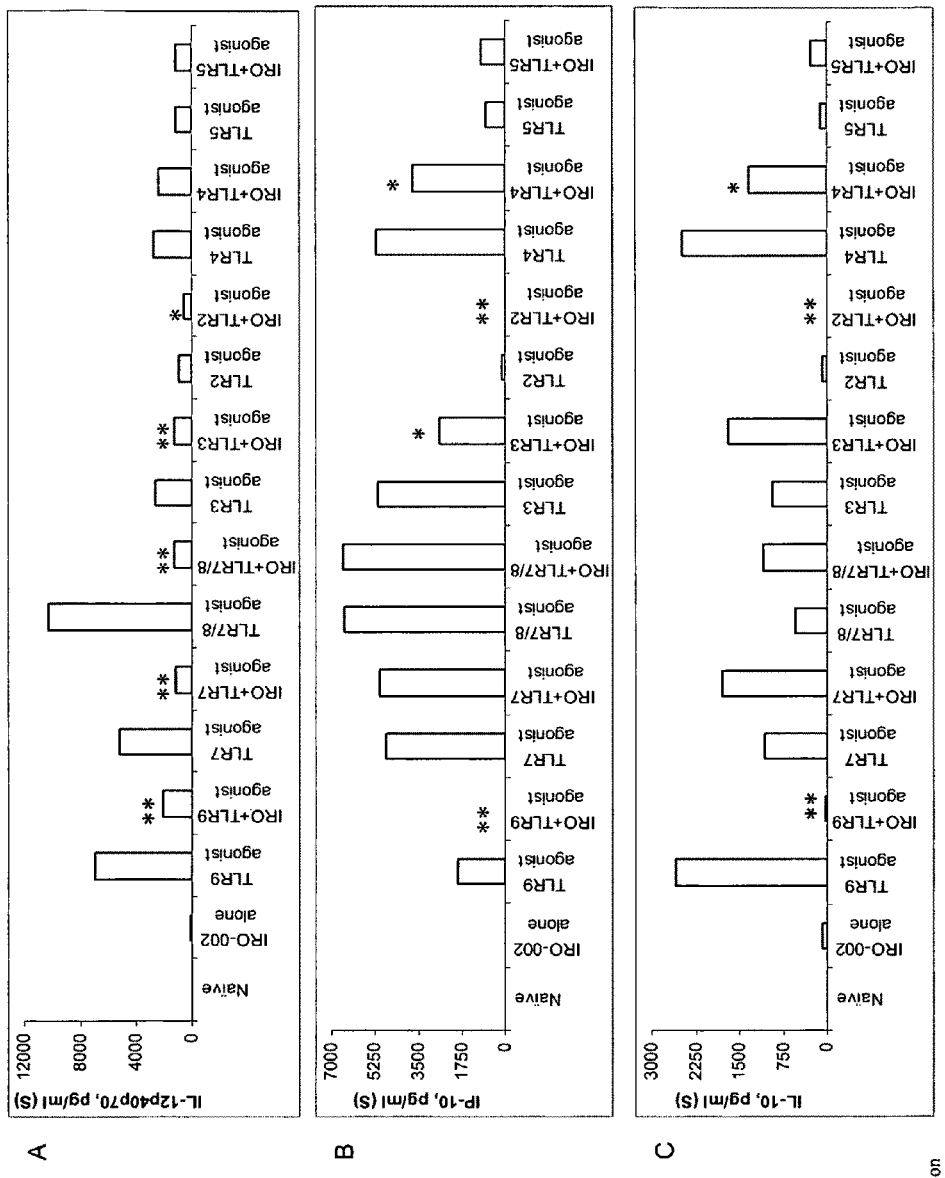
FIGS. 10A through 10C demonstrates early inhibitory activity of selected IROs on TLR2, TLR3, TLR4, TLR5, TLR7, TLR8, and TLR9 in vivo.
Figure 11:
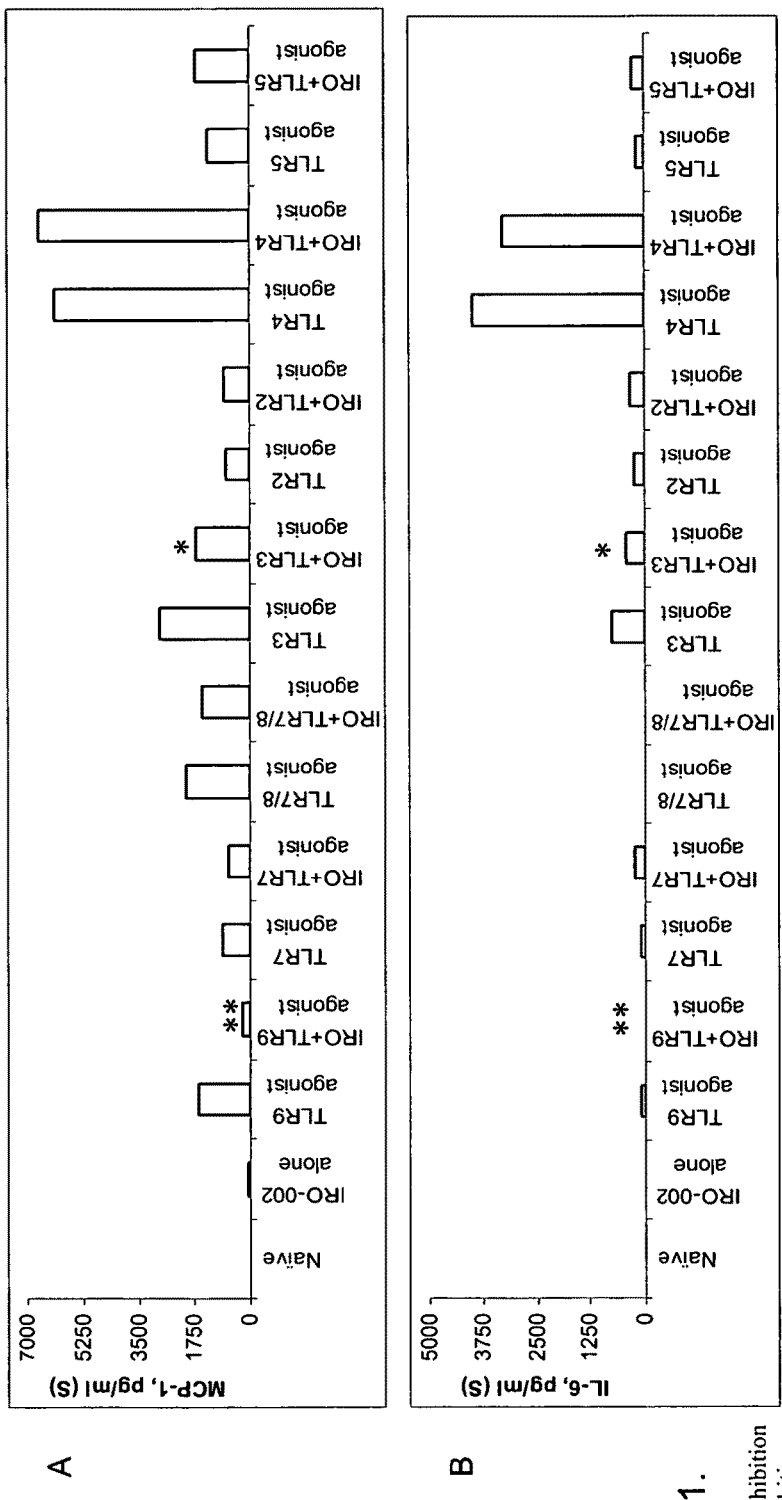
FIG. 11 demonstrates early inhibitory activity of selected IROs on TLR2, TLR3, TLR4, TLR5, TLR7, TLR8, and TLR9 in vivo.
Figure 12:
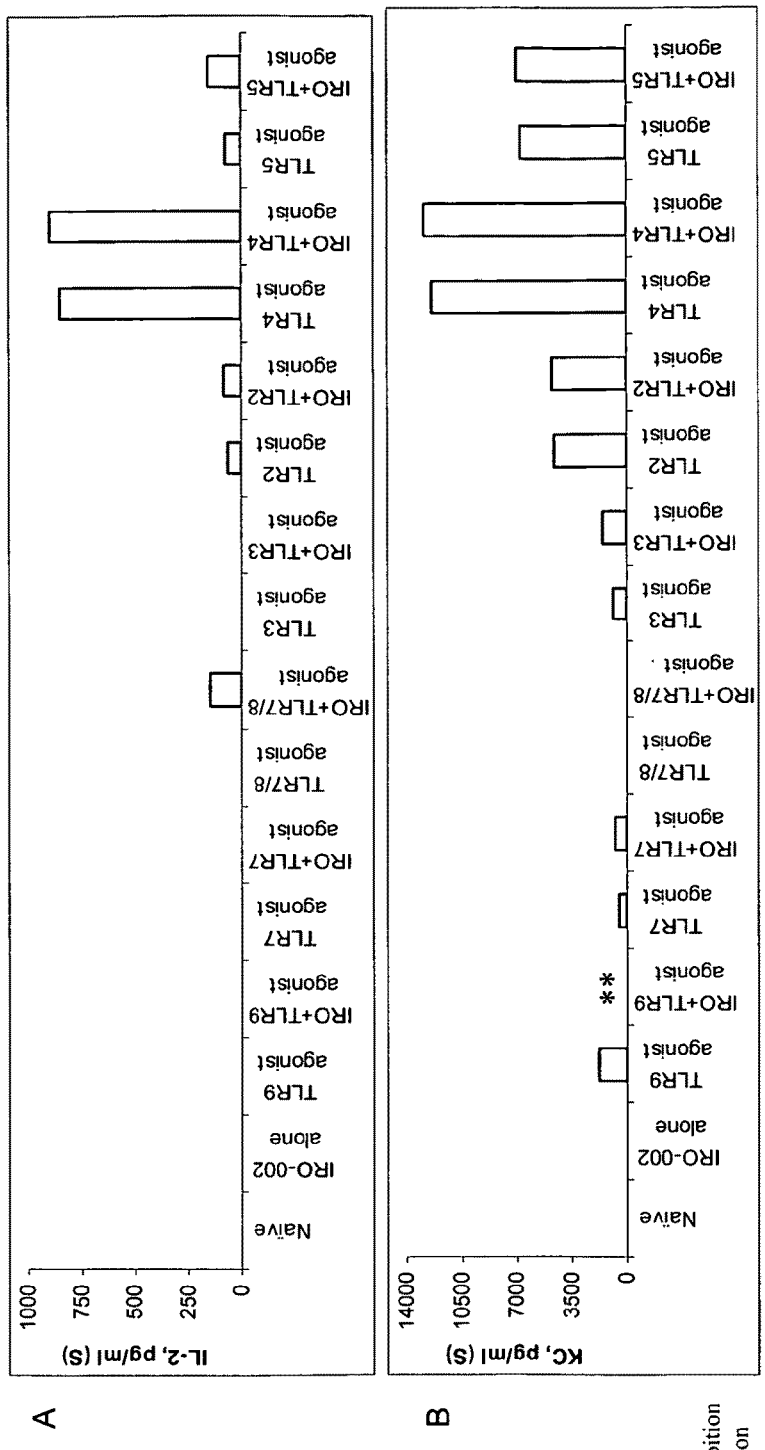
FIG. 12 demonstrates early inhibitory activity of selected IROs on TLR2, TLR3, TLR4, TLR5, TLR7, TLR8, and TLR9 in vivo.

To assess the short term activity and selectivity of IRO compounds, mice were subcutaneously injected with 2 mg/kg IRO in their right flank one hour (−1 h) before subcutaneous administration of a TLR agonist to the left flank. Serum samples were taken at 2 hours after administration of the TLR agonist and were analyzed using multiple cytokine/chemokine detecting Luminex kits obtained from Biosource (Camarillo, Calif.). Manufacture recommended protocols were followed. Cytokine/chemokine values were determined from mean values falling on the standard curve determined on a Luminex 100 instrument. Luminex analysis was performed using STarStation software (Applied Cytometry Systems, Sacramento, Calif.). The following representative agonists were used at the indicated dose: 5'-TCTGACG$_1$TTCT-X-TCTTG$_1$CAGTCT-5' (SEQ ID NO: 3) (TLR9 agonist; 0.25 mg/kg, G$_1$=7-deaza-dG), R848 (TLR7/8 agonist, 0.1 mg/kg), Loxoribine (TLR7 agonist, 100 mg/kg), Flagellin (TLR5 agonist, 0.25 mg/kg), LPS (TLR4 agonist, 0.25 mg/kg), PolyI.PolyC (TLR3 agonist, 20 mg/kg), and MALP-2 (TLR2 agonist, 0.5 mg/kg). The results are shown in FIGS. 10-12. These data demonstrate that IROs can inhibit cytokine/chemokine production in response to TLR agonists. The effect is greater for intracellular TLRs (e.g. TLR3, TLR7, TLR8, and TLR9) as compared to extracellular TLRs (e.g. TLR2, TLR4, and TLR5).

Figure 13:
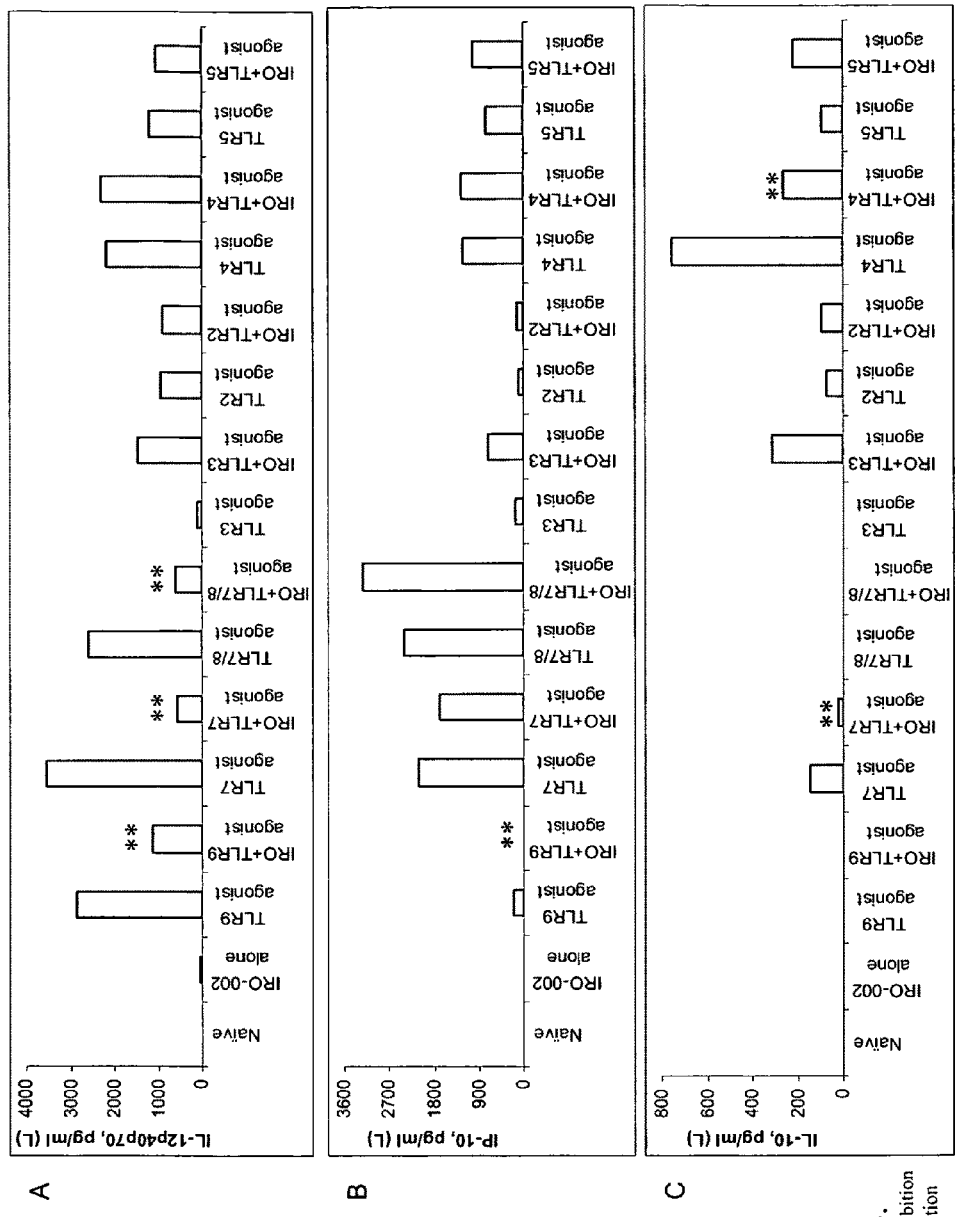
FIG. 13 demonstrates long-term antagonist activity of selected IROs on TLR2, TLR3, TLR4, TLR5, TLR7, TLR8, and TLR9 in vivo.
Figure 14:
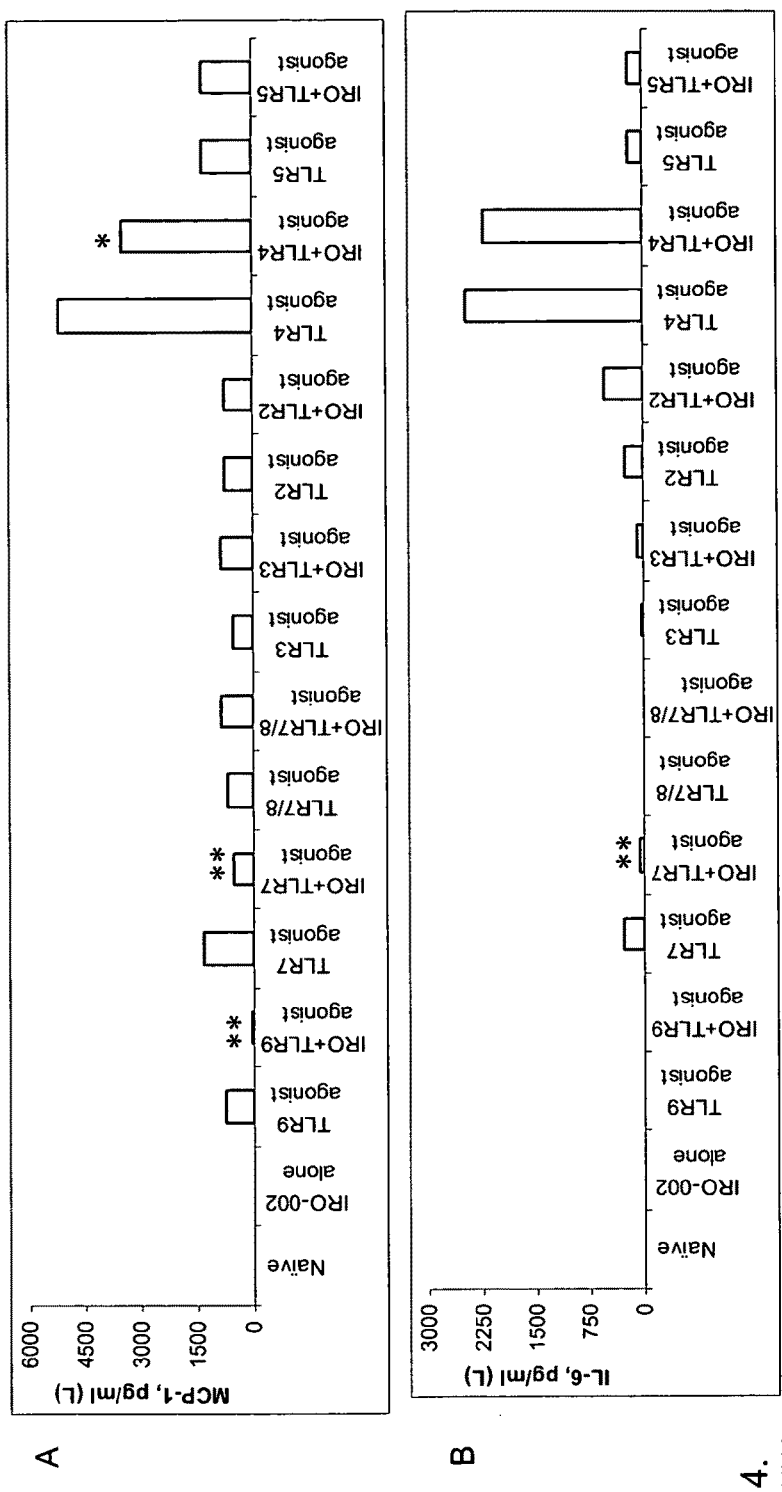
FIG. 14 demonstrates long-term antagonist activity of selected IROs on TLR2, TLR3, TLR4, TLR5, TLR7, TLR8, and TLR9 in vivo.
Figure 15:
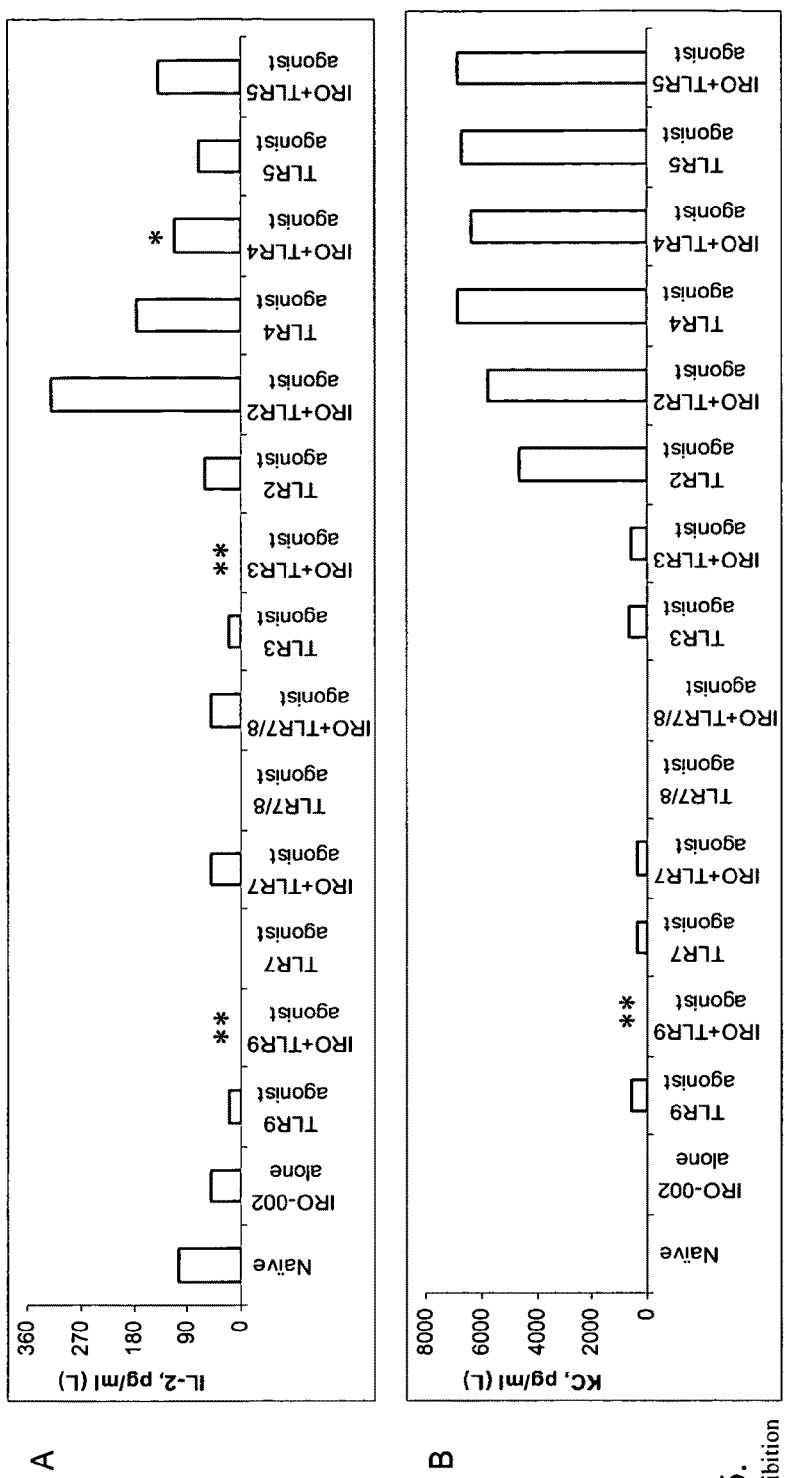
FIG. 15 demonstrates long-term antagonist activity of selected IROs on TLR2, TLR3, TLR4, TLR5, TLR7, TLR8, and TLR9 in vivo.

To assess the long-term activity and selectivity of IRO compounds, mice were subcutaneously injected with 10 mg/kg IRO in their right flank seventy-two hours (−72 h) before subcutaneous administration of a TLR agonist (as described above) to the left flank. Serum samples were taken at 2 hours after administration of the TLR agonist and were analyzed as described above. The results are shown in FIGS. 13-15. These results demonstrate pre-administration administration of an IRO was able to inhibit TLR agonist, and that the inhibitory activities of IRO were effective even when administered 72 hours prior to the administration of the agonist.

Example 14

Activities of IRO Compounds in Lupus Mouse Model

Figure 16:
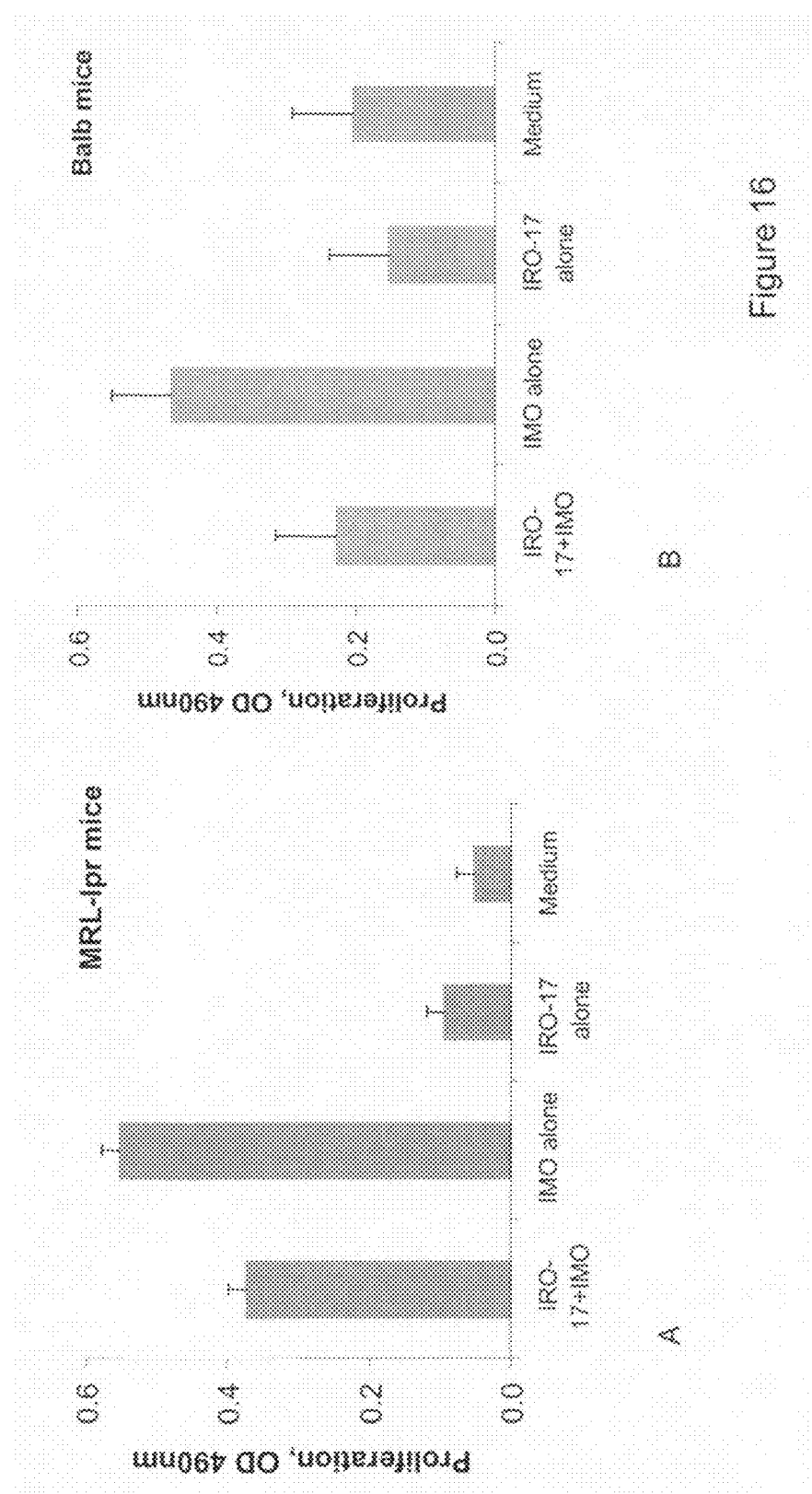
FIGS. 16A and 16B demonstrate that an IRO inhibits proliferation of wild type (BALB/c) and lupus prone (MRL-lpr) mice B lymphocyte proliferation in vitro.

Purified mouse spleen B cells from wild-type (BALB/c) and lupus prone (MRL-lpr) mice were cultured with 1 μg/ml IRO-17 in the presence or absence of 0.3 μg/ml IMO, or 0.3 μg/ml IMO or medium alone for 72 h. The results are shown in FIG. 16. These results demonstrate that administration of IRO was able to inhibit B lymphocyte proliferation.

Figure 17:
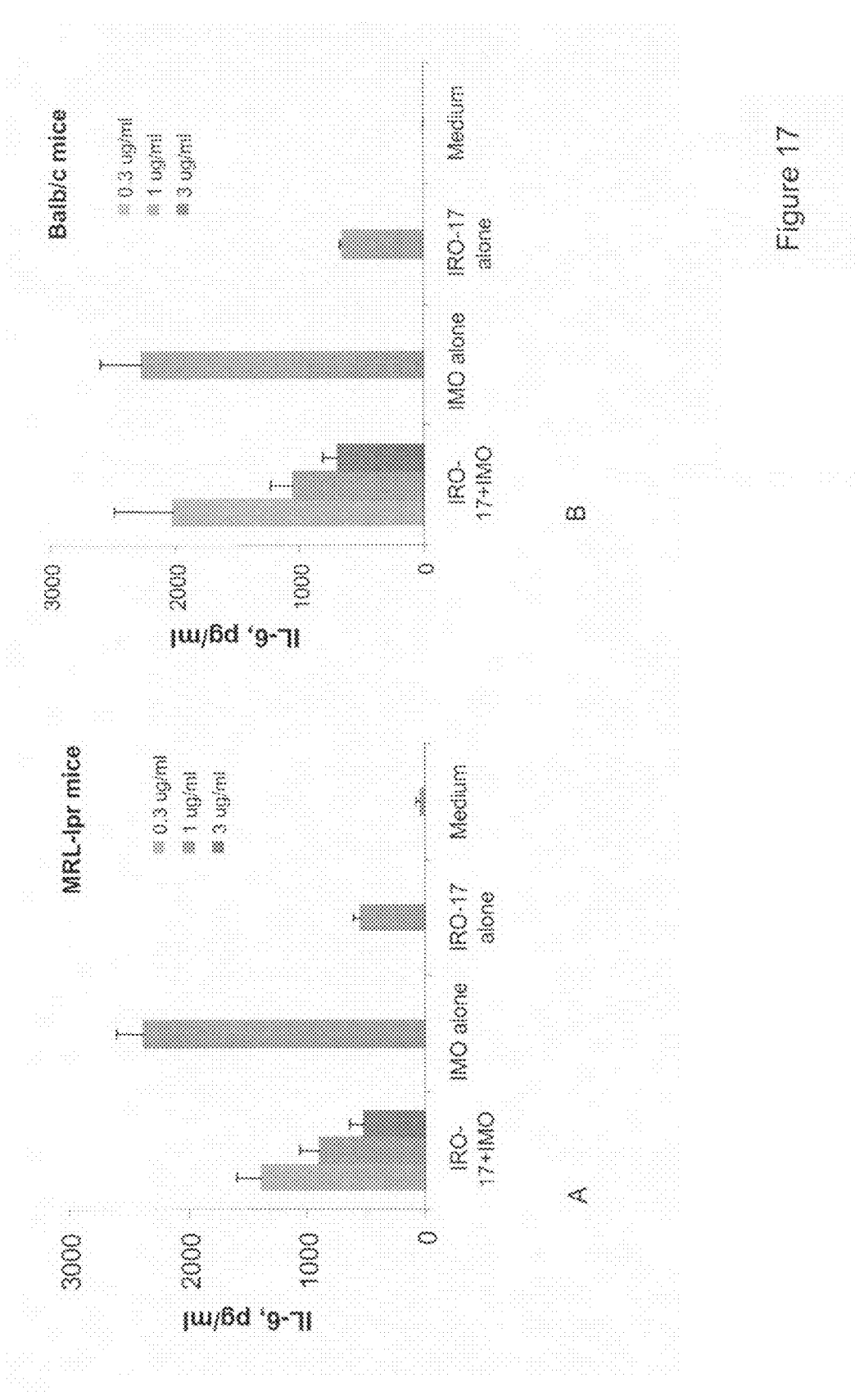
FIGS. 17A through 17F demonstrate that an IRO inhibited IL-6 and IL-12 production by wild type (BALB/c) and lupus prone (MRL-lpr) mice B lymphocytes and lupus prone (NZBW) mice spleen cells in vitro.
Figure 17:
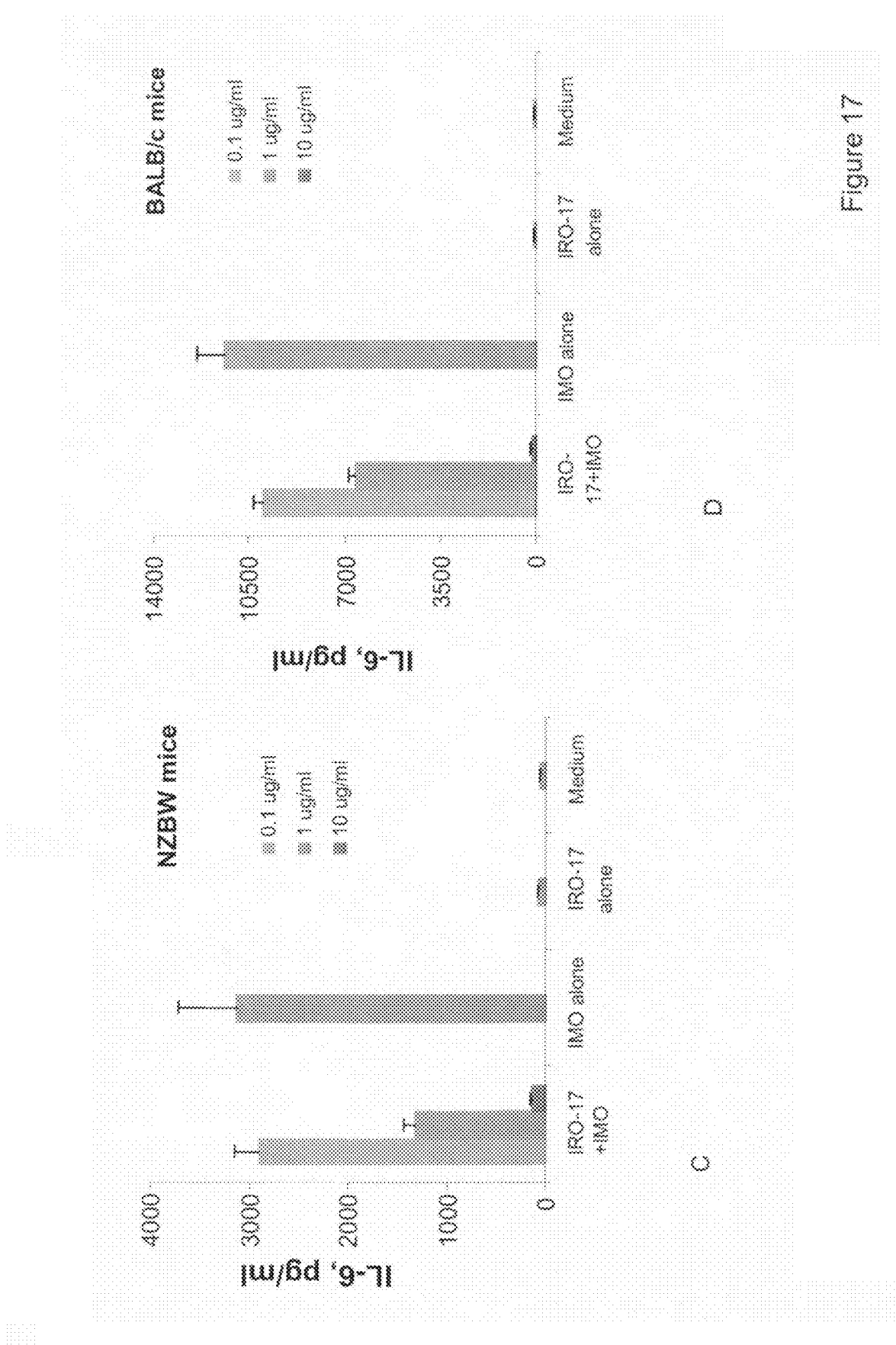
Figure 17:
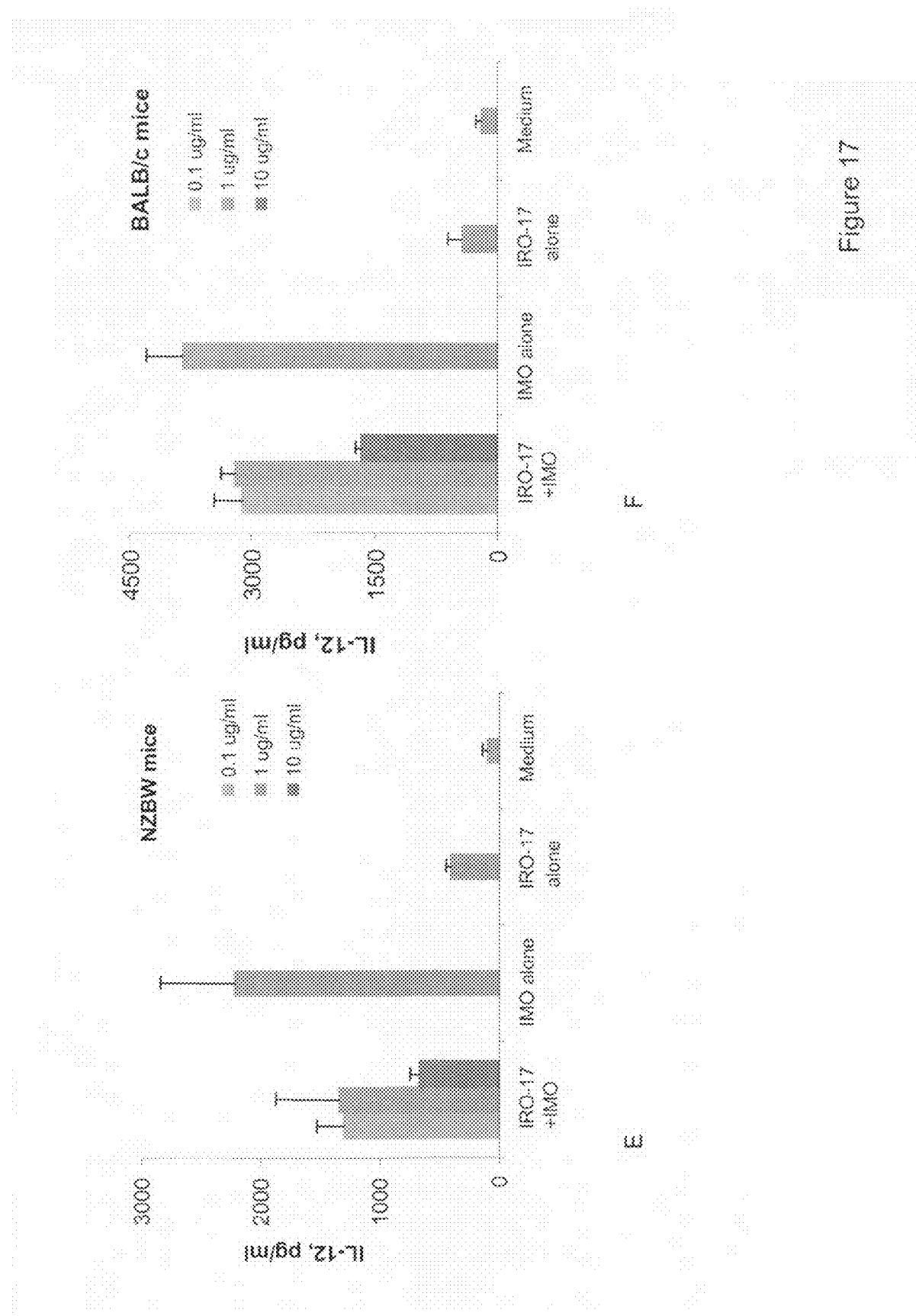
Figure 18A:
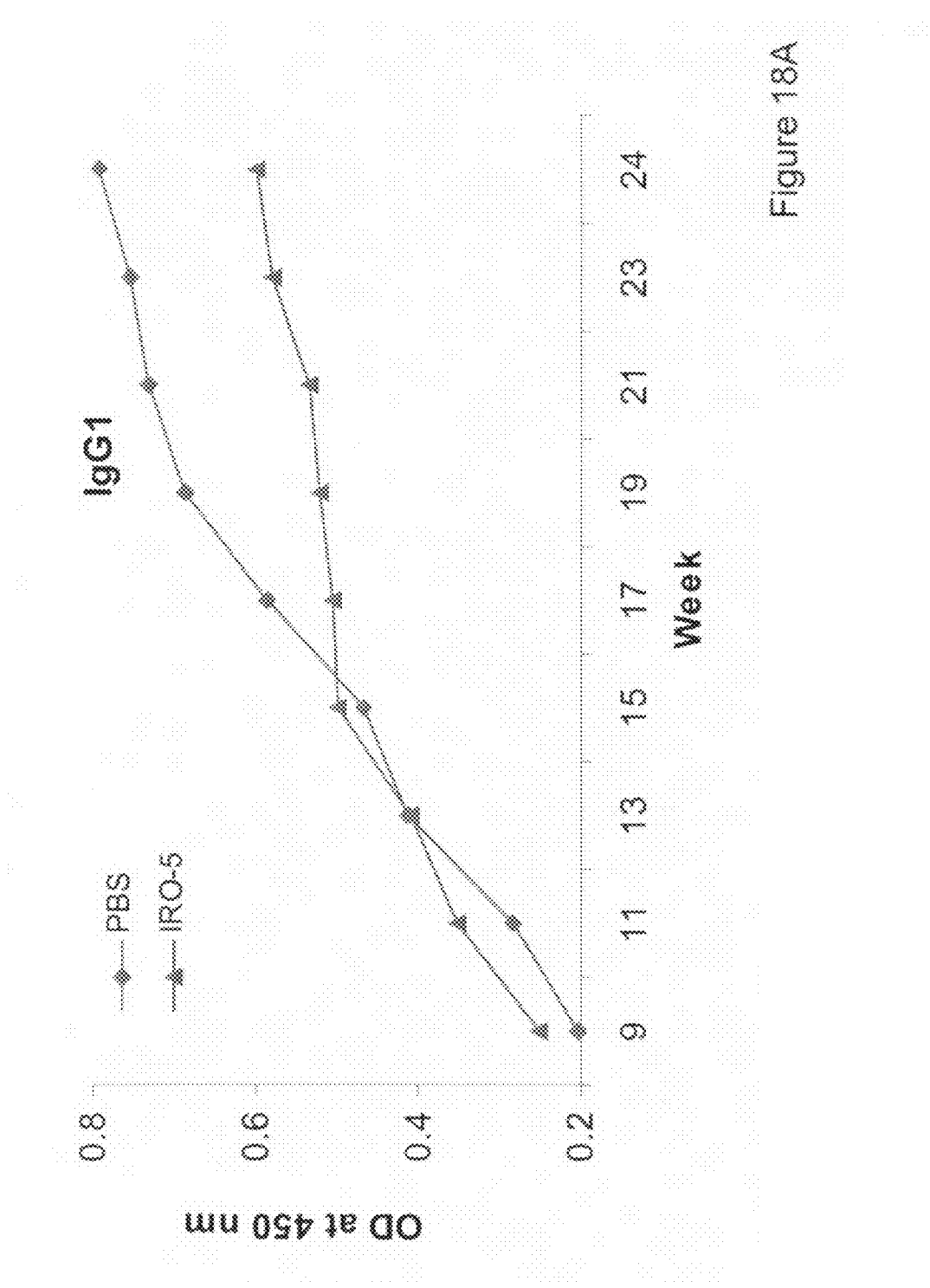
FIGS. 18A through 18F demonstrate that MRL-lpr mice injected with an IRO reduced levels of anti-DNA IgG1 and IgG2a antibodies in serum and protein in urine.
Figure 18B:
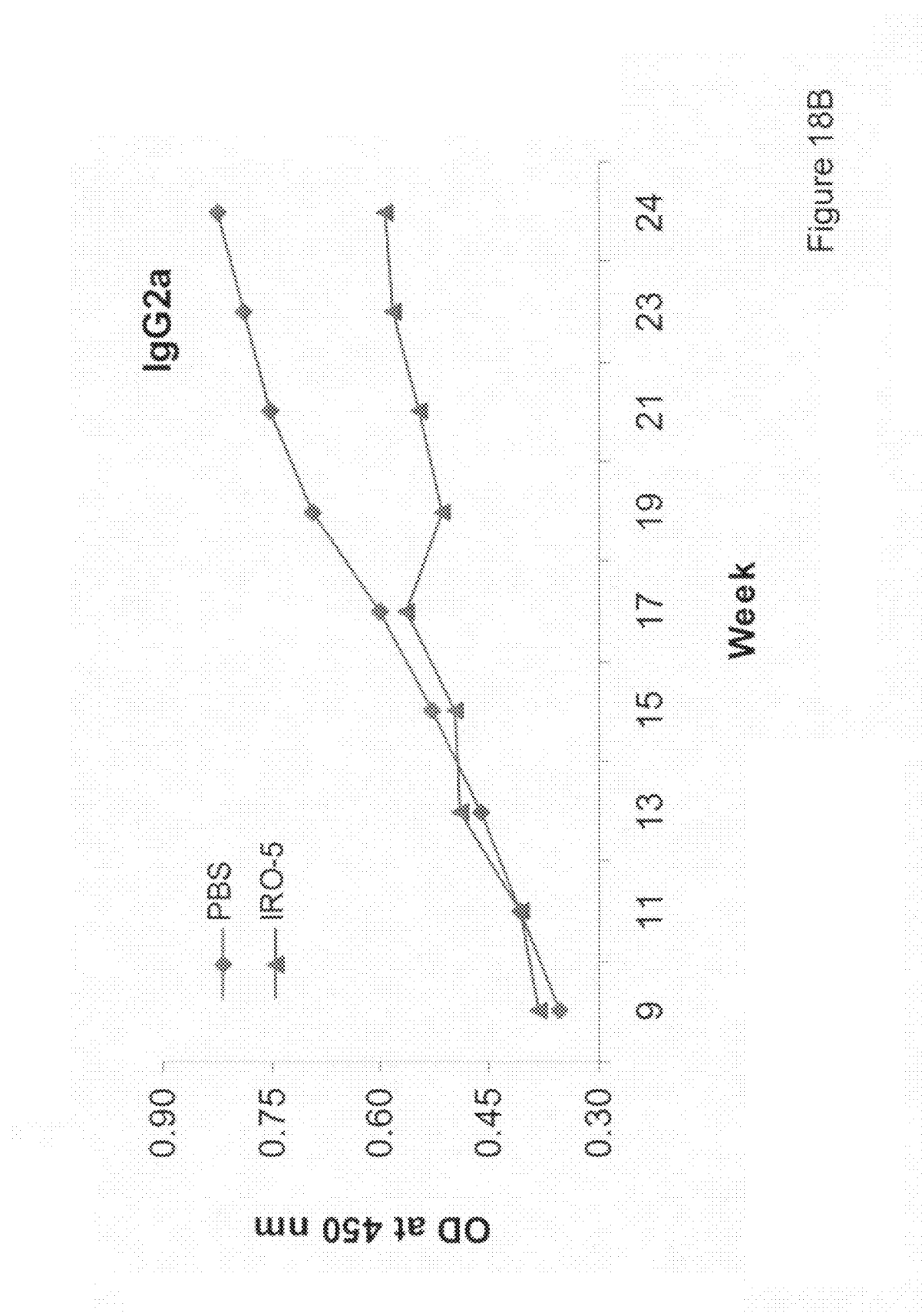
Figure 18:
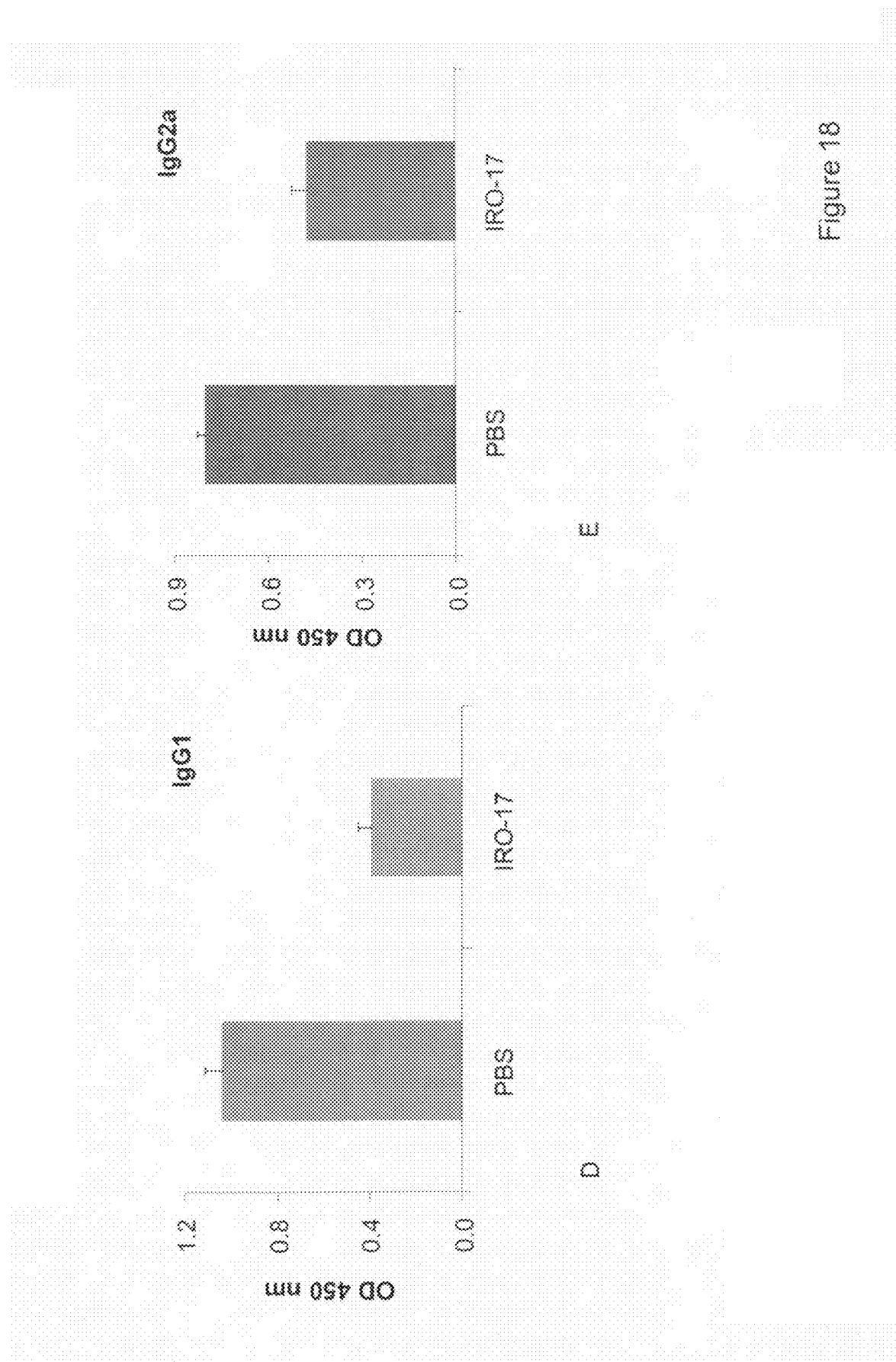
Figure 18F:
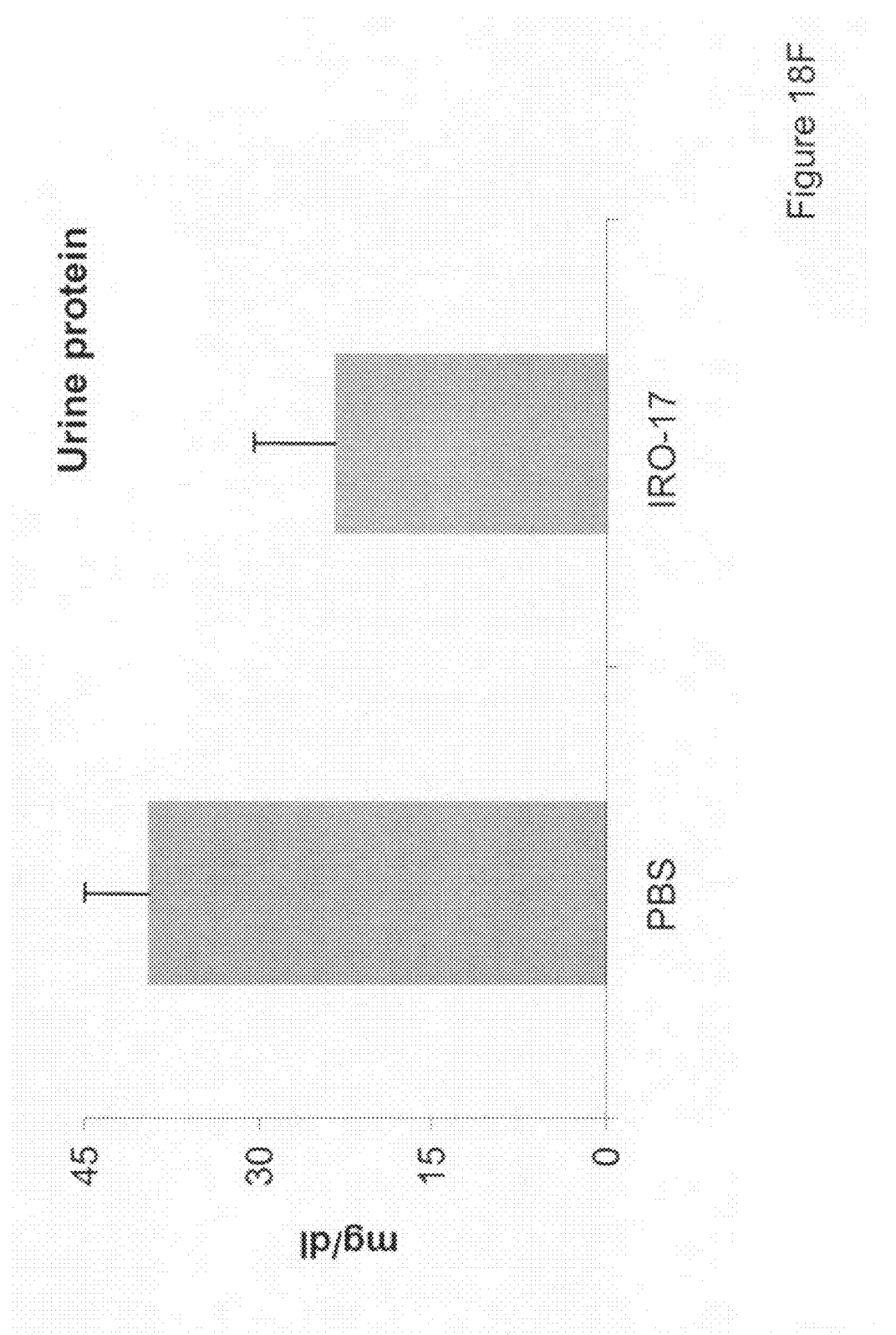

Purified mouse spleen B cells from wild-type (BALB/c) and lupus prone (MRL-lpr) mice were cultured with 1 μg/ml IRO-17 in the presence or absence of 0.3 μg/ml IMO, or 0.3 μg/ml IMO or medium alone for 72 h. The results are shown in FIG. 17A. These results demonstrate that administration of IRO was able to inhibit IL-6 production by mice B lymphocytes. Purified mouse spleen B cells from wild-type (BALB/c) and lupus prone (NZBW) mice were cultured with 0.01 to 10 μg/ml IRO-17 in the presence of 1 μg/ml IMO, or alone with 10 μg/ml IRO-17, 1 μg/ml IMO or medium for 72 h. The results are shown in FIGS. 17B and 17C. These results demonstrate that administration of an IRO was able to inhibit IL-6 and IL-12 production by mice spleen cells.

Lupus prone MRL-lpr mice were injected once a week s.c. with 100 μg doses of IRO-5 from wk 9 to 18, and 21 to 23 or IRO-17 starting from wk 10 to 15, 100 μg three times week in weeks 18-21 and 40 mg three times a week in weeks 22 to 24. Blood and urine were collected every week before IRO injection. Mice were sacrificed Wk 24. Serum anti-DNA IgG1 levels were determined by ELISA. The results are shown in FIGS. 18A through 18E. These results demonstrate that IRO 5 and IRO 17 can inhibit IgG1 and IgG2A production and urine protein in Lupus prone mice.

Figure 19:
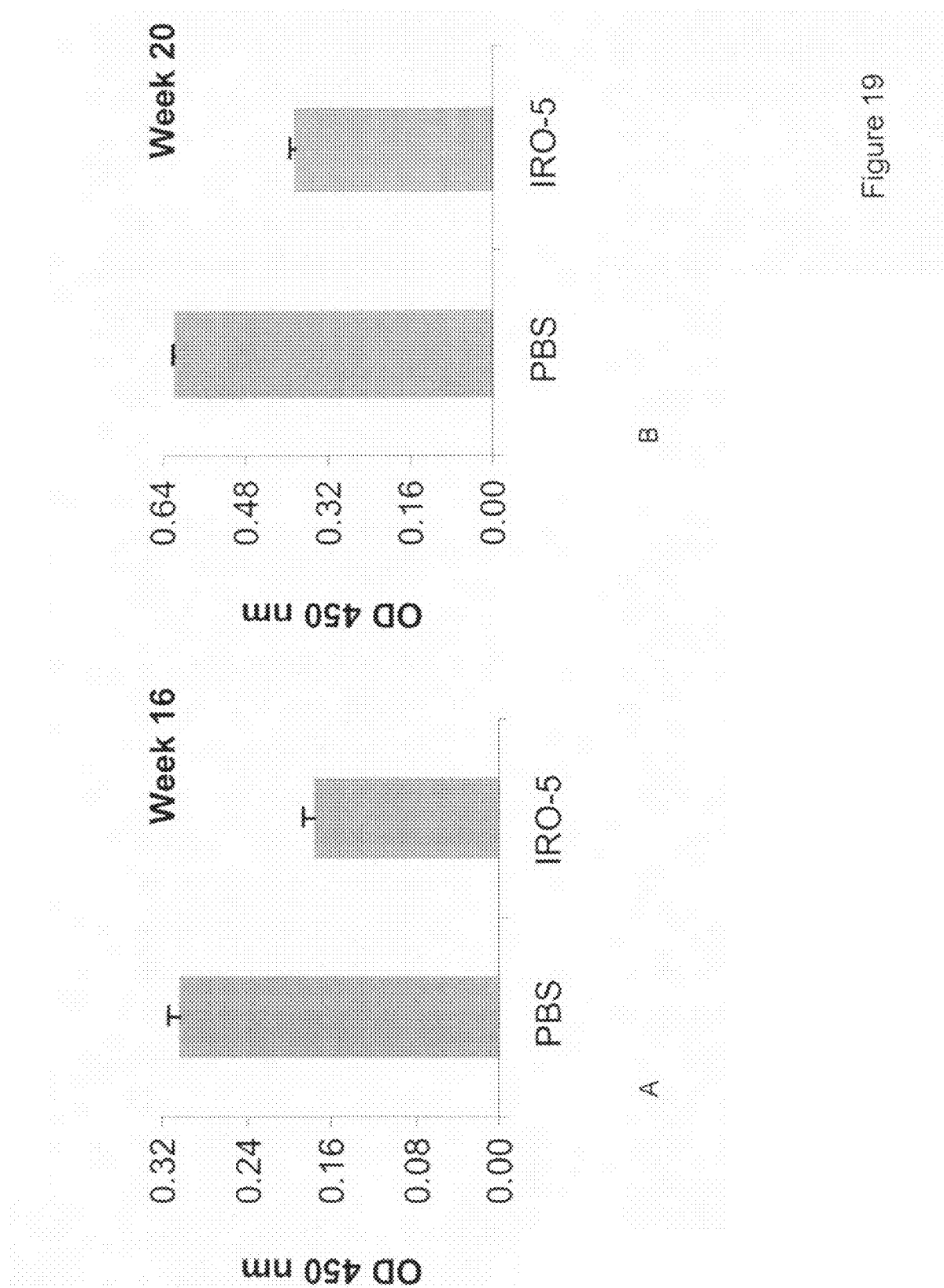
FIGS. 19A and 19B demonstrate that an IRO inhibits serum anti-DNA IgG2a in NZBW mice.

Lupus prone NZBW mice are dosed with 300 μg IRO-5, s.c once in every two weeks starting week 6. Serum anti-DNA IgG2a levels were determined at weeks 16 and 20. The results are shown in FIG. 19. These results demonstrate that administration of IRO inhibits serum anti-DNA IgG2a in NZBW mice.

---

What is claimed is:

1. An immune regulatory oligonucleotide (IRO) compound comprising at least two oligonucleotides linked by a non-nucleotide linker at their 3' ends or by a functionalized sugar or by a functionalized base via a non-nucleotide linker, wherein at least one oligonucleotide has the structure $$5'-N_m-N_3N_2N_1CGN^1N^2N^3-N^m-3':$$

wherein:

CG is an oligonucleotide motif that is CpG, C*pG, C*pG* or CpG*, wherein C is cytosine, C* is a pyrimidine nucleotide derivative, G is guanosine, and G* is a purine nucleotide derivative; $N_1$ is a modified nucleoside that suppresses the activity of the oligonucleotide motif selected from the group consisting of 2'-substituted ribonucleoside, 2'-O-substituted ribonucleoside, 2'-substituted arabinoside, and 2'-O-substituted arabinoside;

$N_2$-$N_3$, at each occurrence, is independently i) a nucleotide, ii) a nucleotide derivative, or iii) a modified nucleoside that suppresses the activity of the oligonucleotide motif selected from the group consisting of 2'-substituted ribonucleoside, 2'-O-substituted ribonucleoside, 2'-substituted arabinoside, and 2'-O-substituted arabinoside;

$N^1$-$N^3$, at each occurrence, is independently i) a nucleotide, or ii) a nucleotide derivative;

$N_n$, and $N^m$, at each occurrence, is independently a nucleotide, nucleotide derivative or non-nucleotide linkage;

and further provided that the compound contains less than 3 consecutive guanosine nucleotides;

wherein the oligonucleotide motif would be immune stimulatory but for the one or more modified nucleosides that suppress the activity of the oligonucleotide motif;

wherein m is a number from 0 to about 30;

wherein the IRO is an antagonist of an agonist of TLR7, TLR8 and/or TLR9; and provided that the at least two oligonucleotides are not antisense oligonucleotides.

2. A pharmaceutical composition comprising an IRO according to claim 1 and a pharmaceutically acceptable carrier.

3. The IRO according to claim 1, wherein the non-nucleotide linker linking the at least two oligonucleotides at their 3' ends or functionalized base or sugar is Glycerol (1,2,3-Propanetriol), 1,2,4, Butanetriol, 2-(hydroxymethyl)-1,3-propanediol, 2-(hydroxymethyl)1,4-butanediol, 1,3,5-Pentanetriol, 1,1,1-Tris(hydroxymethyl)ethane, 1,1,1-Tris (hydroxymethyl)-nitromethane, 1,1,1-Tris(hydroxymethyl) propane, 1,2,6-Hexanetriol, 3-Methyl-1,3,5-pentanetriol, 1,2,3-Heptanetriol, 2-Amino-2-(hydroxymethyl)-1,3-propanediol, N-[Tris(hydroxymethyl)methyl]acrylamide, cis-1, 3,5-Cyclohexanetriol, Cis-1,3,5-Tri(hydroxymethyl)cyclohexane, 3,5-Di(hydroxymethyl)phenol, 1,3,5-Trihydroxylbenzene, 3,5-Di(hydroxymethyl)benzene, 1,3-Di (hydroxyethoxy)-2-hydroxyl-propane, 1,3-Di (hydroxypropoxy)-2-hydroxyl-propane, 2-Deoxy-D-ribose, 1,2,4-Trihydroxyl-benzene, D-Galactoal, 1,6-anhydro-β-D-Glucose, 1,3,5-Tris(2-hydroxyethyl)-Cyanuric acid, Gallic acid, 3,5,7-Trihydroxyflavone, 4,6-Nitropyrogallol, Ethylene glycol, 1,3-Propanediol, 1,2-Propanediol, 1,4-Butanediol, 1,3-Butanediol, 2,3-Butanediol, 1,4-Butanediol, 1,5-Pentanediol, 2,4-Pentanediol, 1,6-Hexanediol, 1,2-Hexanediol, 1,5-Hexanediol, 2,5-Hexanediol, 1,7-Heptanediol, 1,8-Octanediol, 1,2-Octanediol, 1,9-Nonanediol, 1,12-Dodecanediol, Triethylene glycol, Tetraethylene glycol, 2-(1-Aminopropyl)-1,3-propanediol, or 1,2-Dideoxyribose.

4. The IRO according to claim 1, wherein the non-nucleotide linker linking the at least two oligonucleotides at their 3' ends or functionalized base or sugar is Glycerol (1,2,3-Propanetriol).

5. The IRO according to claim 1, wherein the pyrimidine nucleotide derivative is 2-deoxythymidine, 1-(2'-deoxy-α-D-ribofuranosyl)-2-oxo-7-deaza-8-methyl-purine, 2'-dideoxy-5-halocytosine, 2'-dideoxy-5-nitrocytosine, arabinocytidine, T-deoxy-5-hydroxycytidine, 2'-deoxy-N4-alkyl-cytidine, 2'-deoxy-4-thiouridine, or other pyrimidine nucleoside analogs.

6. The IRO according to claim 1, wherein the purine nucleotide derivative is 2'-deoxy-7-deazaguanosine, 2'-deoxy-6-thioguanosine, arabinoguanosine, 2'-deoxyinosine, or other purine nucleoside analogs.

7. The IRO according to claim 1, wherein at least one of the oligonucleotides has the sequence selected from TCT GACGTTCT (SEQ ID NO: 86), TCTGACG$_1$TTCT (SEQ ID NO: 87), TCTGACG$_4$TTCT (SEQ ID NO: 88), TCTCT GACGTT (SEQ ID NO: 89), TCTGUCGTTCT (SEQ ID NO: 93), TCTGUCG$_1$TTCT (SEQ ID NO: 94), TCT GACG$_4$TTCT (SEQ ID NO: 95), TCTGACG$_1$TT (SEQ ID NO: 96), UGUCG$_1$TTCT (SEQ ID NO: 100) and UGACG$_1$TTCT (SEQ ID NO: 101), wherein G$_1$=7-deaza, G$_4$=araG, and G, A or U=2'-OMe.

8. The IRO according to claim 1, wherein the IRO is selected from 5'-(TCTGACGTTCT)$_2$X$_2$(5'-SEQ ID NO: 86-3'-X$_2$-3'-SEQ ID NO: 86-5'), 5'-(TCT GACG$_1$TTCT)$_2$X$_2$(5'-SEQ ID NO: 87-3'-X$_2$-3'-SEQ ID NO: 87-5'), 5'-(TCTGACG$_4$TTCT)$_2$X$_2$(5'-SEQ ID NO: 88-3'-X$_2$-3'-SEQ ID NO: 88-5'), 5'-(TCTCTGACGTT)$_2$X$_2$(5'-SEQ ID NO: 89-3'-X$_2$-3'-SEQ ID NO: 89-5'), 5'-(TCT GUCGTTCT)$_2$X$_2$(5'-SEQ ID NO: 93-3'-X$_2$-3'-SEQ ID NO: 93-5'), 5'-(TCTGUCG$_1$TTCT)$_2$X$_2$(5''-SEQ ID NO: 94-3'-X$_2$-3'-SEQ ID NO: 94-5'), 5'-(TCT GACG$_4$TTCT)$_2$×2(5'-SEQ ID NO: 95-3'-X$_2$-3'-SEQ ID NO: 95-5'), 5'-(TCTGACG$_1$TT)$_2$X$_2$(5'-SEQ ID NO: 96-3'-X$_2$-3'-SEQ ID NO: 96-5'), 5'-(UGUCG$_1$TTCT)$_2$X$_2$(5'-SEQ ID NO: 100-3'-X$_2$-3'-SEQ ID NO: 100-5') and 5'-(UGACG$_1$TTCT)$_2$X$_2$(5'-SEQ ID NO: 101-3'-X$_2$-3'-SEQ ID NO: 101-5'), wherein G$_1$=7-deaza, G$_4$=araG, G, A or U=2'-OMe and X$_2$=glycerol linker.

9. A pharmaceutical composition comprising an IRO according to claim 7 and a pharmaceutically acceptable carrier.

10. A pharmaceutical composition comprising an IRO according to claim 8 and a pharmaceutically acceptable carrier.

11. The IRO according to claim 1, wherein N$_2$ is a 2'-substituted ribonucleoside, 2'-O-substituted ribonucleoside, 2'-substituted arabinoside, or 2'-O-substituted arabinoside.

12. The IRO according to claim 1, wherein the 2'-O-substituted ribonucleoside of N$_1$ is a 2'-OMe-ribonucleoside.

13. The IRO according to claim 11, wherein the 2'-O-substituted ribonucleoside is a 2'-OMe-ribonucleoside.

14. The IRO according to claim 1, wherein the non-nucleotide linker may be attached to the 3' hydroxyl.

15. The IRO according to claim 1, wherein CG is an oligonucleotide motif that is C*pG, C*pG* or CpG*.

* * * * *

UNITED STATES PATENT AND TRADEMARK OFFICE
CERTIFICATE OF CORRECTION

PATENT NO. : 8,357,665 B2
APPLICATION NO. : 11/549048
DATED : January 22, 2013
INVENTOR(S) : Ekambar Kandimalla et al.

It is certified that error appears in the above-identified patent and that said Letters Patent is hereby corrected as shown below:

In the Specifications:

Column 22, line 57, cancel the text "95    5'-(TCT<u>GA</u>CG4TTCT)X2" and replace it with
--95    5'-(TCT<u>GA</u>CG4TTCT)2X2--.

Column 23, line 9, cancel the text "100    5'-(<u>UGU</u>CG1TTCT)X2" and replace it with
--100    5'-(<u>UGU</u>CG1TTCT)2X2--.

Signed and Sealed this
Twenty-third Day of April, 2013

Teresa Stanek Rea
*Acting Director of the United States Patent and Trademark Office*

SEQUENCE LISTING

<160> NUMBER OF SEQ ID NOS: 101

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 1
ctatctgacg ttctctgt                                           18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctatctgtcg ttctctgt                                           18

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-G

<400> SEQUENCE: 3
tctgacnttc t                                                  11

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctatctcacc ttctctgt                                           18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 5
ctatctgacg ttctctgt                                           18

<210> SEQ ID NO 6
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)

-continued

```
<223> OTHER INFORMATION: 2'-OMe

<400> SEQUENCE: 6
ctatctgacg uuctctgt                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 2'-OMe

<400> SEQUENCE: 7
ctatctgacg ttctctgt                                                    18

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgaccggtca                                                             10

<210> SEQ ID NO 9
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 2'-OMe

<400> SEQUENCE: 9
ctatctgucg ttctctgt                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 10
ctatctgucg ttctctgt                                                    18

<210> SEQ ID NO 11
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 11
tcaaccacac a                                                            11

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcctggcggg gaagt                                                        15

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 17
ctatctgacn ttctctgt                                                     18

<210> SEQ ID NO 18

<400> SEQUENCE: 18

000

<210> SEQ ID NO 19
```

```
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 19
ctatctgucn ttctctgt                                                   18

<210> SEQ ID NO 20

<400> SEQUENCE: 20

000

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tctgacgttc t                                                          11

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgttctctgt                                                            10

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acgttctctg t                                                          11

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cgttctctgt                                                            10
```

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: B-L-deoxy nucleoside-C

<400> SEQUENCE: 25
ctatctgang ttctctgt                                                 18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: B-L-deoxy nucleoside-G

<400> SEQUENCE: 26
ctatctgacn ttctctgt                                                 18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: B-L-deoxy nucleoside-C

<400> SEQUENCE: 27
ctatctgtng ttctctgt                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: B-L-deoxy nucleoside-G

<400> SEQUENCE: 28
ctatctgtcn ttctctgt                                                 18

<210> SEQ ID NO 29
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

```
ctatctga                                                          8

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 ctatctgac                                                         9

<210> SEQ ID NO 31
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 ctatctgt                                                          8

<210> SEQ ID NO 32
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 ctatctgtc                                                         9

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 3'-deoxy-nucleoside-C

<400> SEQUENCE: 33
ctatctgang ttctctgt                                              18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-deoxy-nucleoside-G

<400> SEQUENCE: 34
ctatctgacn ttctctgt                                              18

<210> SEQ ID NO 35
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 3'-deoxy-nucleoside-C

<400> SEQUENCE: 35
ctatctgtng ttctctgt                                                 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-deoxy-nucleoside-G

<400> SEQUENCE: 36
ctatctgtcn ttctctgt                                                 18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: araG

<400> SEQUENCE: 37
ctatctgacn ttctctgt                                                 18

<210> SEQ ID NO 38
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: araG

<400> SEQUENCE: 38
ctatctgucn ttctctgt                                                 18

<210> SEQ ID NO 39
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: araC

<400> SEQUENCE: 39
ctatctgang ttctctgt                                                 18

<210> SEQ ID NO 40
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: araC

<400> SEQUENCE: 40
ctatctgung ttctctgt                                                 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 5-OH-dC

<400> SEQUENCE: 41
ctatctgang ttctctgt                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 5-OH-dC
```

```
<400> SEQUENCE: 42
ctatctgung ttctctgt                                            18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 1-(2'-deoxy-beta-D-ribofuranosyl)-2-oxo-7-
      deaza-8-methyl-purine-C

<400> SEQUENCE: 43
ctatctgang ttctctgt                                            18

<210> SEQ ID NO 44
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: 1-(2'-deoxy-beta-D-ribofuranosyl)-2-oxo-7-
      deaza-8-methyl-purine-C

<400> SEQUENCE: 44
ctatctgung ttctctgt                                            18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: N1-Me-dG

<400> SEQUENCE: 45
ctatctgacn ttctctgt                                            18

<210> SEQ ID NO 46
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: N1-Me-dG

<400> SEQUENCE: 46
ctatctgucn ttctctgt                                                       18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: N3-Me-dC

<400> SEQUENCE: 47
ctatctgang ttctctgt                                                       18

<210> SEQ ID NO 48
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (9)
<223> OTHER INFORMATION: N3-Me-dC

<400> SEQUENCE: 48
ctatctgung ttctctgt                                                       18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)
<223> OTHER INFORMATION: 2'-OMe

<400> SEQUENCE: 49
ctatctagcg ttctctgt                                                       18

<210> SEQ ID NO 50
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: 2'-OMe

<400> SEQUENCE: 50
ctatctagcg ttctctgt                                                 18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: 2'-OMe

<400> SEQUENCE: 51
ctatctagcg ttctctgt                                                 18

<210> SEQ ID NO 52
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cctactagcg t                                                        11

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cctactagcg                                                          10

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 3'-deoxy-nucleoside-G

<400> SEQUENCE: 54
cctactancg ttctcatc                                                 18

<210> SEQ ID NO 55
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 3'-OMe-A

<400> SEQUENCE: 55
tccatgncgt tcctgatgc                                                19

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: B-L-deoxy-nucleoside-C
<220> FEATURE:
<221> NAME/KEY: modified_base
<222> LOCATION: (10)
<223> OTHER INFORMATION: B-L-deoxy nucleoside-G

<400> SEQUENCE: 56
ctatctgann ttctctgt                                                 18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: B-L-deoxy nucleoside-C
<220> FEATURE:
<221> NAME/KEY: modified_base
<222> LOCATION: (2)
<223> OTHER INFORMATION: B-L-deoxy nucleoside-T
<220> FEATURE:
<221> NAME/KEY: modified_base
<222> LOCATION: (3)
<223> OTHER INFORMATION: B-L-deoxy nucleoside-A
<220> FEATURE:
<221> NAME/KEY: modified_base
<222> LOCATION: (4)
<223> OTHER INFORMATION: B-L-deoxy nucleoside-T
<220> FEATURE:
<221> NAME/KEY: modified_base
<222> LOCATION: (5)
<223> OTHER INFORMATION: B-L-deoxy nucleoside-C
<220> FEATURE:
<221> NAME/KEY: modified_base
<222> LOCATION: (6)
<223> OTHER INFORMATION: B-L-deoxy nucleoside-T
<220> FEATURE:
<221> NAME/KEY: modified_base
<222> LOCATION: (7)
<223> OTHER INFORMATION: B-L-deoxy nucleoside-G
<220> FEATURE:
<221> NAME/KEY: modified_base
<222> LOCATION: (8)
<223> OTHER INFORMATION: B-L-deoxy nucleoside-A
<220> FEATURE:
<221> NAME/KEY: modified_base
<222> LOCATION: (9)
<223> OTHER INFORMATION: B-L-deoxy nucleoside-C
<220> FEATURE:
<221> NAME/KEY: modified_base
<222> LOCATION: (10)
```

```
<223> OTHER INFORMATION: B-L-deoxy nucleoside-G
<220> FEATURE:
<221> NAME/KEY: modified_base
<222> LOCATION: (11)
<223> OTHER INFORMATION: B-L-deoxy nucleoside-T
<220> FEATURE:
<221> NAME/KEY: modified_base
<222> LOCATION: (12)
<223> OTHER INFORMATION: B-L-deoxy nucleoside-T
<220> FEATURE:
<221> NAME/KEY: modified_base
<222> LOCATION: (13)
<223> OTHER INFORMATION: B-L-deoxy nucleoside-C
<220> FEATURE:
<221> NAME/KEY: modified_base
<222> LOCATION: (14)
<223> OTHER INFORMATION: B-L-deoxy nucleoside-T
<220> FEATURE:
<221> NAME/KEY: modified_base
<222> LOCATION: (15)
<223> OTHER INFORMATION: B-L-deoxy nucleoside-C
<220> FEATURE:
<221> NAME/KEY: modified_base
<222> LOCATION: (16)
<223> OTHER INFORMATION: B-L-deoxy nucleoside-T
<220> FEATURE:
<221> NAME/KEY: modified_base
<222> LOCATION: (17)
<223> OTHER INFORMATION: B-L-deoxy nucleoside-G
<220> FEATURE:
<221> NAME/KEY: modified_base
<222> LOCATION: (18)
<223> OTHER INFORMATION: B-L-deoxy nucleoside-T

<400> SEQUENCE: 57
nnnnnnnnnn nnnnnnnn                                              18

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctatctgacg t                                                     11

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctatctgacg                                                       10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctatctgacg                                                       10

<210> SEQ ID NO 61
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctatctagcg t                                                              11

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctatctagcg                                                                10

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctatctagcg                                                                10

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 64
ctatctaacg ttctctgt                                                       18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe

<400> SEQUENCE: 65
ctatctagcg ttctctgt                                                       18

<210> SEQ ID NO 66
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (7)..(8)
<223> OTHER INFORMATION: 2'-OMe

<400> SEQUENCE: 66
ctatctaucg ttctctgt                                                18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 67
ctatctaacn ttctctgt                                                18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 68
ctatctagcn ttctctgt                                                18

<210> SEQ ID NO 69
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG

<400> SEQUENCE: 69
ctatctaucn ttctctgt                                                18

<210> SEQ ID NO 70
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 70
ctatctagcg t                                                              11

<210> SEQ ID NO 71
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ctatctagcg                                                                10

<210> SEQ ID NO 72
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctatctagcg                                                                10

<210> SEQ ID NO 73
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tcctggaggg gaagt                                                          15

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 2'-OMe

<400> SEQUENCE: 74
ctatctgacg ttctctgt                                                       18

<210> SEQ ID NO 75
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG
```

```
<220> FEATURE:
<221> NAME/KEY: modified_base
<222> LOCATION: (11)..(12)
<223> OTHER INFORMATION: 2'-OMe

<400> SEQUENCE: 75
ctatctgacn uuctctgt                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: 3'-OMe-G

<400> SEQUENCE: 76
cctactancg ttctcatc                                                 18

<210> SEQ ID NO 77
<211> LENGTH: 19
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 3'-OMe-U

<400> SEQUENCE: 77
tccatgacgn tcctgatgc                                                19

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgttctctgt                                                          10

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
acgttctctg t                                                        11

<210> SEQ ID NO 80
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: dU

<400> SEQUENCE: 80
ctatctnacg ttctctgt                                                    18

<210> SEQ ID NO 81
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: dU

<400> SEQUENCE: 81
ctatctgncg ttctctgt                                                    18

<210> SEQ ID NO 82
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctatctgacg                                                             10

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctatctgacg t                                                           11

<210> SEQ ID NO 84
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cgttctctgt                                                             10

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 85
acgttctctg t                                                    11

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe

<400> SEQUENCE: 86
tctgacgttc t                                                    11

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 87
tctgacnttc t                                                    11

<210> SEQ ID NO 88
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: araG

<400> SEQUENCE: 88
tctgacnttc t                                                    11

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(7)
<223> OTHER INFORMATION: 2'-OMe

<400> SEQUENCE: 89
tctctgacgt t                                                    11
```

```
<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 90
tctgacnttc t                                                          11

<210> SEQ ID NO 91
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: 2'-OMe

<400> SEQUENCE: 91
ctatctgtcg uuctctgt                                                   18

<210> SEQ ID NO 92
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (11)..(12)
<223> OTHER INFORMATION: 2'-OMe

<400> SEQUENCE: 92
ctatctgtcn uuctctgt                                                   18

<210> SEQ ID NO 93
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
```

```
<400> SEQUENCE: 93
tctgucgttc t                                                    11

<210> SEQ ID NO 94
<211> LENGTH: 11
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 94
tctgucnttc t                                                    11

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: araG

<400> SEQUENCE: 95
tctgacnttc t                                                    11

<210> SEQ ID NO 96
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 96 tctgacntt                                                        9

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (4)..(5)
<223> OTHER INFORMATION: 2'-OMe
<220> FEATURE:
<221> NAME/KEY: modified_base
<222> LOCATION: (7)
<223> OTHER INFORMATION: 7-deaza-dG

<400> SEQUENCE: 97
tctgacnttc t                                                            11

<210> SEQ ID NO 98
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (15)..(18)
<223> OTHER INFORMATION: 2'-OMe

<400> SEQUENCE: 98
ctatctgacn ttctcugu                                                     18

<210> SEQ ID NO 99
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(8)
<223> OTHER INFORMATION: 2'-OMe
<220> FEATURE:
<221> NAME/KEY: modified_base
<222> LOCATION: (10)
<223> OTHER INFORMATION: 7-deaza-dG
<220> FEATURE:
<221> NAME/KEY: modified_base
<222> LOCATION: (15)..(18)
<223> OTHER INFORMATION: 2'-OMe

<400> SEQUENCE: 99
ctatctgucn ttctcugu                                                     18

<210> SEQ ID NO 100
<211> LENGTH: 9
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

-continued

```
<221> NAME/KEY: modified_base
<222> LOCATION: (1)..(3)
<223> OTHER INFORMATION: 2'-OMe
<220> FEATURE:
<221> NAME/KEY: modified_base
<222> LOCATION: (5)
<223> OTHER INFORMATION: 7-deaza-dG

<400> SEQUENCE: 100 ugucnttct                                                                9

<210> SEQ ID NO 101
<211> LENGTH: 9
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe
<220> FEATURE:
<221> NAME/KEY: modified_base
<222> LOCATION: (5)
<223> OTHER INFORMATION: 7-deaza-dG

<400> SEQUENCE: 101 ugacnttct                                                                9
```